US005998383A

United States Patent [19]
Wright et al.

[11] Patent Number: 5,998,383
[45] Date of Patent: Dec. 7, 1999

[54] ANTITUMOR ANTISENSE SEQUENCES DIRECTED AGAINST RIBONUCLEOTIDE REDUCTASE

[76] Inventors: Jim A. Wright, 15 Bryn Mawr Road, Winnipeg, Manitoba, Canada, R3T 3K8; Aiping H. Young, 717 Pacific Avenue, Winnipeg, Manitoba, Canada, R3E 1G1

[21] Appl. No.: 08/904,901

[22] Filed: Aug. 1, 1997

Related U.S. Application Data

[60] Provisional application No. 60/023,040, Aug. 2, 1996, and provisional application No. 60/039,959, Mar. 7, 1997.

[51] Int. Cl.$^6$ .............................. A61K 48/00; C12Q 1/68; C12N 15/85; C07H 21/04

[52] U.S. Cl. ................................ 514/44; 435/6; 435/91.1; 435/183; 435/325; 435/354; 435/357; 435/366; 435/375; 435/440; 536/23.2; 536/24.31; 536/24.33; 536/24.5

[58] Field of Search ............................ 435/6, 91.1, 91.31, 435/440, 183, 325, 375, 354, 357, 366; 536/23.2, 23.1, 24.31, 24.5, 24.33; 514/44

[56] References Cited

FOREIGN PATENT DOCUMENTS

WO 94/21661   9/1994   WIPO.
WO 95/02069   1/1995   WIPO.

OTHER PUBLICATIONS

Fan et al., The R1 Component of Mammalian Ribonucleotide Reductase Has Malignancy–Suppressing Activity as Demonstrated by Gene Transfer Experiments, Proc. Natl. Acad. Sci. 94, 13181–13186 (1997).

Stull et al., Antigene, Ribozyme and Aptamer Nucleic Acid Drugs: Progress and Prospects, Pharmaceutical Research 12 (4) 465–483 (1995).

Saison–Behmoaras et al., Short Modified Antisense Oligonucleotides Directed Against Ha–Ras Point Mutation Induce Selective Cleavage of the mRNA and Inhibit T24 Cells Proliferation, EMBO J. 10(5) 1111–1118 (1991).

Bjorklund et al., S–Phase —Specific Expression of Mammalian Ribonucleotide Reductase R1 and R2 Subunit mRNAs, Biochemistry 29, 5452–5458 (1990).

Gewirtz et al. PNAS. vol. 93, pp. 3161–3163 (Apr. 1996).

Branch. TIBS. vol. 23. pp. 45–50 (Feb. 1998).

Gura. Science. vol. 278. pp. 1041–1042 (Nov. 7, 1997).

Agrawal, 1996. Antisense oligonucleotides: towards clinical trials, Tibtech, 14:376.

Agarwal et al., 1995. Oncogen, 11:427–438.

Akhter et al, 1991. Interactions of antisense DNA oligonucleotide analogs with phospholipid membranes (liposomes). Nuc. Res. 19:5551–5559.

Alessi et al., 1995. Meth. Enzymol. 255:279–290.

Amara et al., 1994. Phorbol ester modulation of a novel cytoplasmic protein binding activity at the 3'-untranslated region of mammalian ribonucleotide reductase R2 mRNA and role in message stability. J. Biol. Chem. 269:6709–7071.

Amara et al, 1995B. Defining a novel cis element in the 3'-untranslated region of mammalian ribonucleotide reductase component R2 mRNA: Role in transforming growth factor $b_1$ induced mRNA stabilization. Nucleic Acids Res. 23:1461–1467.

Amara et al. 1996. Defining a novel cis–element in the 3'-untranslated region of mammalian ribonucleotide reductase component R2 mRNA: cis–trans interactions and message stability. J. Biol. Chem. 271:20126–20131.

Anazodo et al., 1995. Sequence–Specific Inhibition of Gene Expression by a Novel Antisense oligodeoxynucleotide Phosphonothioate Directed Against a Nonregulatory Region of the Human Immunodeficiency Virus Type 1 Genome. J. Virol. 69: 1794–1801.

Anazodo et al., 1996. Relative Levels of Inhibition of p24 Gene Expression by Different 20–mer Antisense Oligonucleotide Sequences Targeting Nucleotides + 1129 to +1268 of the HIV–1 gag Genome: An Analysis of Mechanism Biochem. Biophys. Res. Commun. 229: 305–309.

Ashihara and Baserga, 1979. Cell Synchronization. Methods Enzymol. 58:248–262.

Blaesse, 1997. Gene Therapy for Cancer. Scientific American 276(6):111–115.

Björklund et al., 1993. Structure and promoter characterization of the gene encoding the large subunit (R1 Protein) of mouse ribonucleotide reductase. Proc. Natl. Acad. Sci. USA 90:11322–11326.

Blin and Stafford, 1976. A general method for isolation of high molecular weight DNA from eukaryotes. Nucleic Acids Res., 3: 2303–2308.

Blosmanis et al., 1987. Cancer Res 47:1273–1277.

Bradley et al., 1986. Proc. Natl. Acad. Sci. USA 83: 5277–5281.

Calabretta, et al, 1996. Antisense strategies in the treatment of leukemias. Semin. Oncol. 23:78.

Caras, 1985. Cloned Mouse Ribonucleotide Reductase Subunit M1 cDNA Reveals Amino Acid Sequence Homology with *Escherichia coli* and Herpesvirus Ribonucleotide Reductases. Biol Chem. 260:7015–7022.

(List continued on next page.)

*Primary Examiner*—John L. LeGuyader
*Assistant Examiner*—Mark L. Shibuya
*Attorney, Agent, or Firm*—Burns, Doane, Swecker & Mathis, L.L.P.

[57] ABSTRACT

A synthetic antisense oligonucleotide comprising at least seven nucleotides or nucleotide analogues having a sequence complementary to the mRNA sequence of ribonucleotide reductase dimeric protein component R2 including SEQ ID Nos:1–102 is disclosed. A synthetic antisense oligonucleotide comprising at least seven nucleotides or nucleotide analogues having a sequence complementary to the mRNA sequence of ribonucleotide reductase dimeric protein component R1 including SEQ ID Nos:103–161 is also disclosed. The invention also discloses pharmaceutical compositions including the synthetic antisense oligonucleotides of the present invention and methods of using the antisense oligonucleotides to modulation proliferative cells including neoplastic cells.

31 Claims, 11 Drawing Sheets

OTHER PUBLICATIONS

Chadee et al, 1995. J. Biol. Chem. 270:20098–20105.

Chan et al., 1993. Biochemistry 32:12835–12840.

Chang et al., 1978. Phenotypic expression in *E. coli* of a DNA sequence coding for mouse dihydrofolate reductase. Nature, 275: 617–624. [*n/a—will mail in].

Chen et al., 1993. Mammalian ribonucleotide reductase R1 mRNA stability under normal and phorbol ester stimulating conditions: involvement of a cis–trans interaction at the 3'–untranslated region. EMBO J., 12:3977–3986.

Chen et al., 1994B. Defining a novel ribonucleotide reductase R1 mRNA cis element that binds to an unique cytoplasmic trans–acting protein. Nucleic Acids Res., 22:4796–4797.

Choy et al., 1988. Molecular mechanisms of drug resistance involving ribonucleotide reductase: hydroxyurea resistance in a series of clonally related mouse cell lines selected in the presence of increasing drug concentrations. Cancer Res. 48:2029–2035.

Damen et al., 1989. Generation of metastatic variants in populations of mutator and amplificator mutants. J. Natl. Cancer Inst. 81:628–631.

Damen et al., 1991. Transformation and amplification of the K–fgf Protooncogene in NIH–3T3 cells, and induction of metastatic potential. Biochem Biophys. Acta 1097:103–110.

Davis et al., 1994. Purification, Characterization, and Localization of Subunit Interaction Area of Recombinant Mouse Ribonucleotide Reductase R1 Subunit. Biol. Chem. 269:23171–23176.

Eckstein 1985. Nucleoside Phosphorothioates. Ann. Rev. Biochem. 54:367–402.

Egan, et al., 1987A. Expression of H–ras Correlates with Metastatic Potential: Evidence for Direct Regulation of the Metastatic Phenotype in 10T1/2 and NIH 3T3 Cells. Mol. Cell. Biol. 7:830–837.

Egan et al., 1987B. Transformation by oncogenes encoding protein kinases induces the metastatic phenotype. Science 238:202–205.

Eriksson et al., 1984. Cell cycle–dependent regulation of mammalian ribonucleotide reductase. The S phase–correlated increase in subunit M2 is regulated by de novo protein synthesis. J. Biol. Chem. 259:11695–11700.

Fan et al., 1996A. Ribonucleotide reductase R2 component is a novel malignancy determinant that cooperates with activated oncogenes to determine transformation and malignant potential. Proc. Natl. Acad. Sci. USA 93:14036–14040.

Fan et al., 1996B. A link between ferritin gene expression and ribonucleotide reductase R2 protein, as demonstrated by retroviral vector mediated stable expression of R2 cDNA. FEBS Lett. 382:145–148.

Felgner, 1997. Nonviral Strategies for Gene Therapy. Scinetific American. Jun., 1997, pp. 102–106.

Flintoff, 1989. Methotrexate, In: Gupta, R.S. (ed.), Drug Resistance in Mammalian Cells, Boca Raton, Florida: CRC Press, 1–14.

Gewirtz, 1993. Oligodeoxynucleotide–based therapeutics for human leukemias, Stem Cells Dayt. 11:96.

Gilboa et al., 1986. Transfer and expression of cloned genes using retroviral vectors. BioTechniques 4(6):504–512.

Gannon et al., 1990. Activating mutations in p53 produce a common conformational effect. A monoclonal antibody specific for the mutant form. EMBO J., 9: 1595–1602.

Hampel and Tritz, 1989. RNA Catalytic Properties of the Minimum (–) sTRSV Sequence. Biochemistry 28:4929–4933.

Hanania, et al 1995. Recent advances in the application of gene therapy to human disease. Am. J. Med. 99:537.

Huang et al., 1995A. Drug resistance and gene amplification potential regulated by transforming growth factor $b_1$ gene expression. Cancer Res. 55:1758–1762.

Huang et al., 1995B. Multiple effects on drug sensitivity, genome stability and malignant potential by combinations of H–as, c–myc and mutant p53 gene overexpression. Int. J. Oncol. 7:57–63.

Hunter, 1995. Protein kinases and phosphatases: The yin and yang of protein phosphorylation and signalling. Cell, 80: 225–236.

Hurta, et al., 1991. Early induction of ribonucleotide reductase gene expression by transforming growth factor $b_1$ in malignant H–ras transformed cell lines. J. Biol. Chem. 266:24097–24100.

Hurta and Wright, 1992. Alterations in the activity and regulation of mammalian ribonucleotide reductase by chlorambucil, a DNA damaging agent. J. Biol. Chem. 267:7066–7071.

Hurta and Wright, 1995. Malignant transformation by H–ras results in aberrant regulation of ribonucleotide reductase gene expression by transforming growth factor $b_1$. J. Cell. Biochem. 57:543–556.

Iyer et al. 1990. J. Org. Chem. 55:4693–4699.

Jelinek et al., 1994. Mol. Cell. Biol., 14:8212–8218.

Jensen et al., 1994. Identification of genes expressed in premalignant breast disease by microscopy–directed cloning. Proc. Natl. Acad. Sci, USA. 91:9257–9261.

Kern et al., 1992. Oncogenic forms of p53 inhibit p53–regulated gene expression. Science, 256: 827–830.

Kohn, 1996. Regulatory genes and drug sensitivity. J. Natl. Cancer Inst., 88: 1255–1256.

Koong et al., 1994. Cancer Res, 54:5273–5279.

Leevers et al., 1994. Nature, 369:411–414.

Lefebvre–D'Hellencourt et al, 1995. Immunomodulation by cytokine antisense oligonucleotides. Eur. Cytokine Netw. 6:7.

Lenormand et al., 1996. J. Biol. Chem., 271:15762–15768.

Lescure, et al., 1994. Preparation and Characterization of Novel Poly(methyoidene Malonate 2.1.2)—Made Nanoparticles. Pharmaceutical research 11(9):1270–1277.

Lev–Lehman et al., 1997. Antisense Oligomers in vitro and in vivo. In *Antisense Therapeutics*, A. Cohen and S. Smicek, eds (Plenum Press, New York).

Lewis et al., 1978. Assay of ribonucleotide reduction in nucleotide–permeable hamster cells. J. Cell Physiol. 94:287–298.

Loke et al, 1989. Characterization of oligonucleotide transport into living cells. PNAS USA 86:3474.

Lowe et al., 1994. Abrogation of oncogene–associated apoptosis allows transformation of p53–deficient cells. Proc. Natl. Acad. Sci. USA, 91: 2026–2030.

Mai, 1994. Overexpression of c–myc precedes amplification of the gene encoding dihydrofolate reductase. Gene, 148: 253–260.

Mann et al., 1988. Ribonucleotide reductase M1 subunit in cellular proliferation, quiescence, and differentiation. J. Cancer Res. 48:5151–5156.

McClarty et al., 1988. Molecular mechanisms responsible for the drug–induced posttranscriptional modulation of ribonucleotide reductase levels in a hydroxyurea–resistant mouse L cell line. Biochemistry, 27: 7524–7531.

McClarty et al., 1990. Increased ferritin gene expression is associated with increased ribonucleotide reductase gene expression and the establishment of hydroxyurea resistance in mammalian cells. J. Biol. Chem. 265:7539–7547.

Miller et al., 1993. Use of retroviral vectors for gene transfer and expression. Meth. Enzymol. 217:581–599.

Morrison, 1991. Suppression of basic fibroblast growth factor expression by antisense oligonucleotides inhibits the growth of transformed human astrocytes. J. Biol. Chem. 266:728.

Otto et al., 1989. Increased incidence of CAD gene amplification in tumorigenic rat lines as an indicator of genomic instability of neoplastic cells. J.Biol. Chem. 264: 3390–3396.

Phillips, 1973. "Dye Exclusion Test for Cell Viability" in Tissue Culture Methods and Applications (editors: P.F. Kruse, Jr. and M.K. Patterson, Jr.), Academic Press, New York and London, pp. 406–408.

Price et al., 1987. Proc. Natl. Acad. Sci. USA 84, 156–160.

Price and Calderwood, 1993. Increased sequence–specific p53–DNA binding activity after DNA damage is attenuated by phorbol esters. Oncogene, 8: 3055–3062.

Qiu et al., 1995. Nature 374:457–459.

Radhakrishnan et al., 1990. The automated synthesis of sulfur–containing oligodeoxyribonucleotides using 3H–1, 2–Benzodithiol–3–One 1,1 Dioxide as a sulfer–transfer reagent. J. Org. Chem. 55:4693–4699.

Reichard, 1993. From RNA to DNA, why so many ribonucleotide reductases? Science 60:1773–1777.

Rosolen et al., 1990. Cancer Res. 50:6316.

Saeki et al., 1995. Immunohistochemical detection of ribonucleotide reductase in human breast tumors. Int. J. Oncol. 6:523–529.

Salem et al., 1993. FEBS Letters 323: 93–95.

Scanlon et al., 1995. Oligonucleotides–mediated modulation of mammalian gene expression. FASEB J. 9:1288.

Shaw et al., 1991. Modified deoxyoligonucleotides stable to exonuclease degradation in serum. Nucleic Acids Res. 19:747–750.

Shigesada et al., 1985. Construction of a cDNA to the hamster CAD gene and its application toward defining the domain for aspartate transcarbamylase. Mol. Cell. Biol., 5: 1735–1742.

Spitzer and Eckstein 1988. Inhibition of deoxynucleases by phosphorothioate groups in oligodeoxyribonucleotides. Nucleic Acids Res. 18:11691–11704.

Stark et al., 1990. Gene Rearrangements, In: B.D. Hames and D.M. Glover (eds.) Frontiers in Molecular Biology, Oxford, United Kingdom: IRL; 99–149.

Stokoe et al., 1994. Activation of Raf as a result of recruitment to the plasma membrane. Science 264:1463–1467.

Stubbe, 1989. Protein radical involvement in biological catalysis? Annu. Rev. Biochem. 58:257–285.

Symons (1989) "Self–cleavage of RNA in the replication of small pathogens of plants and animals", *TIBS* 14:445–450.

Symons (1992) "Small Catalytic RNAs", *Annu. Rev. Biochem.* 61:641–671.

Takenaka et al., 1995. Regulation of the sequence–specific DNA binding function of p53 by protein kinase C and protein phosphatases. J. Biol. Chem., 270: 5405–5411.

Taylor et al., 1992. Evidence for synergistic interactions between ras, myc and a mutant form of p53 in cellular transformation and tumor dissemination. Oncogene 7:1383–1390.

Thelander et al., 1985. Subunit M2 of mammalian ribonucleotide reductase. Characterization of a homogeneous protein isoloated from M2–overproducing mouse cells. J. Biol. Chem. 260:2737–2741.

Thelander et al., 1980. Ribonucleotide reductase from calf thymus. Separation of the enzyme into two nonidentical subunits, proteins M1 and M2. J. Biol. Chem. 255:7426–7432.

Tonin et al., 1987. Chromosomal assignment of amplified genes in hydroxyurea resistant hamster cells. Cytogenet. Cell Genet. 45:102–108.

Uhlenbeck, 1987. "Small catalytic oligoribonucleotide" Nature 328:596–600.

Wagner et al., 1996. Potent and selective inhibition of gene expression by an antisense heptanucleotide. Nature Biotechnology 14:840–844.

Weber, 1983. Biochemical strategy of cancer cells and the design of chemotherapy. Cancer Res. 43:3466–3492.

Whitesell et al., 1991. Episome–generated N–myc antisense RNA restricts the differentiation potential of primitive neuroectodermal cell lines. Mol. Cell. Biol. 11:1360.

Wright et al., 1987. Altered Expression of Ribonucleotide Reductase and Role of M2 Gene Amplification in Hydroxyurea–Resistant Hamster, Mouse, Rat, and Human Cell Lines. Somat. Cell Mol. Genet. 13:155–165.

Wright, 1989A. Altered mammalian ribonucleotide reductase from mutant cell lines. Encycl. Pharmacol. Therapeut. 128:89–111.

Wright et al., 1989B. Hydroxyurea and related compounds. In: R.S. Gupta (ed.), Drug Resistance in Mammalian Cells, Boca Raton, FL; CRC Press, Inc; 15–27.

Wright et al., 1990A. Regulation and drug resistance mechanisms of mammalian ribonucleotide reductase and the significance to DNA synthesis. Biochem. Cell Biol. 68:1364–1371.

Wright et al., 1993. Transforming growth factor b and fibroblast growth factor as promoters of tumor progression to malignancy. Crit. Rev. Oncogene. 4:473–492.

Yakubov et al, 1989. PNAS USA 86:6454.

Yin et al., 1992. Wild–type p53 restores cell cycle control and inhibits gene amplification in cells with mutant p53 alleles.

Altschul, S.F., et al., Basic Local Alignment Search Tool, 1990.

Barker, R.H. Jr. et al., Inhibition of plasmodium falciparum malaria using antisense oligodeoxynucleotides, Proc. Natl. Acad. Sci. USA, 93(1):514–518, 1996.

Bjorklund S., et al., S–Phase–Specific Expression of Mammalian Ribonucleotide Reductase R1 and R2 Subunit mRNAs, Biochemistry, 29(23):5452–5458, 1990.

Chakrabarti D., et al., Cloning and characterization of subunit genes of ribonucleotide reductase, a cell–cycle–regulated enzyme, from Plasmodium falciparum, Proc. Natl. Acad. Sci, USA, 90:12020–12024, 1993.

Chaudhuri, M.M., et al., cDNA sequence of the small subunit of the hamster ribonucleotide reductase, Biochimica et Biophysica Acta, 1117:117–121, 1992.

Cregg, J.M. et al., Recent Advances in the Expression of Foreign Genes in Pichia pastoris, Bio/Technology, 11:905/910, 1993.

Greene L.A., et al., Establishment of a noradrenergic clonal line of rat adrenal pheochromocytoma cells which respond to nerve growth factor, Proc. Natl. Acad. Sci, USA, 73(7):2424–2428, 1976.

Gubler, U., et el., A simple and very efficient method for generating cDNA libraries, Gene, 25:263–269, 1983.

Huang, A., et al., Ribonucleotide Reductase R2 Gene Expression and Changes in Drug Sensitivity and Genome Stability, Cancer Research, 57:4876–4881, 1997.

Hurta, R.A.R., et al., Early Induction of Ribonucleotide Reductase Gene Expression by Transforming Growth Factor Beta1 in Malignant H–ras Transformed Cell Lines, The Journal of Biological Chemistry, 266(35):24097–24100, 1991.

Kijima, H., et al. Therapeutic Applications of Ribozymes, Pharmac. Ther., 68(2):247–267, 1995.

Mader, R.M., et al., Transcription and Activity of 5–Fluorouracil Converting Enzymes in Fluoropyrimidine Resistance in Colon Cancer In Vitro, Biochemical Pharmacology, 54:1233–1242, 1997.

Pavloff, N., et al., Sequence Analysis of the Large and Small Subunits of Human Ribonucleotide Reductase, DNA Sequence, 2:227–234, 1992.

Saeki, T., et al., Immunohistochemical detection of ribonucleotide reductase in human breast tumors, International Journal of Oncology, 6:523–529, 1995.

Standart, N., et al., Control of Translation of Masked mRNAs in Clam Oocytes, Enzyme, 44:106–119, 1990.

Standart, N., et al., Maternal mRNA from clam oocytes can be specifically unmasked in vitro by antisense RNA complementary to the 3'–untranslated region, Genes & Development, 4:2157–2168, 1990.

Thelander, L., et al., Isolation and Characterization of Expressible cDNA Clones Encoding the M1 and M2 Subunits of Mouse Ribonucleotide Reductase Molecular and Cellular Biology, 6(10):3433–3442, 1986.

Thelander, M., et al., Molecular cloning and expression of the functional gene encoding the M2 subunit of mouse ribonucleotide reductase: a new dominant marker gene, The EMBO Journal, 8(9):2475–2479, 1989.

Boven et al., (1992) "Phase II Preclinical Drug Screening in Human Tumor Xenografts: A First European Multicenter Collaborative Study" Cancer Research 52:5940–5947.

Chang et al., (1978) "Phenotypic Expression in E. coli of a DNA Sequence Coding for Mouse Dihydrofolate Reductase" Nature 275:617–624.

Crooke, (1995) "Progress in Antisense Therapeutics" Hematologic Pathology 9(2):59–72.

Fujita et al.,(1980) "Relationship of Chemotherapy on Human Cancer Xenografts in Nude Mice to Clinical Response in Donor Patient" Journal of Surgical Oncology 15:211–219.

Fujita and Taguchi, (1982) "Application of Nude Mouse–Human Cancer Xenograft Systems for Sensitivity Test of Anticancer Drugs" Gan To Kagaku Ryoho 9(4): 606–615 (English abstract).

Fujita et al., (1984) "Experimental Chemotherapy of Human Gastrointestinal and Breast Cancers in Nude Mice and its Correlation to Clinical Effect" Gan No Rinsho 30(9 Supp): 1168–1174 (English abstract).

Fujita et al., (1991) "Predictability of Preclinical Evaluation of Anticancer Drugs by Huamn Gastrointestinal Cancer—Nude Mouse Panel" Gan To Kagaku Ryoho 18(9): 1429–1437 (English abstract).

Furukawa et al., (1993) "Orthotopic Transplantation of Histologically Intact Clinical Specimens of Stomach Cancer to Nude Mice: Correlation of Metastic Sites in Mouse and Individual Patient Donors" Int. J. Cancer 53:608–612.

Giovanella et al., (1983) "Correlation Between Response to Chemotherapy of Human Tumors in Patients and in Nude Mice" Cancer 52:1146–1152.

Livingston et al., (1992) "Altered Cell Cycle Arrest and Gene Amplification Potential Accompany Loss of Wild–type p53" Cell 70:923–935.

Sakamoto et al., (1993)"Accordance of the Chemosensitivity Between Clinical Specimens and Their Xenografts in Nude Mice by SDI Test and the Value of in vivo Chemosensitivity Test Using Nude Mice" Gan To Kagaku Ryoho 20(4):447–454 (English Abstract).

Schabet and Herrlinger, (1998) "Animal Models of Leptomeningeal Metastasis" Journal of Neuro–Oncology 38:199–205.

Stark, (1993) "Regulation and Mechanisms of Mammalian Gene Amplification" Adv. Cancer Res. 61:87–113.

Sullivan, (1994) "Development of Ribozymes for Gene Therapy" J. of Investigative Dermatology 103(5)Supp:86S–89S.

Wagner (1994) "Gene Inhibition Using Antisense Oligodeoxynucleotides" Nature 372:333–335.

Winograd et al., (1987) "Human Tumor Xenografts in the Nude Mouse and Their Value as Test Models in Anticancer Drug Development (review)" n Vivo 1(1)1–13 (abstract only).

Woolf et al., (1990) "The Stability, Toxicity and Effectiveness of Unmodified and Phosphorothioate Antisense Oligodeoxynucleotides in Xenopus Oocytes and Embryos" Nucleic Acids Res. 18(7):1763–1769.

FIG. 2A
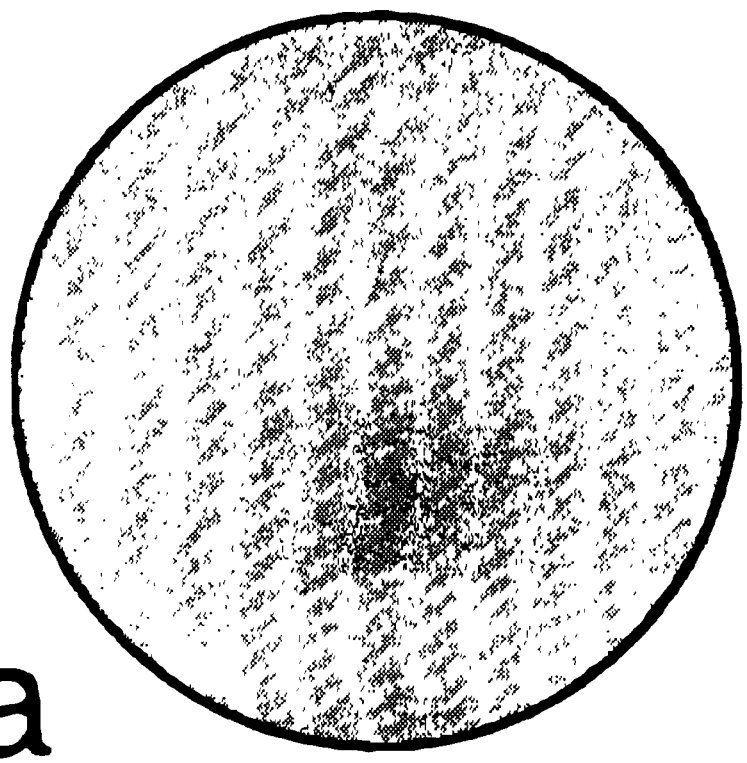
a
b

FIG. 2B
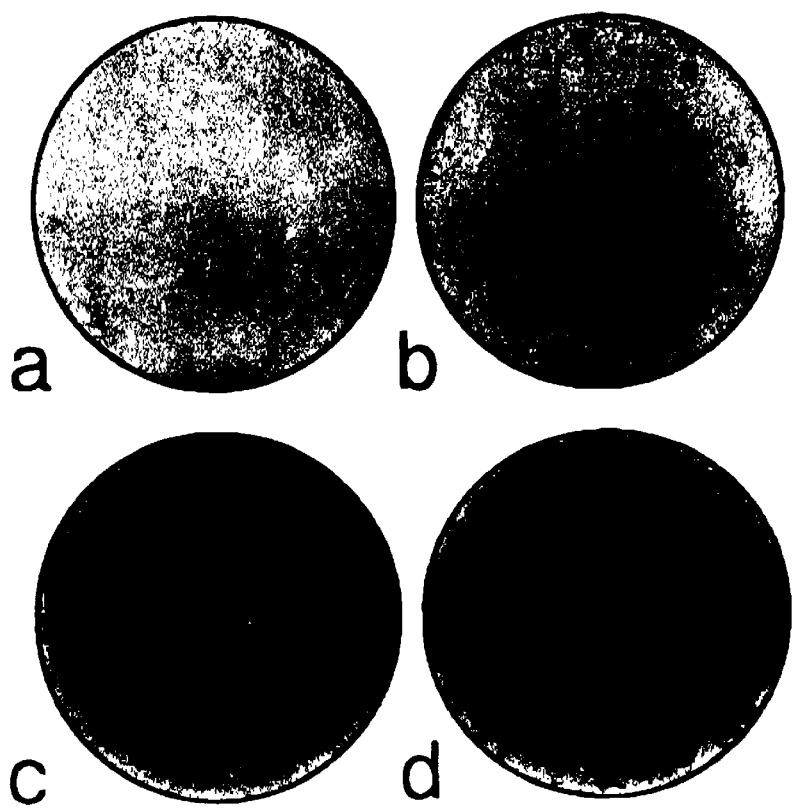
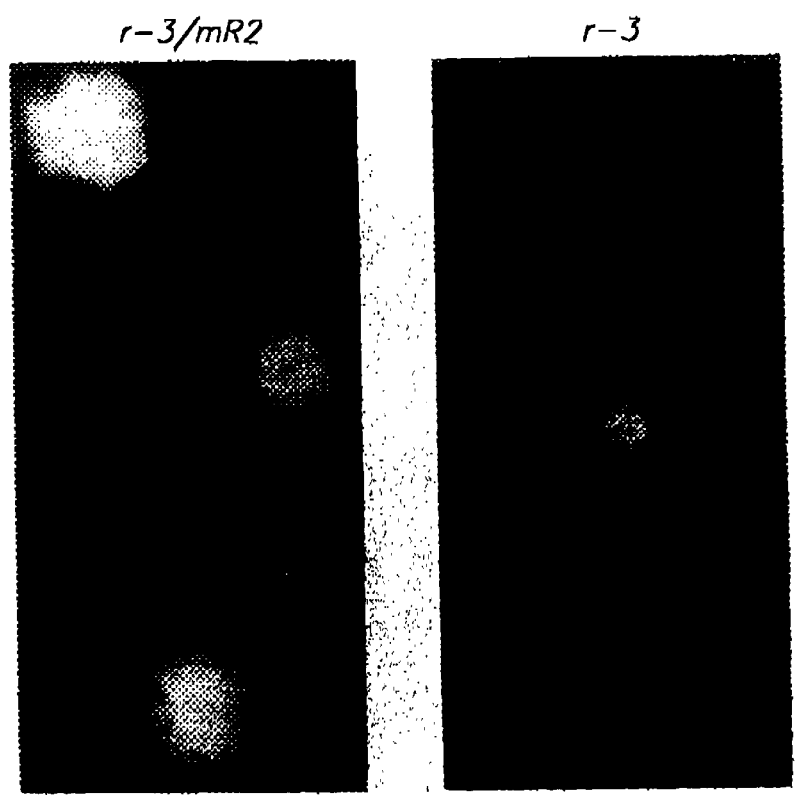
FIG. 3A

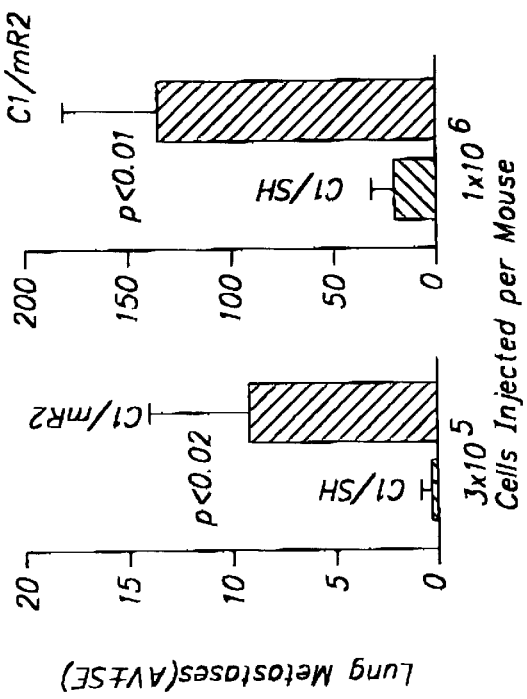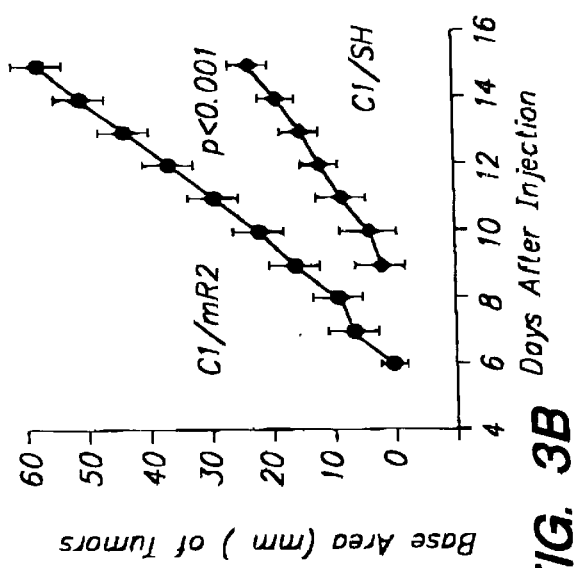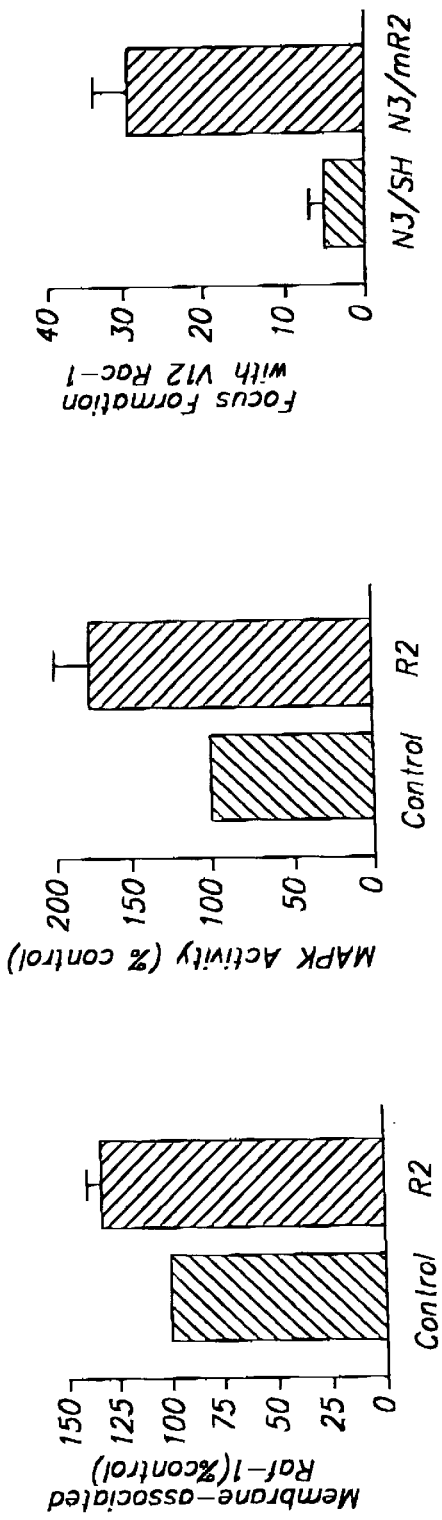

ANTITUMOR ANTISENSE SEQUENCES DIRECTED AGAINST RIBONUCLEOTIDE REDUCTASE

This application claims benefit under 35 USC §119(e) of United States Provisional Application Ser. No. 60/023,040, filed Aug. 2, 1996 and United States Provisional Application Ser. No. 60/039,959, filed Mar. 7, 1997.

FIELD OF THE INVENTION

The field of this invention relates to methods of controlling the tumorigenicity and/or metastasis of neoplastic cells. Specifically it relates to the use of antisense sequences directed against the R1 and R2 components of ribonucleotide reductase.

BACKGROUND OF THE INVENTION

The first unique step leading to DNA synthesis is the conversion of ribonucleotides to their corresponding deoxyribonucleotides, a reaction that is catalyzed in a cell cycle specific manner by the housekeeping gene ribonucleotide reductase [Lewis et al., 1978; Reichard, 1993; Wright, 1989a; Wright et al., 1990a; Stubbe, 1989]. The mammalian enzyme is composed of two dissimilar dimeric protein components often called R1 and R2, which are encoded by two different genes located on different chromosomes [Bjorklund et al., 1993; Tonin et al., 1987]. Mammalian protein R1 is a homodimeric structure, with a molecular weight of about 170 kDa, and has substrate sites and allosteric effector sites that control enzyme activity and substrate specificity [Wright, 1989a; Thelander et al., 1980; Caras et al., 1985; Wright et al., 1990a]. Protein R2 is a homodimer, with a molecular weight of 88 kDa, and forms two equivalent dinuclear iron centers that stabilizes a tyrosyl free radical required for catalysis [Wright et al., 1990a; Thelander et al., 1985; McClarty et al., 1990]. R1 and R2 proteins interact at their C-terminal ends to form an active holoenzyme [Reichard, 1993; Wright et al., 1990a; Davis et al., 1994].

R1 and R2 are differentially regulated during the cell cycle. There is an S-phase correlated increase in the R2 protein resulting from its de novo synthesis [Lewis et al., 1978; Mann et al, 1988]. The activity of ribonucleotide reductase, and therefore DNA synthesis and cell proliferation, is controlled in proliferating cells during the cell cycle by the synthesis and degradation of the R2 component [Eriksson et al., 1984]. The rate-limiting R2 component is a phosphoprotein capable of being phosphorylated by the CDC2 and CDK2 protein kinase mediators of cell cycle progression [Chan et al., 1993], and contains non-heme iron that stabilizes an unique tyrosyl free radical required for enzyme activity [Reichard, 1993; McClarty et al., 1990].

The levels of the R1 protein do not appear to change substantially during the cell cycle of proliferating cells and can be detected throughout the cell cycle. Synthesis of R1 mRNA, like R2 mRNA appears to occur mainly during S phase [Eriksson et al., 1984; Choy et al., 1988; Mann et al., 1988]. The broader distribution of the R1 protein during the cell cycle is attributed to its longer half life as compared to the R2 protein [Choy et al., 1988; Mann et al., 1988].

Regulation of ribonucleotide reductase, and particularly the R2 component, is altered in malignant cells exposed to some tumor promoters and to the growth factor TGF-β [Amara, et al., 1994; Chen et al., 1993; Amara et al., 1995b; Hurta and Wright, 1995; Hurta et al., 1991]. Higher levels of enzyme activity have been observed in cultured malignant cells when compared to nonmalignant cells [Weber, 1983; Takeda and Weber, 1981; Wright et al., 1989a], and increased levels of R2 protein and R2 mRNA have been found in pre-malignant and malignant tissues as compared to normal control tissue samples [Saeki et al., 1995; Jensen et al., 1994]. However, these correlative studies did not show a direct role for ribonucleotide reductase in cancer cell transformation and tumor progression, because like so many other enzyme activities found to be altered in cancer cells [e.g. Weber, 1983], the results could easily be explained by the increased cell proliferation and altered cell cycle regulation characteristics of transformed and malignant cell populations [Morgan and Kastan, 1997].

Breakthroughs in molecular biology and the human genome project have opened previously unforeseen possibilities for targeted intervention with mammalian gene expression [Blaese, 1997; Felgner, 1997]. These include approaches such as disruption of specific genes. Antisense (AS) oligonucleotides (AS-ON) designed to hybridize with specific sequences within a targeted mRNA are one example of such targeted intervention. In general, antisense oligonucleotides interact well with phospholipid membranes [Akhter et al., 1991]. Following their interaction with the cellular plasma membrane, they may be actively, or passively, transported into living cells [Loke et al., 1989], and this may occur by a saturable mechanism predicted to involve specific receptors [Yakubov et al., 1989].

Many excellent reviews have covered the main aspects of antisense technology and its enormous therapeutic potential. There are reviews on the chemical [Crooke, 1995], cellular [Wagner, 1994] and therapeutic [Hanania, et al, 1995; Scanlon, et al, 1995; Gewirtz, 1993] aspects of this rapidly developing technology. Within a relatively short time, ample information has accumulated about the in vitro use of AS-ON in cultured primary cells and cell lines as well as for in vivo administration of such AS-ON for suppressing specific processes and changing body functions in a transient manner. Further, enough experience is now available in vitro and in vivo in animal models to predict human efficacy.

It would be useful to have antisense oligonucleotides available to control tumorigenicity and/or metastatic potential in premalignant or malignant cells wherein the R1 and R2 components of ribonucleotide reductase were utilized.

SUMMARY OF THE INVENTION

The present inventors have shown that aberrant expression of the R2 gene can determine the malignant characteristics of cells. Altered R2 gene expression was found to cooperate with ras in mechanisms of malignant progression, and recombinant R2 expression resulted in increased membrane associated Raf-1 protein. These results suggest that R2 cooperates with Raf-1 and Rac-1 thereby affecting ras pathways and accordingly cell proliferation and in particular malignant progression.

The present inventors also showed that suppression of R2 gene expression reduced transformed properties of neoplastic cells. In particular, the present inventors demonstrated that novel R2 antisense decreased transformation. R1 antisense also suppressed transformed properties of neoplastic cells. The R1 and R2 antisense are effective at low concentrations, and surprisingly normal cells were less sensitive to the antisense molecules.

Aberrant expression of R2 was also found to result in increased resistance of neoplastic cells to chemotherapeutic agents. R2 antisense decreased resistance of neoplastic cells to chemotherapeutic agents at concentrations of antisense that alone did not kill the neoplastic cells.

Broadly stated the present invention relates to compounds and methods for modulating cell proliferation, preferably inhibiting the proliferation of tumor cells. Compounds that may be used to modulate cell proliferation include inhibitors of ribonucleotide reductase expression i.e. inhibitors of transcription or translation of the gene encoding ribonucleotide reductase. Antisense oligonucleotides complimentary to regions of the ribonucleotide reductase gene are particularly useful inhibitors.

In one embodiment, the present invention provides an antisense oligonucleotide having a sequence which is complimentary to a nucleic acid sequence from a ribonucleotide reductase gene and comprises at least seven nucleotides or nucleotide analogues. In a preferred embodiment, the oligonucleotide is complimentary to an mRNA region from a ribonucleotide reductase gene, more preferably the ribonucleotide reductase R1 or R2 gene.

The invention also relates to a method of evaluating if a compound inhibits transcription or translation of a ribonucleotide reductase gene and thereby effects cell proliferation comprising transfecting a cell with an expression vector comprising a recombinant molecule comprising a nucleic acid sequence encoding ribonucleotide reductase, and the necessary elements for the transcription or translation of the nucleic acid; administering a test compound; and comparing the level of expression of the ribonucleotide reductase with the level obtained with a control in the absence of the test compound.

A method is also contemplated for evaluating a compound for its ability to regulate a Ras signalling pathway by assaying for an agonist or antagonist of the interaction of R2 and Raf-1 and/or Rac-1 comprising providing a reaction mixture containing R2 and Raf-1 and/or Rac-1 under conditions which permit the interaction of R2 and Raf-1 and/or Rac-1, in the presence of a test compound; detecting the formation of complexes between R2 and Raf-1 and/or Rac-1 or activation of a Ras signalling pathway; and comparing to a control reaction in the absence of the test substance, wherein lower levels of complexes or activation in the reaction mixture indicate that the test compound interferes with the interaction of R2 and Raf-1 and/or Rac-1, and higher levels indicate that the test compound enhances the interaction of R2 and Raf-1 and/or Rac-1.

The present invention also provides a pharmaceutical composition for modulating cell proliferation, preferably tumor cell proliferation, comprising at least one inhibitor of expression of R1 or R2, preferably an antisense oligonucleotide according to the present invention, or a compound identified in accordance with a method of the invention, in admixture with a physiologically acceptable carrier or diluent.

The present invention also contemplates a method of modulating cell proliferation, preferably tumor cell proliferation by contacting a cell with an effective amount of at least one compound that inhibits the expression of R2 or R1, preferably an antisense oligonucleotide according to the present invention, or a compound identified in accordance with a method of the invention.

The present invention also provides a method for reducing cell proliferation, preferably tumor cell proliferation, comprising contacting a cell with an effective amount of an inhibitor of the expression of R1 or R2 preferably, antisense oligonucleotide according to the present invention, or a compound identified in accordance with a method of the invention.

The present invention also provides a pharmaceutical composition for increasing the sensitivity of a tumor cell to a chemotherapeutic drug comprising at least one inhibitor of expression of R1 or R2, preferably an antisense oligonucleotide according to the present invention, or a compound identified in accordance with a method of the invention, in admixture with a physiologically acceptable carrier or diluent. The present invention further provides a pharmaceutical composition for modulating the growth of a tumor cell that is resistant to a chemotherapeutic drug comprising at least one inhibitor of expression of R1 or R2, preferably an antisense oligonucleotide according to the present invention, or a compound identified in accordance with a method of the invention, in admixture with a physiologically acceptable carrier or diluent.

The invention also contemplates the use of an antisense oligonucleotide according to the present invention, or a compound identified in accordance with a method of the invention, to prepare a medicament for modulating cell proliferation.

DESCRIPTION OF THE DRAWINGS

Other advantages of the present invention will be readily appreciated as the same becomes better understood by reference to the following detailed description when considered in connection with the accompanying drawings wherein:

FIG. 2A–C are photographs (A and B) and a graph (C) of experiments measuring transformed foci wherein (A) shows infection of BALB/c 3T3 (a) and NIH 3T3 (b) cells with SH/mR2 did not lead to focus formation. (B) There was an increase in focus formation with B3/mR2 (b) and N3/mR2 (d) compared to B3/SH (a) and N3/SH (c) after transfection with the T24 H-ras plasmid. (C) The number of foci formed in three independent ras transfection experiments was plotted.

FIG. 3A–C are photographs of soft agar growth (A) and graphs (B and C) wherein (A) shows expression of Myc-R2 in ras-transformed cells resulted in an increased growth efficiency in soft agar. Examples shown are r-3/mR2 and uninfected r-3 cells (See Table 1). (B) C1/mR2 cells showed reduced tumor latency and increased growth rate when compared to C1/SH control cells where $3 \times 10^5$ cells from logarithmically growing cultures were collected and subcutaneously injected into five syngeneic C3H/HeN mice/cell line/experiment. Results presented are from two independent experiments. The p value of t test analysis of tumor growth rates is shown, and indicates that the growth rates for the two cell lines are significantly different. (C) C1/mR2 cells exhibited elevated metastatic potential.

FIG. 4A–C are graphs wherein (A) shows an increased amount of Raf-1 protein associated with the membrane in R2 overexpressing cells. The recombinant R2 expressing cell lines B3/mR2, N3/mR2, C1/mR2, r-2/mR2, r-3/mR2 and NR4/mR2 (R2) were compared to their respective control lines, B3/SH, N3/SH, C1/SH, r-2/SH, r-3, and NR4 (control). In all cases, cells expressing recombinant R2 exhibited increased membrane associated Raf-1 protein, and when the two groups of cell lines were compared, they were found to be significantly different by t test analysis ($p<0.001$). (B) Also shows an increase in the activity of mitogen activating protein kinase (MAPK-2) in R2 overexpressing cells. The recombinant R2 expressing lines B3/mR2, N3/mR2, 10T/mR2, C1/mR2, r-2/mR2 and NR4/mR2 (R2) were compared to their respective control lines infected with LXSH (controls). In all cases tested, cells expressing recombinant R2 showed increased enzyme activity, and the difference between two groups was highly significant (p<0.001). (C) Shows increased foci formation with N3/mR2 cells compared to N3/SH cells after transfection with the activated V12 Rac-1 plasmid [Jelinek et al., 1994]. The number of foci shown represents the average±SE from two independent experiments.

DETAILED DESCRIPTION OF THE PREFERRED EMBODIMENT

Figure 1A:
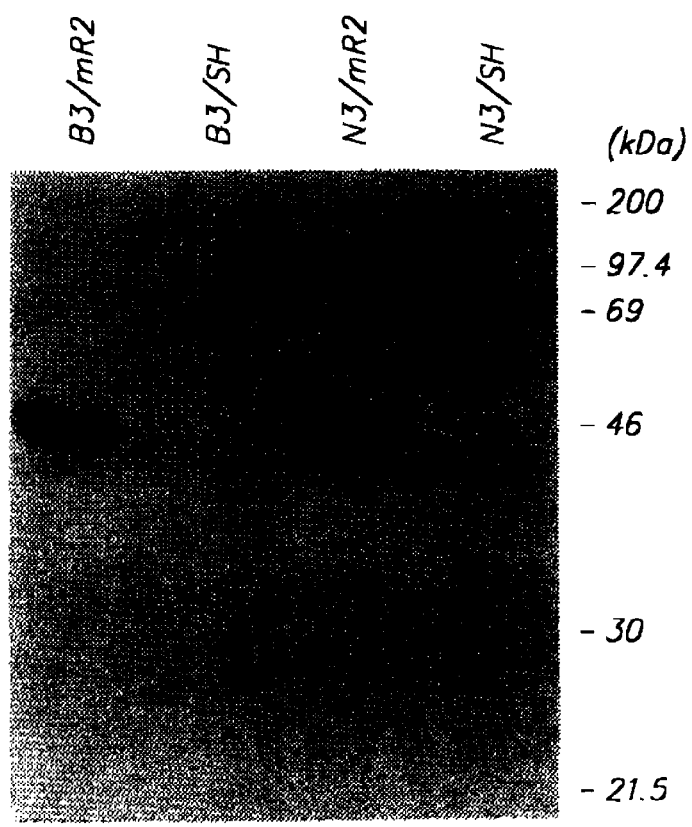
FIG. 1A–C are photographs of gels (A and B) and two scans (C) showing the analysis of Myc-tagged R2 expression from stable infectants by Western blot analysis using monoclonal anti-Myc epitope antibody 9E10 (A), polyclonal rabbit anti-R2 serum (B), and during the cell cycle by flow cytometry [Blosmanis et al, 1987; Chadee et al, 1995], using antibody 9E10 (C).

The present invention provides compounds that inhibit the expression of a ribonucleotide reductase protein and thereby modulate cell proliferation. The compounds may inhibit the expression of the ribonucleotide reductase by inhibiting the transcription of the gene, or the translation of the mRNA to protein. Such compounds may include antisense oligonucleotides and ribozymes.

The present invention relates to antisense oligonucleotides having the complementary sequence of the R2 component of mRNA from ribonucleotide reductase and which can modulate the tumorigenicity of neoplastic cells. The present invention provides a synthetic antisense oligonucleotide comprising a complementary sequence for the entire R2 mRNA sequence and can be formed from ribonucleotides or deoxyribonucleotides.

Short synthetic antisense oligonucleotide sequences designed to hybridize with specific sequences within a targeted mRNA have been shown to suppress gene function. Therefore the present invention provides short antisense oligonucleotides having a sequence corresponding to a sequence segment of at least seven consecutive nucleotides complementary to the mRNA from ribonucleotide reductase and can be formed from ribonucleotides or deoxyribonucleotides. The antisense oligonucleotides can be 7 nucleotides in length or longer; and may be up to 30–35 nucleotides in length. The antisense nucleotides are made and delivered as discussed herein below.

The term "antisense oligonucleotide" as used herein means a nucleotide sequence that is complimentary to its target.

The short antisense R2 oligonucleotides in an embodiment have the sequences as set forth in SEQ ID Nos:1–102. In a preferred embodiment the antisense oligonucleotides have a sequence as set forth in SEQ ID Nos 1 and 2 and those set forth in Table 12. In a still further preferred embodiment, the following sequences are used: SEQ ID Nos:1, 2, 12, 16, 18, 21, 25, 29, 34, 42, 44, 45, 46, 52, 53, 59, 60, 64, 65, 66, 68, 69, 70, 72, 73, 74, 76, 78, 79, 80, 90, 91, 92, 96, 99, 100, and 102.

The present invention also provides short synthetic antisense (AS) oligonucleotide sequences designed to hybridize (complement) with specific sequence segments within the R1 mRNA. The synthetic antisense oligonucleotide comprises at least seven nucleotides or nucleotide analogues thereof and can be formed from ribonucleotides or deoxyribonucleotides complementary to the R1 component mRNA from ribonucleotide reductase. The antisense nucleotides are made and delivered as discussed herein below.

The synthetic antisense R1 oligonucleotides in an embodiment have the sequences as set forth in SEQ ID Nos:103–161. In a preferred embodiment the antisense oligonucleotide has a sequence as set forth in SEQ ID No:103.

The sequence segment is selected such that the sequence exhibits suitable energy related characteristics important for oligunucleotide duplex formation with their complementary templates, and shows a low potential for self-dimerization or self-complementation [Anazodo et al., 1996]. The computer program OLIGO (Primer Analysis Software, Version 3.4), is used to determine antisense sequence melting temperature, free energy properties, and to estimate potential self-dimer formation and self-complimentarity properties. The program allows the determination of a qualitative estimation of these two parameters (potential self-dimer formation and self-complimentary) and provides an indication of "no potential" or "some potential" or "essentially complete potential". Segments were generally selected that had estimates of no potential in these parameters. However, segments can be used that have "some potential" in one of the categories. A balance of the parameters is used in the selection. Further, the oligonucleotides are also selected as needed so that analogue substitution do not substantially affect function.

Ribonucleotide reductase is a dimeric protein consisting of components designated R1 and R2. As described herein above, two genes (R1, sometimes called M1, and R2, sometimes called M2) on separate chromosomes are involved in the production of the protein. As discussed herein, when referring to the ribonucleotide reductase gene, both genes are generally implied except as is apparent from the context.

By inhibition of growth is meant that the proliferating cell, generally a tumor cell, returns to a differentiated normal growth pattern and/or is killed and/or surviving cells are no longer tumorigenic (undifferentiated cell division or growth; tumor forming) or metastatic.

The term neoplastic cells (tumor cells) encompasses proliferating disorders including cancers such as leukemias, lymphomas and carcinomas of solid tissues including sarcomas, and carcinomas.

The term "oligonucleotide" refers to an oligomer or polymer of nucleotide or nucleoside monomers consisting of naturally occurring bases, sugars and intersugar (backbone) linkages. The term also includes modified or substituted oligomers comprising non-naturally occurring monomers or portions thereof, which function similarly. Incorporation of substituted oligomers is based on factors including enhanced cellular uptake, or increased nuclease resistance and are chosen as is known in the art. The entire oligonucleotide or only portions thereof may contain the substituted oligomers.

Antisense intervention in the expression of specific genes can be achieved by the use of synthetic antisense oligonucleotide sequences [for recent reports see Lefebvre-d'Hellencourt et al, 1995; Agrawal, 1996; Lev-Lehman et al, 1997]. Antisense oligonucleotide sequences may be short sequences of DNA, typically 15–30 mer but may be as small as 7 mer [Wagner et al, 1996], designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation [Calabretta et al, 1996]. In that case, RNase H will cleave the RNA component of the duplex and can potentially release the AS to further hybridize with additional molecules of the target RNA. An additional mode of action results from the interaction of AS with genomic DNA to form a triple helix which may be transcriptionally inactive.

Antisense induced loss-of-function phenotypes related with cellular development were shown for the glial fibrillary acidic protein (GFAP), for the establishment of tectal plate formation in chick [Galileo et al., 1991] and for the N-myc protein, responsible for the maintenance of cellular heterogeneity in neuroectodermal cultures (ephithelial vs. neuroblastic cells, which differ in their colony forming abilities, tumorigenicity and adherence) [Rosolen et al., 1990; Whitesell et al, 1991]. Antisense oligonucleotide inhibition of basic fibroblast growth factor (bFgF), having mitogenic and angiogenic properties, suppressed 80% growth of glioma cells [Morrison, 1991] in a saturable and specific manner.

Instead of an antisense sequence as discussed herein above, ribozymes may be utilized for suppression of gene function. This is particularly necessary in cases where antisense therapy is limited by stoichiometric considerations [Sarver et al., 1990, Gene Regulation and Aids, pp. 305–325]. Ribozymes can then be used that will target the same sequence. Ribozymes are RNA molecules that possess RNA catalytic ability [see Cech for review] that cleave a specific site in a target RNA. The number of RNA molecules that are cleaved by a ribozyme is greater than the number predicted by stochiochemistry. [Hampel and Tritz, 1989; Uhlenbeck, 1987]. Therefore, the present invention also allows for the use of the ribozyme sequences targeted to the R2 or R1 mRNA sequences and containing the appropriate catalytic center. The ribozymes are made and delivered as discussed herein below. The ribozymes may be used in combination with the antisense sequences.

Ribozymes catalyze the phosphodiester bond cleavage of RNA. Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan, 1994; U.S. Pat. No. 5,225,347, columns 4–5). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). The ribozyme type utilized in the present invention is selected as is known in the art. Hairpin ribozymes are now in clinical trial and are the preferred type. In general the ribozyme is from 30–100 nucleotides in length.

Nuclease resistance, where needed, is provided by any method known in the art that does not substantially interfere with biological activity of the antisense oligodeoxynucleotides or ribozymes as needed for the method of use and delivery [Iyer et al., 1990; Radhakrishnan, et al., 1990; Eckstein, 1985; Spitzer and Eckstein, 1988; Woolf et al., 1990; Shaw et al., 1991]. Modifications that can be made to antisense oligonucleotides and ribozymes in order to enhance nuclease resistance include modifying the phosphorous or oxygen heteroatom in the phosphate backbone, short chain alkyl or cycloalkyl intersugar linkages or short chain heteroatomic or heterocyclic intersugar linkages. These include preparing methyl phosphonates, phosphorothioates, phosphorodithioates and morpholino oligomers. In one embodiment it is provided by having phosphorothioate bonds linking some or all the nucleotide bases. Phosphorothioate antisense oligonucleotides do not normally show significant toxicity at concentrations that are effective and exhibit sufficient pharmacodynamic half-lives in animals [Agarwal et al., 1996] and are nuclease resistant. Other modifications known in the art may be used where the biological activity is retained, but the stability to nucleases is substantially increased.

The present invention also includes all analogues of, or modifications to, an oligonucleotide of the invention that does not substantially affect the function of the oligonucleotide. Such substitutions may be selected, for example, in order to increase cellular uptake or for increased nuclease resistance as is known in the art. The term may also refer to oligonucleotides which contain two or more distinct regions where analogues have been substituted.

The nucleotides can be selected from naturally occurring or synthetically modified bases. Naturally occurring bases include adenine, guanine, cytosine, thymine and uracil. Modified bases of the oligonucleotides include xanthine, hypoxanthine, 2-aminoadenine, 6-methyl, 2-propyl and other alkyl adenines, 5-halo uracil, 5-halo cytosine, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines, 8-hydroxyl guanine and other substituted guanines, other aza and deaza adenines, other aza and deaza guanines, 5-trifluoromethyl uracil and 5-trifluoro cytosine.

In addition, analogues of nucleotides can be prepared wherein the structure of the nucleotide is fundamentally altered and that are better suited as therapeutic or experimental reagents. An example of a nucleotide analogue is a peptide nucleic acid (PNA) wherein the deoxyribose (or ribose) phosphate backbone in DNA (or RNA) is replaced with a polyamide backbone which is similar to that found in peptides. PNA analogues have been shown to be resistant to degradation by enzymes and to have extended lives in vivo and in vitro. Further, PNAs have been shown to bind stronger to a complementary DNA sequence than a DNA molecule. This observation is attributed to the lack of charge repulsion between the PNA strand and the DNA strand. Other modifications that can be made to oligonucleotides include polymer backbones, morpholino polymer backbones [U.S. Pat. No. 5,034,506], cyclic backbones, or acyclic backbones, sugar mimetics or any other modification including those that can improve the pharmacodynamics properties of the oligonucleotide.

The antisense oligonucleotides and ribozymes of the present invention can be synthesized by any method known in the art for ribonucleic or deoxyribonucleic nucleotides. For example, the oligonucleotides can be prepared using solid-phase synthesis such as in an Applied Biosystems 380B DNA synthesizer. Final purity of the oligonucleotides is determined as is known in the art.

The antisense oligonucleotides, ribozymes, and compounds identified using the methods of the invention modulate cell proliferation and in particular tumor cell proliferation. Therefore, pharmaceutical compositions and methods are provided for interfering with cell proliferation, preferably tumor cell proliferation comprising contacting tissues or cells with one or more of antisense oligonucleotides, ribozymes, and compounds identified using the methods of the invention. Preferably, an antisense oligonucleotide having SEQ ID Nos:1–102 and SEQ ID Nos:103–161 is administered.

The methods may be used to treat proliferative disorders including various forms of cancer such as leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, hematopoietic cancers, colon cancer, breast cancer, pancreatic cancer, head and neck cancers, and nervous system cancers, benign lesions such as papillomas, arthrosclerosis, psoriasis, primary and secondary polythemia, mastocytosis, autoimmune diseases, angiogenesis, bacterial infections, and viral infections, such as HIV infections, hepatitis or herpes infections.

The present invention provides pharmaceutical compositions of antisense oligonucleotides complementary to the ribonucleotide reductase R2 or R1 mRNA gene sequence or ribozymes as active ingredients for therapeutic application. These compositions can also be used in the method of the present invention. Where required the compounds are nuclease resistant. In general the pharmaceutical composition for modulating cell proliferation or for cytotoxicity in a mammal includes an effective amount of at least one antisense oligonucleotide as described above needed for the practice of the invention or a sequence segment thereof shown to have the same effect and/or ribozymes and a pharmaceutically physiologically acceptable carrier or diluent.

Antisense oligonucleotides of the invention have also been found to reduce metastasis (Table 13). In an embodiment of the invention, a method is provided for reducing metastasis in a subject comprising administering an amount of an antisense oligonucleotide of the invention effective to reduce metastasis. Most preferably the antisense oligonucleotide is SEQ ID Nos:1–102 and SEQ ID Nos:103–161.

In an embodiment the pharmaceutical composition for inhibiting tumorigenicity of neoplastic cells in a mammal consists of an effective amount of at least one active ingredient selected from antisense oligonucleotides complementary to the R2 mRNA, including the entire R2 mRNA or having short sequences as set forth in SEQ ID Nos:1–102 and a pharmaceutically physiologically acceptable carrier or diluent. In a preferred embodiment sequences in Table 12 are used. In a still further preferred embodiment SEQ ID Nos:1, 2, 12, 16, 18, 21, 25, 29, 34, 42, 44, 45, 46, 52, 53, 59, 60, 64, 65, 66, 68, 69, 70, 72, 73, 74, 76, 78, 79, 80, 90, 91, 92, 96, 99, 100, 102 can be used. Combinations of the active ingredients can be used.

The compositions can be administered orally, subcutaneously or parenterally including intravenous, intraarterial, intramuscular, intraperitoneally, and intranasal administration as well as intrathecal and infusion techniques as required by the malignant cells being treated. For delivery within the CNS intrathecal delivery can be used with for example an Ommaya reservoir or other methods known in the art. The pharmaceutically acceptable carriers, diluents, adjuvants and vehicles as well as implant carriers generally refer to inert, non-toxic solid or liquid fillers, diluents or encapsulating material not reacting with the active ingredients of the invention. Cationic lipids may also be included in the composition to facilitate oligonucleotide uptake. Implants of the compounds are also useful. In general the pharmaceutical compositions are sterile.

In the method of the present invention proliferating cells including neoplastic cells are contacted with a growth inhibiting amount of the bioactive antisense oligonucleotide for the R2 mRNA or a sequence segment (alternatively designated fragment) thereof shown to have substantially the same effect. In an embodiment the mammal to be treated is human but other mammalian species can be treated in veterinary applications.

The present invention provides a method of increasing sensitivity of neoplastic cells to chemotherapeutic drugs such as hydroxyurea [Ashihara and Baserga, 1979; McClarty et al., 1990]., N-(phosphonacetyl)-L-aspartate (PALA) and methotrexate (MTX). Patients who have tumors are treated with a noncytotoxic amount of at least one active composition including antisense oligonucleotides having a sequence corresponding to the sequence of the mRNA for the R2 component or sequence segments thereof and a chemotherapeutic drug. Utilizing this method the chemotherapeutic drug dose may be reduced to a noncytotoxic dose (either individual dose or treatment course) thereby reducing side effects. Alternatively, a cytotoxic dose of both the antisense oligonucleotide and chemotherapeutic drug are administered.

The present invention also provides a method of reducing the drug resistance (increasing sensitivity to the drugs) of neoplastic cells resistant to chemotherapeutic compounds such as hydroxyurea, N-(phosphonacetyl)-L-aspartate (PALA) and methotrexate (MTX). The method identifies patients who have tumors that are resistant to hydroxyurea, MTX, PALA or other chemotherapeutic drugs. These patients are then treated with a noncytotoxic amount of at least one active composition including antisense oligonucleotides having a sequence corresponding to the mRNA sequence for the R2 component or sequence segments thereof and the chemotherapeutic drug to which the cell is resistant. Alternatively, a cytotoxic dose of both the antisense oligonucleotide and chemotherapeutic drug are administered.

The synthetic antisense R2 oligonucleotides in an embodiment have the sequences as set forth in SEQ ID Nos:1–102. In a preferred embodiment sequences in Table 12 are used. In a still further preferred embodiment SEQ ID Nos:1, 2, 12, 16, 18, 21, 25, 29, 34, 42, 44, 45, 46, 52, 53, 59, 60, 64, 65, 66, 68, 69, 70, 72, 73, 74, 76, 78, 79, 80, 90, 91, 92, 96, 99, 100, 102 can be used.

By bioactive (expressible) is meant that the oligonucleotide is biologically active in the cell when delivered directly to the cell and/or is expressed by an appropriate promotor and active when delivered to the cell in a vector as described herein below. Nuclease resistance is provided by any method known in the art that does not substantially interfere with biological activity as described herein.

By contacting the cell, it is meant methods of exposing or delivery to a cell of antisense oligonucleotides or ribozymes whether directly or by viral or non-viral vectors and where the antisense oligonucleotide or ribozyme is bioactive upon delivery. The method of delivery will be chosen for the particular cancer being treated. Parameters that affect delivery can include the cell type affected and tumor location as is known in the medical art.

The treatment generally has a length proportional to the length of the disease process and drug effectiveness and the patient species being treated. It is noted that humans are treated generally longer than the Examples exemplified herein, which treatment has a length proportional to the length of the disease process and drug effectiveness. The doses may be single doses or multiple doses as determined by the medical practitioners and treatment courses will be repeated as necessary until diminution of the disease is achieved. Optimal dosing schedules may be calculated using measurements of drug accumulation in the body. Practitioners of ordinary skill in the art can readily determine optimum dosages, dosing methodologies, and repetition rates. Optimum dosages may vary depending on the relative potency of the antisense oligonucleotide, and can generally be determined based on ED., values in in vitro and in vivo animal studies and clinical trials. Variations in the embodiments used may also be utilized. The amount must be effective to achieve improvement including but not limited to decreased tumor growth, or tumor size reduction or to improved survival rate or length or decreased drug resistance or other indicators as are selected as appropriate measures by those skilled in the art.

Further, the pharmaceutical compositions utilized in the present invention are administered in combination with other drugs or singly, consistent with good medical practice such as cytotoxic agents, immunotoxins, alkylating agents, anti-metabolites, antitumor antibiotics and other anti-cancer drugs and treatment modalities that are known in the art. The composition is administered and dosed in accordance with good medical practice taking into account the clinical condition of the individual patient, the site and method of administration, scheduling of administration, and other factors known to medical practitioners. The "effective amount" for growth inhibition is thus determined by such considerations as are known in the art. The pharmaceutical composition may contain more than one embodiment of the present invention.

The nucleotide sequences of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell. Generally the construct contains the proper regulatory sequence or promotor to allow the sequence to be expressed in the targeted cell.

Once the oligonucleotide sequences are ready for delivery they can be introduced into cells as is known in the art. Transfection, electroporation, fusion, liposomes, colloidal polymeric particles and viral vectors as well as other means known in the art may be used to deliver the oligonucleotide sequences to the cell. Which method is selected will depend at least on the cells to be treated and the location of the cells and will be known to those skilled in the art. Localization can be achieved by liposomes, having specific markers on the surface for directing the liposome, by having injection directly into the tissue containing the target cells, by having depot associated in spatial proximity with the target cells, specific receptor mediated uptake, viral vectors, or the like.

As discussed herein, the present invention provides vectors comprising an expression control sequence operatively linked to the oligonucleotide sequences of the invention. The present invention further provides host cells, selected from suitable eucaryotic and procaryotic cells, which are transformed with these vectors as necessary. Such transformed cells allow the study of the function and the regulation of malignancy and the treatment therapy of the present invention.

Vectors are known or can be constructed by those skilled in the art and should contain all expression elements necessary to achieve the desired transcription of the sequences. Other beneficial characteristics can also be contained within the vectors such as mechanisms for recovery of the oligonucleotides in a different form. Phagemids are a specific example of such beneficial vectors because they can be used either as plasmids or as bacteriophage vectors. Examples of other vectors include viruses such as bacteriophages, baculoviruses and retroviruses, DNA viruses, liposomes and other recombination vectors. The vectors can also contain elements for use in either procaryotic or eucaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning: A Laboratory Manual,* Cold Springs Harbor Laboratory, New York (1989, 1992), in Ausubel et al., *Current Protocols in Molecular Biology,* John Wiley and Sons, Baltimore, Md. (1989), Chang et al., *Somatic Gene Therapy,* CRC Press, Ann Arbor, Mich. (1995), Vega et al., *Gene Targeting,* CRC Press, Ann Arbor, Mich. (1995),

*Vectors: A Survey of Molecular Cloning Vectors and Their Uses,* Butterworths, Boston Mass. (1988) and Gilboa et al (1986) and include, for example, stable or transient transfection, lipofection, electroporation and infection with recombinant viral vectors.

Introduction of the oligonucleotides of the present invention by infection offers several advantages over the other listed methods. Higher efficiency can be obtained due to their infectious nature. Moreover, viruses are very specialized and typically infect and propagate in specific cell types. Thus, their natural specificity can be used to target the vectors to specific cell types in vivo or within a tissue or mixed culture of cells. Viral vectors can also be modified with specific receptors or ligands to alter target specificity through receptor mediated events.

Recombinant methods known in the art can also be used to achieve the antisense inhibition of a target nucleic acid. For example, vectors containing antisense nucleic acids can be employed to express an antisense message to reduce the expression of the target nucleic acid and therefore its activity.

A specific example of DNA viral vector for introducing and expressing the antisense nucleotide sequence is the adenovirus derived vector Adenop53TK. This vector expresses a herpes virus thymidine kinase (TK) gene for either positive or negative selection and an expression cassette for desired recombinant sequences. This vector can be used to infect cells that have an adenovirus receptor which includes many cancers of epithelial origin as well as others. This vector as well as others that exhibit similar desired functions can be used to treat a mixed population of cells including, for example, an in vitro or ex vivo culture of cells, a tissue or a human subject.

Additional features can be added to the vector to ensure its safety and/or enhance its therapeutic efficacy. Such features include, for example, markers that can be used to negatively select against cells infected with the recombinant virus. An example of such a negative selection marker is the TK gene described above that confers sensitivity to the anti-viral drug gancyclovir. Negative selection is therefore a means by which infection can be controlled because it provides inducible suicide through the addition of antibiotic. Such protection ensures that if, for example, mutations arise that produce altered forms of the viral vector or sequence, cellular transformation will not occur. Features that limit expression to particular cell types can also be included. Such features include, for example, promoter and regulatory elements that are specific for the desired cell type.

Recombinant viral vectors are another example of vectors useful for in vivo expression of a desired nucleic acid because they offer advantages such as lateral infection and targeting specificity. Lateral infection is inherent in the life cycle of, for example, a retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. The vector to be used in the methods of the invention will depend on the desired cell type to be targeted. For example, if breast cancer is to be treated, then a vector specific for such epithelial cells should be used. Likewise, if cells of the hematopoietic system are to be treated, then a viral vector that is specific for blood cells and their precursors, preferably for the specific type of hematopoietic cell, should be used.

Retroviral vectors can be constructed to function either as infectious particles or to undergo only a single initial round of infection. In the former case, the genome of the virus is modified so that it maintains all the necessary genes, regulatory sequences and packaging signals to synthesize new viral proteins and RNA. Once these molecules are synthesized, the host cell packages the RNA into new viral particles which are capable of undergoing further rounds of infection. The vector's genome is also engineered to encode and express the desired recombinant gene. In the case of non-infectious viral vectors, the vector genome is usually mutated to destroy the viral packaging signal that is required to encapsulate the RNA into viral particles. Without such a signal, any particles that are formed will not contain a genome and therefore cannot proceed through subsequent rounds of infection. The specific type of vector will depend upon the intended application. The actual vectors are also known and readily available within the art or can be constructed by one skilled in the art using well-known methodology.

If viral vectors are used, for example, the procedure can take advantage of their target specificity and consequently, do not have to be administered locally at the diseased site. However, local administration may provide a quicker and more effective treatment, administration can also be performed by, for example, intravenous or subcutaneous injection into the subject. Injection of the viral vectors into a spinal fluid can also be used as a mode of administration, especially in the case of neuro-degenerative diseases. Following injection, the viral vectors will circulate until they recognize host cells with the appropriate target specificity for infection.

Transfection vehicles such as liposomes can also be used to introduce the non-viral vectors described above into recipient cells within the inoculated area. Such transfection vehicles are known by one skilled within the art.

The present invention contemplates a method of evaluating if a compound inhibits transcription or translation of a ribonucleotide reductase gene and thereby modulates (i.e. reduces) cell proliferation comprising transfecting a cell with an expression vector comprising a nucleic acid sequence encoding ribonucleotide reductase, the necessary elements for the transcription or translation of the nucleic acid; administering a test compound; and comparing the level of expression of the ribonucleotide reductase with the level obtained with a control in the absence of the test compound.

An expression vector comprising a nucleic acid sequence encoding ribonucleotide reductase may be constructed having regard to the sequence of the gene using procedures known in the art. Suitable transcription and translation elements may be derived from a variety of sources, including bacterial, fungal, viral, mammalian, or insect genes. Selection of appropriate elements is dependent on the host cell chosen, and may be readily accomplished by one of ordinary skill in the art.

Examples of reporter genes are genes encoding a protein such as β-galactosidase (e.g. lacZ), chloramphenicol, acetyl-transferase, firefly luciferase, or an immunoglobulin or portion thereof. Transcription of the reporter gene is monitored by changes in the concentration of the reporter proteins such as β-galactosidase etc. This makes it possible to visualize and assay for expression of recombinant molecules to determine the effect of a substance on expression of the ribonucleotide reductase gene.

Host cells suitable for carrying out the present invention include CHO, COS, BHK, 293 and HeLa. Protocols for the transfection of mammalian cells are well known in the art and include calcium phosphate mediated electroporation, and retroviral, and protoplast fusion-mediated transfection.

The present inventors have found that R2 interacts or cooperates with Raf-1 and/or Rac-1 thereby affecting the Ras signalling pathways. Therefore, the invention also contemplates a method for evaluating a compound for its ability to regulate a Ras signalling pathway by assaying for an agonist or antagonist (i.e. stimulator or inhibitor) of the interaction of R2 and Raf-1 and/or Rac-1. The basic method for evaluating if a compound is an agonist or antagonist of the interaction of R2 and Raf-1 and/or Rac-1, is to prepare a reaction mixture containing R2 and Raf-1 and/or Rac-1 under conditions which permit the interaction of R2 and Raf-1 and/or Rac-1, in the presence of a test compound. The test compound may be initially added to the mixture, or may be added subsequent to the addition of the R2 and Raf-1 and/or Rac-1. Control reaction mixtures without the test compound or with a placebo are also prepared. The formation of complexes or activation of the pathway is detected and the formation of complexes or activation of the pathway in the control reaction but not in the reaction mixture indicates that the test compound interferes with the interaction of R2 and Raf-1 and/or Rac-1. The reactions may be carried out in the liquid phase for R2 and Raf-1 and/or Rac-1, or the test compound may be immobilized.

The invention also makes it possible to screen for antagonists that inhibit the effects of an agonist of the interaction of R2 and Raf-1 and/or Rac-1. Thus, the invention may be used to assay for a compound that competes for the same binding site of R2.

The invention also contemplates methods for identifying compounds that bind to proteins that interact with R2 and thereby inhibit R2. Protein-protein interactions may be identified using conventional methods such as co-immunoprecipitation, crosslinking and co-purification through gradients or chromatographic columns. Methods may also be employed that result in the simultaneous identification of genes which encode proteins interacting with R2. These methods include probing expression libraries with labeled R2.

Two-hybrid systems may also be used to detect protein interactions in vivo. Generally, plasmids are constructed that encode two hybrid proteins. A first hybrid protein consists of the DNA-binding domain of a transcription activator protein fused to R2, and the second hybrid protein consists of the transcription activator protein's activator domain fused to an unknown protein encoded by a cDNA which has been recombined into the plasmid as part of a cDNA library. The plasmids are transformed into a strain of yeast (e.g. *S. cerevisiae*) that contains a reporter gene (e.g. lacZ, luciferase, alkaline phosphatase, horseradish peroxidase) whose regulatory region contains the transcription activator's binding site. The hybrid proteins alone cannot activate the transcription of the reporter gene. However, interaction of the two hybrid proteins reconstitutes the functional activator protein and results in expression of the reporter gene, which is detected by an assay for the reporter gene product.

It will be appreciated that fusion proteins may be used in the above-described methods. In particular, R2 fused to a glutathione-S-transferase may be used in the methods.

The compounds identified using the method of the invention include but are not limited to peptides such as soluble peptides including Ig-tailed fusion peptides, members of random peptide libraries and combinatorial chemistry-derived molecular libraries made of D- and/or L-configuration amino acids, phosphopeptides (including members of random or partially degenerate, directed phosphopeptide libraries), antibodies (e.g. polyclonal, monoclonal, humanized, anti-idiotypic, chimeric, single chain antibodies, fragments, (e.g. Fab, F(ab)$_2$, and Fab expression library fragments, and epitope-binding fragments thereof), and small organic or inorganic molecules. The compound may be an endogenous physiological compound or it may be a natural or synthetic compound.

The reagents suitable for applying the methods of the invention to evaluate compounds that modulate R2 and Raf-1 and/or Rac-1 interactions may be packaged into convenient kits providing the necessary materials packaged into suitable containers. The kits may also include suitable supports useful in performing the methods of the invention.

The compounds identified using the methods described herein, and other inhibitors of R2 expression described herein (e.g. antisense to R2) may be used for modulating a Ras pathway. In particular, the compounds may be used to inhibit the signal-transduction properties of Raf-1 and/or Rac-1; inhibit cell proliferation, alter the cell cycle, and downregulate the immune response in patients with autoimmune diseases. In an embodiment of the invention, the compounds have anti-oncogene or tumor suppressor activity.

EXAMPLES

The examples provide an analysis of malignancy related characteristics of cells containing deregulated R2 expression achieved by gene transfer techniques. Overexpression of R2 leads to an increased frequency of transformed foci formation by mouse fibroblasts following transfection with activated H-ras. In addition, expression of recombinant R2 in ras-transformed cells resulted in enhanced colony forming efficiency in soft agar, and markedly elevated tumorigenic and metastatic potential in vivo. Furthermore, deregulated R2 expression can cooperate with other oncogenes like rac-1 in mechanisms of transformation.

The results herein demonstrate for the first time that the R2 component of mammalian ribonucleotide reductase is a malignancy determinant that can synergize with activated oncogenes to modify malignant potential, and supports a model in which these effects are mediated through alterations in major Ras pathways that are brought about by deregulated R2 gene expression. The observations presented here indicate that R2 can also participate in other critical cellular functions, and can play a direct role in determining malignant potential through oncogene cooperativity.

The examples further demonstrate that ribonucleotide reductase R2 gene expression can play a significant role in determining drug sensitivity characteristics, and that this appears to occur at least in part through a mechanism involving genomic instability.

The mechanism through which aberrant R2 expression modifies drug sensitivities (Example 2) does not appear to require the direct involvement of p53 mutation or loss of wild type p53 function, although it is possible that genetic events downstream of a p53 regulated pathway are involved. As shown in Example 1 a relationship exists between increased R2 expression and activation of a ras pathway involving the Raf-1 protein and mitogen-activated protein kinase-2 (MAPK) activity. Recombinant R2 gene expression in Balb/c 3T3 and NIH-3T3 cells significantly increases both Raf-1 protein activation and mitogen-activating protein kinase (MAPK) activity.

A hypothesis for the above observations can be made, but it is not to be construed as limiting the present invention to this one mode of action. These observations imply that the R2 protein is capable of acting as a signal molecule in the MAPK pathway, in addition to its role as a rate-limiting component of ribonucleotide reduction. Transcription factors like the product of the c-myc gene are downstream targets of the MAPK pathway, and control for example, expression of cyclins A, D and E, which are important in the regulation of checkpoints during cell cycle progression [Hunter, 1995]. Compromising cell cycle checkpoint controls enhances genomic destabilization and facilitates DNA amplification [Kohn, 1996; Livingston et al., 1992]. c-myc overexpression has also been directly linked to gene amplification mechanisms involving DHFR [Mai, 1994]. These observations suggest that alterations in the MAPK pathway through aberrant R2 expression may be at least partly responsible for the observed changes in drug sensitivities and genomic integrity.

Examples 3–5 demonstrates that short antisense sequences directed against the R1 and R2 components have anti-tumor activity and are cytotoxic to the neoplastic cells. Further, the R2 antisense sequences can also act synergistically with well known chemotherapeutic agents. Very low concentrations (non-toxic) of short antisense sequences reduced the resistance of the neoplastic cells to chemotherapeutic agents such as N-(phosphonacetyl)-L-aspartate (PALA) and methotrexate (MTX) as well as hydroxyurea. As shown in the Example, cells were transfected with a vector containing the R2 sequence in an antisense orientation. These cells were more sensitive to the chemotherapeutic agents. Also, mouse 10T½ cells which are drug resistant, when transfected with R2 sequence in the antisense orientation, were found to have significantly reduced resistance (increased sensitivity) to the chemotherapeutic agents. Short synthetic antisense sequences complementary to the R2 sequence also provided increased sensitivity.

The above discussion provides a factual basis for the use of antisense oligonucleotides and ribozymes directed against the R2 mRNA. The methods used with and the utility of the present invention can be shown by the following non-limiting examples and accompanying figures.

General Methods
General Methods in Molecular Biology

Standard molecular biology techniques known in the art and not specifically described were generally followed as in Sambrook et al., *Molecular Cloning: A Laboratory Manual,* Cold Springs Harbor Laboratory, New York (1989, 1992); in Ausubel et al., *Current Protocols in Molecular Biology,* John Wiley and Sons, Baltimore, Md. (1989); and in Perbal, *A Practical Guide to Molecular Cloning,* John Wiley & Sons, New York (1988). Polymerase chain reaction (PCR) was carried out generally as in *PCR Protocols: A Guide To Methods And Applications,* Academic Press, San Diego, Calif. (1990).

Vectors can be constructed for the present invention by those skilled in the art and should contain all expression elements necessary to achieve the desired transcription of the sequences. The expression elements can be selected to allow expression only in the cell being targeted. Other beneficial characteristics can also be contained within the vectors such as mechanisms for recovery of the nucleic acids in a different form. One of ordinary skill in the art will know which expression elements are compatible with a particular cell type. The vectors can be introduced into cells or tissues by any one of a variety of known methods within the art as described herein above.

General Methods in Immunology

Standard methods in immunology known in the art and not specifically described were generally followed as in Stites et al.(eds), Basic and Clinical Immunology (8th Edition), Appleton & Lange, Norwalk, Conn. (1994) and Mishell and Shiigi (eds), Selected Methods in Cellular Immunology, W.H. Freeman and Co., New York (1980).

Assays for Tumorigenicity and Metastasis

Malignancy potential was determined as reported previously [Wright, 1989a; Egan et al., 1987a, 1987b; Damen et al., 1989; Taylor et al., 1992; Stokoe et al., 1994]. Six to eight week old C3H/HeN syngeneic mice (Charles River, Quebec) were used to evaluate tumorigenic and metastatic potential of the cells. Cells were prepared from subconfluent, logarithmically growing cultures, collected by gentle treatment with trypsin/EDTA solution and adjusted to appropriate concentration in a balanced salt solution.

For the tumorigenicity (tumor latency) assay, $1 \times 10^5$ cells in a 0.1 ml volume were injected subcutaneously into the back of mice and the time required to form a tumor ($2 \times 2$ mm) detectable by palpation was recorded. The growth of tumors was also evaluated by measuring tumor diameters, and estimating tumor base area each day following tumor appearance [Damen et al., 1989]. Tumor size was determined by multiplying the dimensions of the cross-section of the tumor. Tumors were removed from the mice and tumor weight was recorded 21 days later. In the case of no tumor formation, mice were kept for 2 months after injection and then sacrificed.

For experimental metastasis assays (determination of metastatic potential), $1 \times 10^5$ cells in a 0.2 ml volume were injected into the tail veins of 6–8 week old C3H/HeN syngeneic mice and an estimate of the number of lung tumors was made 21 days later. The mice were sacrificed, and the lungs were stained by injecting Bouin's solution {picric acid, formaldehyde, acetic acid (15:5:1)} intratracheally [Egan et al., 1987b; Damen et al., 1989]. Pulmonary tumors were counted with the aid of a dissecting microscope. To confirm that equal numbers of test and control cells were injected, duplicate culture plates containing growth medium were inoculated with 100 cells per plate. After 10 days in culture, plates were stained with methylene blue and colonies were scored.

Ribonucleotide Reductase Assay

Ribonucleotide reductase activity in crude extracts prepared from cells is assayed as previously described [Lewis et al., 1978; Hurta and Wright, 1992; Hurta et al., 1995]. Enzyme preparations are obtained from logarithmically growing cells lysed in phosphate buffered saline, pH 7.2, containing 1 mM dithiothreitol and 1 mM protease inhibitor, AEBSF (Calbiochem, San Francisco, Calif.), by three cycles of freeze-thawing. Following centrifugation, the supernatant is used for enzyme activity assays with [$^{14}$C]-CDP (Moravek Biomedical, Brea, Calif.), as detailed previously [Lewis et al., 1978; Hurta and Wright, 1992; Fan et al., 1996a; Choy et al, 1988].

Western Blot Analysis

The procedures used have been reported [Fan et al., 1996a; 1996b; Choy et al, 1988]. Briefly, following cell extract preparation, total protein content was determined, and an aliquot was analyzed on 10% linear SDS-polyacrylamide gel. After protein transfer and blocking, membranes were incubated with anti-R2 rabbit polyclonal antibody. Alkaline phosphatase conjugated goat anti-rabbit IgG (Sigma) was used for protein R2 detection.

EXAMPLE 1

R2 Cooperates With Activated Oncogenes

To determine the malignant potential of deregulated expression of the rate-limiting R2 component of ribonucleotide reductase, the properties of cells stably infected with a retroviral expression vector (SH/mR2) carrying the R2 component [Fan et al., 1996b], were investigated. Further the interaction between R2 and activated oncogenes was explored.

Materials and Methods
Expression Vectors

The retroviral expression vector for the human Myc epitope-tagged mouse R2 component, SH/mR2, was constructed and packaged as described in Fan et al [1996b]. The infectivity of the viral stock was $\geq 1 \times 10^4$ colony-forming units/ml. Plasmid pH06Ti which expresses T-24 H-ras and a selective marker neo was used for malignant transformation [Egan et al., 1987a, 1987b; Taylor et al., 1992]. The activated Rac-1 plasmid (V12 Rac-1) was kindly provided by M. Symons [Stokoe, et al., 1994].

Cells and Cell Culture

The mouse cell lines, BALB/c 3T3, NIH 3T3, four lines of T24 H-ras transformed 10T½cells, named C1, NR4, r-2 and r-3 have been previously used as recipients of the R2 retroviral vector [Fan et al., 1996b]. Cells were routinely cultured in α-minimal essential medium (α-MEM)(Gibco, Grand Island, N.Y.) supplemented with 10% calf serum (Fetalclone III, Hyclone, Logan, Utah). Infection of cells with SH/mR2 or control virus LXSH in the presence of polybrene was carried out [Miller et al, 1993], and stable infectants ($\geq 1 \times 10^4$ clones) were obtained with hygromycin selection and pooled [Fan et al., 1996b; Miller et al, 1993]. Determinations of cell division times, plating efficiencies, and relative sensitivities to hydroxyurea cytotoxicity by estimating relative colony forming efficiencies, were carried out as previously described [Lewis et al., 1978; Egan et al., 1987a; Hards and Wright, 1981].

Growth in soft agar was estimated in 10 cm tissue culture plates containing 15 ml base agar (0.5% Bactoagar in α-MEM plus 10% calf serum) and 10 ml of growth agar (0.33% agar in α-MEM containing 10% calf serum). Cells were obtained from subconfluent cultures, and colonies were scored 10–15 days later [Egan et al., 1987a, 1987b; Hards and Wright, 1981]. Transformation was also analyzed by determining focus formation after cells were infected with SH/mR2 or LXSH or transfected with T-24 Ras or V12 Rac-1 plasmids by calcium phosphate precipitation [Taylor et al, 1992]. At 40 hours after infection or transfection, cells were split into three 10 cm tissue culture plates which were provided daily with 20 ml of fresh complete medium (α-MEM plus 10% calf serum) for 10–14 days, stained with methylene blue and foci were scored [Taylor et al, 1992]. The transfection frequency in all the experiments were routinely determined by cotransfection of a mammalian expression plasmid for β-galactosidase from *Esherichia coli*, with the T-24 Ras or V-12 Rac-1 plasmids, followed by treatment of cells with the X-gal and counting the number of blue cells [Price et al, 1987]. In some cases, T-24 Ras plasmid transfected plates were selected with geneticin, and drug resistant colonies were scored approximately 14 days later by staining with methylene blue.

Assays for Tumorigenicity and Metastasis

Malignant potential was determined as described herein above.

Protein R2 Analysis

The procedures for Western blot analysis have been described previously, for example, using either the anti-myc mouse monoclonal 9E10 antibody (ATCC, Rockville, Md.) [Fan et al., 1996b] or the anti-R2 rabbit polyclonal antibody [Chan et al., 1993]. To determine recombinant R2 protein expression during the cell cycle, flow cytometry analysis was performed following 9E10/fluorescein isothiocyanate antibody labelling as previously described [Blosmanis et al, 1987; Chadee et al, 1995].

Determination of Membrane-associated Raf-1 Protein

The membrane fraction was prepared as described by Qui et al. [1995], and used for Western analysis with a polyclonal antibody specific for Raf-1 protein (Santa Cruz Biotechnology Inc., Santa Cruz, Calif.), after the protein content was determined by the standard Bio-Rad assay. Densitometry analysis of the Raf-1 band was performed, and the amount of Raf-1 protein from each sample was corrected by densitometry analysis of a well separated band on a parallel gel stained with Coomassie blue.

Ribonucleotide Reductase Assay

The Assay was performed as described herein above. In some experiments enzyme assays were performed by combining purified recombinant R1 protein [Salem et al, 1993] with 9E10 antibody-precipitated R2 protein [Hurta and Wright, 1992]. In this Example, 20 µg of the 9E10 antibody and 50 µl of Staphylococcal protein A-agarose (Sigma Chem. Co., St. Louis, Mo.) were added to 1 ml of the supernatant of centrifuged lysed cells, and placed on a rocker at 4° C. for 2 hours. The Staphylococcal protein A agarose-immunocomplex was washed three times with 1 ml of cold phosphate buffer containing 1 mg/ml bovine serum albumin. The immunocomplex was then assayed for ribonucleotide reductase activity [Lewis et al, 1978; Hurta and Wright, 1992; Fan et al., 1996b; Choy et al, 1988].

Assay of MAPK Activity

Cultures with $\geq 90\%$ confluency were stressed in serum-free medium [Stokoe et al., 1994; Jelinek et al, 1994] and extracted as previously described [Alessi et al., 1995]. MAPK-2 protein was immunoprecipitated by agarose beads conjugated with non-neutralizing antibody for the protein (Santa Cruz Biotechnology, Inc.), and the kinase activity of the immunocomplex was assayed by measuring its ability to phosphorylate myelin basic protein using a MAPK assay kit from Upstate Biotechnology, Inc. (Lake Placid, N.Y.).

Results

Expression of Biologically Active R2 Protein

Figure 1B:
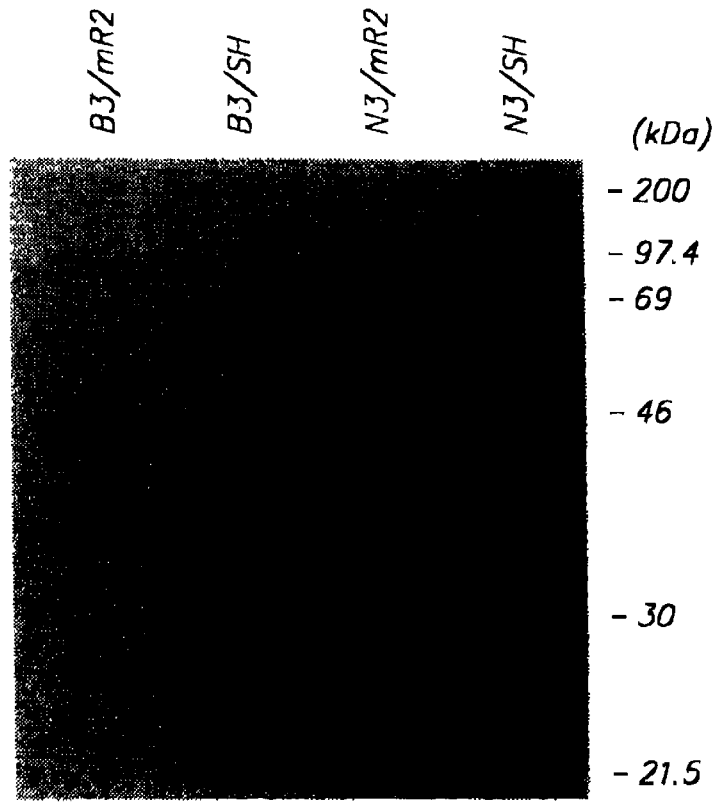

To determine the malignant potential of deregulated expression of the rate-limiting R2 component of ribonucleotide reductase, the properties of cells stably infected with a retroviral expression vector (SH/mR2) carrying the R2 component [Fan et al., 1996b], were investigated. The use of this expression vector allowed high infection efficiency and stable expression of the R2 protein. To distinguish the vector gene product from the endogenous R2, a human c-Myc epitope coding for 10 amino acids plus methionine was added to the 5'-end of the R2 cDNA. FIG. 1A shows that Western blots with the 9E10 antibody that specifically recognizes the Myc-epitope sequence detects the R2 protein of approximately 45 kDa in SH/mR2 stably infected BALB/c 3T3 and NIH 3T3 cells (named B3/mR2 and N3/mR2, respectively), but not in control vector (LXSH) infected B3/SH or N3/SH cells. R2 specific antibodies detected the endogenous as well as the recombinant R2 protein in expression vector infected cells, and as expected only the endogenous protein was observed in control vector infected cells (FIG. 1B).

Figure 1C:
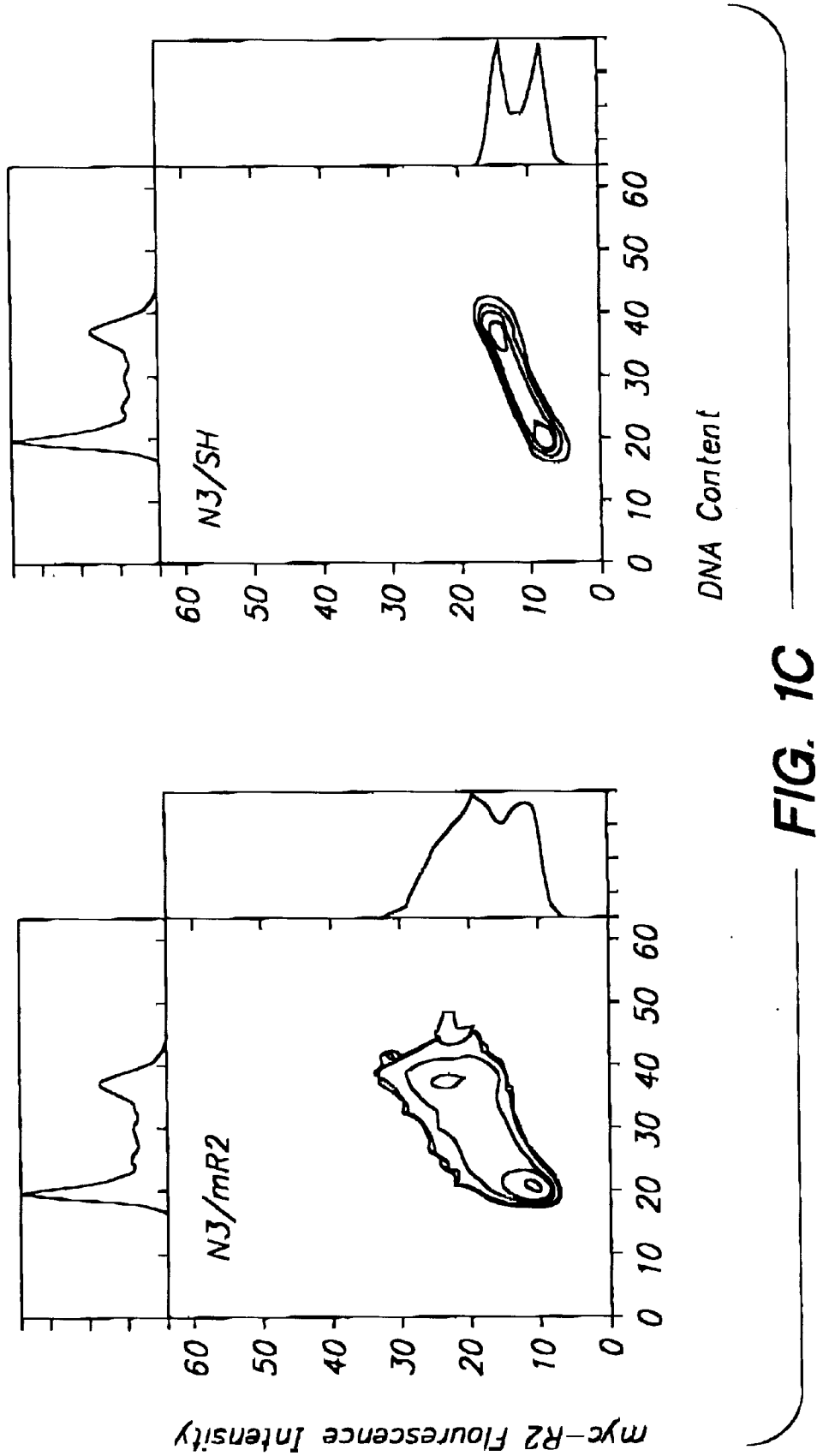

Flow cytometry analysis following 9E10/fluorescein isothiocyanate antibody labelling demonstrated that the recombinant R2 protein was constitutively expressed throughout the cell cycle (FIG. 1C). Indirect microscopic analysis using the 9E10 antibody indicated that essentially every cell in the B3/mR2 and N3/mR2 populations expressed the Myc-tagged R2 protein.

Several experiments were performed to demonstrate that the vector-expressed R2 is biologically active. First, B3/mR2 and N3/mR2 cells were observed to be resistant in colony-forming experiments to the cytotoxic effects of hydroxyurea, an inhibitor of the R2 protein [Wright, 1989a; 1989b], when compared to B3/SH and N3/SH cells [Fan et al., 1996b]. Second, ribonucleotide reductase activity was assayed and found that the CDP reductase activities in B3/mR2 and N3/mR2 cells in three independent experiments were 1.96±0.32 and 1.71±0.11 nmoles/mg protein/hour, respectively, which was 2.6 and 2.1 times higher than observed with B3/SH and N3/SH cells (0.74±0.14 and 0.83±0.08 nmoles/mg/hour, respectively). Finally, enzyme assays were carried out by combining purified recombinant R1 protein [Salem et al, 1993], with 9E10 antibody precipitated R2 protein. Significant levels of activity (15 to 20 nmoles/mg/hr.) were detected when B3/mR2 and N3/mR2 cells were used as a source for Myc-tagged R2, and as expected no activity was found when B3/SH or N3/SH cells were used.

Ras Transformation Potential Determined by Aberrant R2 Gene Expression

The above results indicate that cells can be altered in the regulation of biologically active R2 protein. Therefore, altered R2 expression was tested to see if it further transformed cells like BALB/c 3T3 or NIH 3T3. Similar to control B3/SH and N3/SH cells, as well as the parental non-infected lines, B3/mR2 and N3/mR2 cultures remained in a flat, non-transformed morphology on tissue culture plates, and exhibited contact and density inhibited growth (data not shown). No transformed foci were observed with BALB/c 3T3 or NIH 3T3 cells after infection with the retroviral SH/mR2 vector (FIG. 2A, a and b).

Figure 2C:
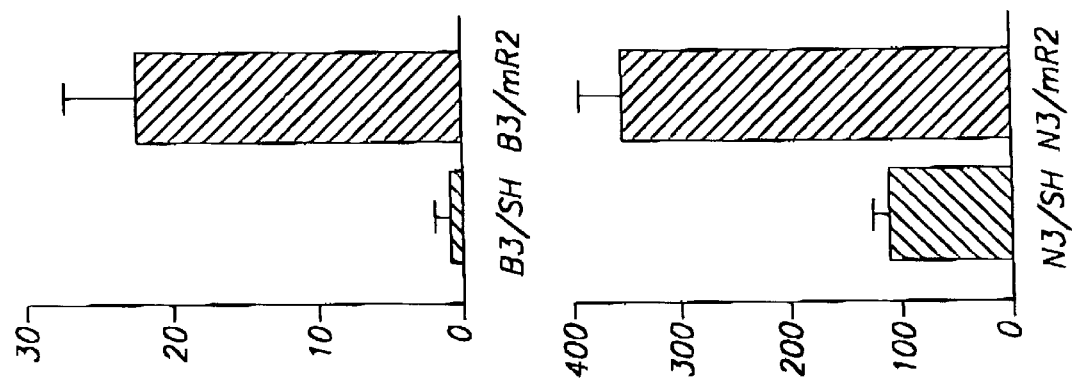

The results suggest that deregulation of R2 gene expression does not on its own transform BALB/c 3T3 or NIH 3T3 fibroblasts. To test the hypothesis that deregulated R2 expression may cooperate with oncogenes line H-ras, an expression plasmid containing T24 H-ras was transfected into established recombinant R2 expressing cell populations derived from BALB/c 3T3 or NIH 3T3. A consistent and significant increase (3.4 fold) in the number of foci formed with H-ras transfected N3/mR2 cells was observed when compared to N3/SH control cells (FIG. 2B, c and d and FIG. 2C). An even more marked increase of about 70 fold was observed when H-ras transfected B3/mR2 cells were compared to B3/SH cells (FIG. 4B, a and b and FIG. 2C). This occurred even though the transfection efficiency with N3/mR2 and B3/mR2 cells as determined by scoring G418 selected colonies, and/or counting blue cells following cotransfection of H-ras with an expression plasmid for $E.$ $coli$ β-galactosidase [Price et al., 1987], were actually lower (by about 50%) than with N3/SH and B3/SH cells.

Ras Malignancy Potential Determined by Aberrant R2 Gene Expression

Since combinations of altered R2 gene expression and activated H-ras were synergistic in focus forming experiments in which ras was transfected into altered R2 expressing cells, this gene combination was tested further by infecting four independent H-ras transformed 10T½ cell lines, C1, NR4, r-2 and r-3 that were previously characterized [Egan et al., 1987a, 1987b; Taylor et al., 1992; Stokoe et al., 1994], with the retroviral vector SH/mR2. Stable infectants were selected with hygromycin, and Western blot analyses and enzyme activity assays confirmed that these infectants expressed biologically active Myc-tagged R2 protein.

Soft agar growth experiments revealed that H-ras transformed cells containing the recombinant R2 sequence were much more efficient at producing colonies in semi-solid growth agar than the uninfected parental populations (e.g. r-3) or control vector infected cells (C1, NR4, r-2) (Table 1). In addition, many of the colonies formed by cells infected with recombinant R2 were larger in size (FIG. 3A). Since each pair of recombinant R2 expressing and control cell populations have almost identical growth rates (12.9 hours for C1/SH and 12.2 hours for C1/mR2, 13.5 hours for r-2/SH and 13.9 hours for r-2/mR2, 11.6 hours for r-3 and 11.9 hours for r-3/mR2, 14.1 hours for NR4/SH and 14.3 hours for NR4/mR2), plating efficiencies (58% for C1/SH and 55% for C1/mR2, 59% for r-2/SH and 63% for r-2/mR2, 91% for r-3 and 88% for r-3/mR2, 73% for NR4/SH and 75% for NR4/mR2), and cell cycle phase distributions (data not shown) when grown on solid surfaces, the alterations observed in soft agar and in foci forming experiments suggest that a combination of deregulated R2 expression and activated H-ras may lead to greater malignant potential in vivo.

Therefore, the tumorigenic and metastatic potential of C1/mR2 and C1/SH cells was compared in syngeneic C3H/HeN mice. Marked differences in malignant potential were observed. C1/mR2 cells exhibited shorter tumor latency and greater tumor growth when compared to C1/SH cells (FIG. 3B). Furthermore, metastasis assays clearly indicated that C1/mR2 cells were more malignant than C1/SH cells and produced significantly more lung tumors (FIG. 3C).

R2 Gene Expression and Oncogene Cooperativity

The above results indicate that altered R2 expression can cooperate with activated H-ras in in vitro transformation and in in vivo malignancy assays. Since no obvious differences in growth rates or cell cycle phase distributions were found that may account for this cooperation, as for example changes in cell cycle regulation, the following idea was tested. Does deregulated R2 expression synergize with ras by elevating the activity of a Ras signal pathway? This would be consistent with studies showing a direct correlation between ras expression and malignant potential [Egan et al., 1987a, 1987b; Wright et al, 1993; Bradley et al, 1986]. A major Ras pathway for regulating gene expression involves the Raf-1 protein kinase. Activated Ras recruits Raf to the plasma membrane where Raf and downstream signalling molecules like MAPKs become activated [Stokoe et al, 1994; Jelinek et al, 1994; Leevers et al, 1994].

Using a Raf-1 specific antibody, the levels of membrane associated Raf-1 in six BALB/c 3T3, NIH 3T3 and 10T½ derived cell lines containing deregulated R2 expression were compared with control cells containing only endogenous R2 protein (FIG. 4A). In all six cases, cell lines containing deregulated R2 showed increased membrane associated Raf-1, with an average increase of about 30% which was highly significant (p<0.001). In agreement with the above observation, cell lines with deregulated R2 expression exhibited a consistent and significant increase of about 70% (p<0.001) in MAPK-2 activity (FIG. 4B). Oncogenic Ras also activates the Rac pathway which is parallel to the Raf pathway, and therefore constitutively active Rac-1 cooperates with membrane-targeted Raf-1 in malignant transformation [Qiu et al, 1995].

If MAPK activation mediated by Raf-1 translocation and activation is important in the R2/ras synergism described herein above in this Example, then aberrant R2 expression should cooperate with activated Rac-1 in cellular transformation, because it has been shown previously that activated Raf-1 and Rac-1 cooperate in mechanisms of transformation [Qiu et al, 1995]. FIG. 4C shows that this prediction is correct, since positive cooperation in transformation between activated Rac-1 and R2 was observed in a manner similar to Ras and R2, as measured by focus formation with N3/mR2 and N3/SH cells transfected with activated V12 Rac-1 [Qiu et al, 1995]. These observations are consistent with the view that deregulated R2 gene expression cooperates with oncogenes like ras and rac by upregulating Raf translocation and MAPK pathway activity, but they do not rule out the possibility that other transduction pathways involving activated Raf may also be involved, since there is evidence that Raf can regulate some cellular activities through MAPK-independent pathway(s) [Lenormand et al, 1996; Koong et al, 1994; Agarwal et al, 1995].

This Example indicates for the first time that the R2 component of mammalian ribonucleotide reductase is a novel malignancy determinant that can synergize with activated oncogenes to modify malignant potential. It is important to note that the only role ascribed to R2 in the cell prior to this Example is as a rate-limiting component of ribonucleotide reductase. This Example demonstrates that R2 can also participate in other critical cellular functions and can play a direct role in determining malignant potential through oncogenic cooperativity.

EXAMPLE 2

R2 Gene Expression And Changes In Drug Sensitivity And Genome Stability

Materials and Methods
Cell Lines and Culture Conditions

The hydroxyurea resistant mouse cell lines, H-2, H-4, LHF and SC2 were derived from mouse L cells and have been characterized in Choy et al [1988] and McClarty et al [1988]. BALB/c 3T3 cells were used as recipients of an R2 retroviral expression vector (B3/mR2 and B3/R2c2 cell lines), or of the same retroviral vector lacking the R2 sequence (B3/SH cells)[Fan et al., 1996a; 1996b]. NIH-3T3 cells were also used as recipients of the R2 retroviral expression vector (N/R2-4 cell line) or of this retroviral vector lacking the R2 sequence (N/SH cells), as described previously [Fan et al., 1996a; 1996b]. The N/R2+ASR2 cell line was the recipient through co-transfection using LipofectAmine (Life Technologies, New York) [Damen et al., 1991] of retroviral vectors containing the R2 coding sequence and the R2 sequence in the antisense orientation. RP3 and RP6 cells are 10 T ½ mouse cell lines that have been transfected with the T-24 H-ras oncogene and a mutant oncogenic form of the p53 gene [Taylor et al., 1992], and they were also used as recipients through transfection using LipofectAmine reagent, a retroviral vector containing the R2 coding region in an antisense orientation [Fan et al., 1996b], to obtain RP3/ASR2 and RP6/ASR2 cells. 1B cells are p53$^{-/-}$ and were derived from embryonic fibroblasts [Lowe et al., 1994]. All cells were cultured in α-minimal essential medium (Gibco, Grand Island, N.Y.) containing 10% fetal bovine serum (Intergen, Purchase, N.Y.) and antibiotics (100 units/ml penicillin and 100 μg/ml streptomycin) at 37° C. in a humidified atmosphere containing 5% $CO_2$.

Drug Selections

Cells ranging in numbers from 500 to 1–2×10$^5$ were added to 100 mm tissue culture plates in growth medium containing 10% dialyzed fetal bovine serum, and in the absence or presence of drug [Huang et al., 1995a; Choy et al., 1988]. The culture medium was replaced with fresh medium every week for two to three weeks. Surviving cells were visualized by methylene blue staining, and colonies of about 50 cells or more were scored [Huang et al., 1995a]. The relative colony forming efficiency was defined as the ability to produce colonies in the presence of a drug divided by that ability in the absence of drug.

Assay for Gene Amplification

Genomic DNA was extracted from logarithmically growing cells by the phenolchloroform extraction method [Blin and Stafford, 1976], and potential gene amplification events were determined by Southern blot analysis as described [Huang et al., 1995a; Choy et al., 1988], using the cDNA fragments as probes noted below. The pCAD142 plasmid containing CAD cDNA, which encodes the CAD protein complex [Shigesada et al., 1985], was used to obtain the 6.3 Kb Hind III fragment as a probe. The pLTR DHFR26 plasmid containing the mouse dihydrofolate reductase gene [Chang et al., 1978], provided the 1.3 Kb Bam H1 fragment as a probe. The 1487 bp Sal I/Pst I probe for ribonucleotide reductase R2 was prepared from cDNA clone 10 [Huang et al., 1995a; Choy et al., 1988].

Electrophoretic Gel Mobility Shift Assay (EMSA)

EMSA was used to determine the presence of wild type p53. Assays were performed essentially as described [Price and Calderwood, 1993], with the following modifications. Cells on 150 mm plates were washed once with ice cold phosphate buffered saline (PBS) and scraped into 1 ml PBS. Cells were pelleted by centrifugation at 1300 g at 4° C. for 10 minutes and stored at −80° C. Nuclei were prepared by lysing the pellets in 300 μl buffer A (20 mM HEPES {pH 7.6}, 20% glycerol, 10 mM NaCl, 1.5 mM $MgCl_2$, 0.2 mM EDTA and 0.1% Triton X-100) for 20 minutes on ice. Buffer A also contained 1 mM phenylmethylsulfonyl fluoride (PMSF) and 10 mM dithiothreitol (DTT). Nuclei were isolated by centrifugation at 1300 g at 4° C. for 10 minutes. Nuclear lysates were prepared by adding 20–40 μl of buffer A containing 500 mM NaCl, 1 mM PMSF and 10 mM DTT to the nuclear pellet and incubating 20 minutes on ice. The extracted nuclei were pelleted by centrifugation at 16,000 g at 4° C.; the supernatant was removed and an aliquot was used for protein determination using the Biorad protein assay procedure (Biorad).

The nuclear lysate was incubated with an excess of double stranded p53 consensus binding sequence (GGACATGCCCGGGCATGTCC)(SEQ ID No:162) end labeled with [γ-$^{32}$P]-ATP using T4 polynucleotide kinase (Boehringer). DNA binding was carried out in buffer containing 20 mM HEPES (pH 7.6), 20% glycerol, 1.5 mM $MgCl_2$, 0.2 mM EDTA, 1 mM PMSF and 10 mM DTT. Each binding reaction contained 5 μg cell lysate, 10 μg double stranded poly (dI-dC) (Pharmacia), 1.4 ng labeled consensus probe and 100 ng of monoclonal antibody 421 (Santa Cruz) in a total volume of 20 μl. DNA binding was allowed to proceed for 30 minutes at room temperature and the mixture was separated by electrophoresis on 5% nondenaturing polyacrylamide gels. Electrophoresis was carried out at room temperature until the xylene cyanol tracking dye had run to the bottom of the gel and the free probe had run off the gel.

Statistical Analysis

Analysis of covariance was used to compare dose response data between groups of different cell lines, with the significance level set at $\alpha=0.05$ [Huang et al., 1995a].

Results

Hydroxyurea Resistant Cell Lines with Decreased Sensitivity to Non-selective Drugs H-2, H-4, LHF and SC2 are mouse L cell lines selected for resistance to the cytotoxic effects of the antitumor agent, hydroxyurea. These four cell lines exhibited resistance to hydroxyurea in colony forming efficiency experiments, that ranged between approximately 18 (H-2) to 30 (SC2) fold higher than the wild type mouse L cell line from which they were derived [Choy et al., 1998; McClarty et al., 1988]. They also contained elevated levels of ribonucleotide reductase activity that ranged between 2.2 fold (H-2) to 17 fold (LHF and SC2), which was primarily due to increases in the R2 component of ribonucleotide reductase that is limiting for enzyme activity and cell division in proliferating mouse cells. Table 2 shows that the four hydroxyurea resistant cell lines were also less sensitive to the cytotoxic effects of N-(phosphonacetyl)-L-aspartate (PALA) and methotrexate (MTX) in colony forming experiments, when compared to parental wild type mouse L cells. These differences in drug sensitivity are highly significant, with p values of <0.0001 for each of the cell lines when compared to the parental wild type mouse cells.

Figure 5A:
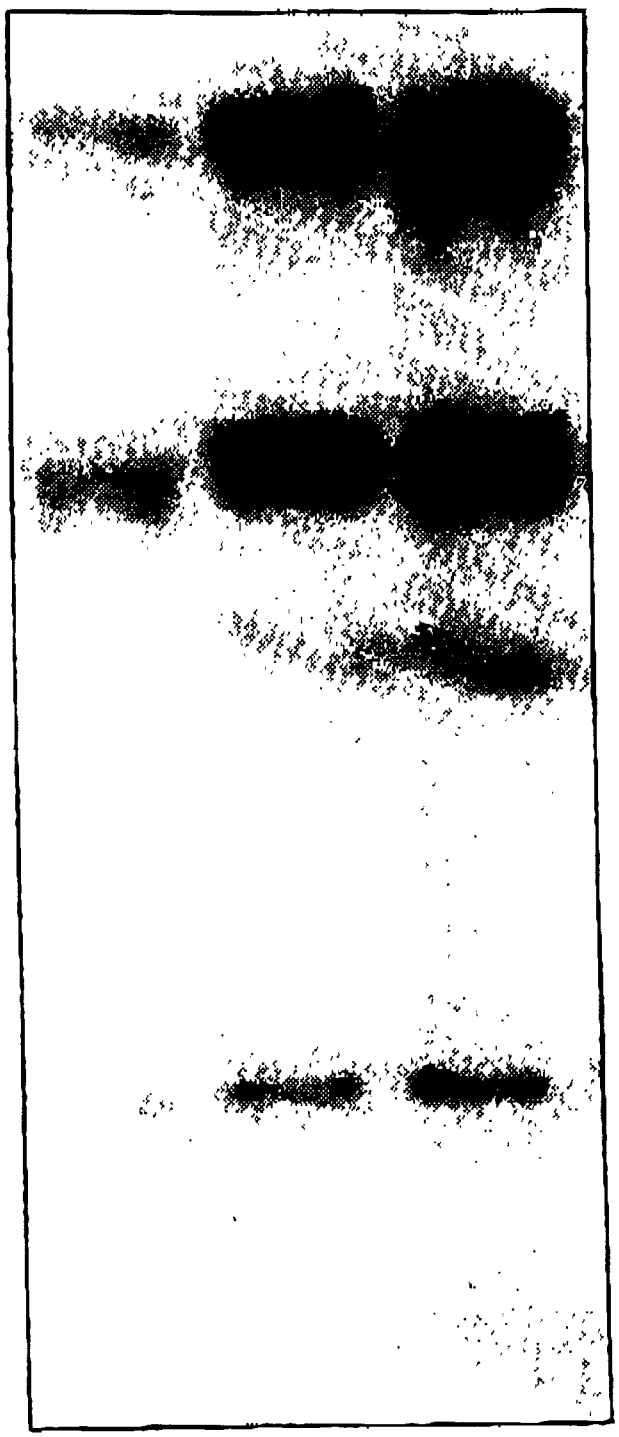
FIG. 5A–B are photographs of gels showing examples of Southern blot analysis of CAD (A) and DHFR (B) DNA with mouse L cells. (A) H-4 cells not exposed to drug as a control (a), H-4 cells from a colony that developed in the presence of 50 µM PALA (b), or in the presence of 60 µM PALA (c). DNA was digested to completion with Xba1. (B) SC2 cells not exposed to drug as a control (a), SC2 cells from colonies that developed in the presence of 80 nM methotrexate (MTX) (b) and (c). DNA was digested to completion with Pst1.
Figure 5B:
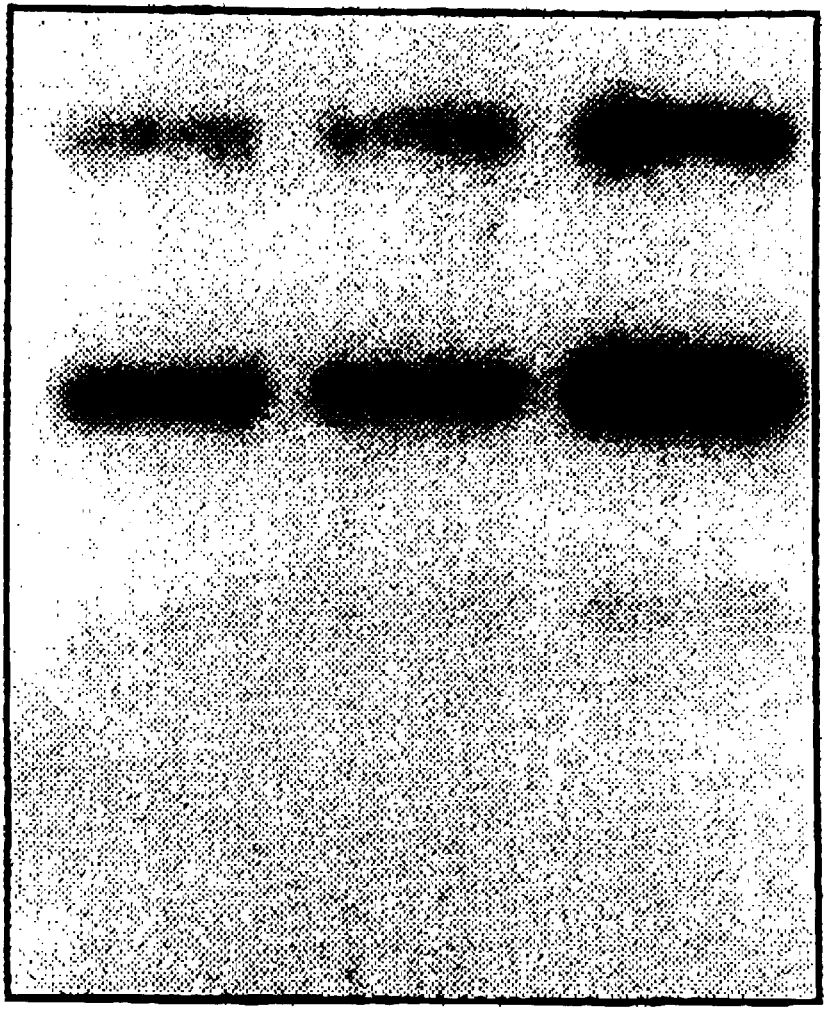

Although many mechanisms responsible for drug resistance have been described [Wright, 1989; Kohn, 1996], resistance to MTX and PALA are frequently accompanied by increased levels of the drug targeted gene products, dihydrofolate reductase (DHFR) or CAD (a multifunctional polypeptide containing carbamyl phosphate synthetase, aspartate transcarbamylase and dihydroorotase) respectively, and this often occurs through a mechanism of gene amplification [Huang et al., 1995a; Livingston et al., 1992; Yin et al., 1992; Mai, 1994; Stark, 1993]. Indeed, the principal and perhaps only mechanism for PALA resistance in mouse cells occurs via CAD gene amplification [Stark, 1993]. Therefore, colonies that developed in the presence of normally cytotoxic concentrations of these two drugs were examined for possible gene amplification events. FIG. 5 shows that cells that proliferated in the presence of PALA or MTX exhibited increased CAD or DHFR gene copy numbers. In keeping with previous studies [Stark, 1993; Huang et al., 1995b; Otto et al., 1989; Stark et al., 1990], all colonies that developed in PALA and tested (10/10) showed CAD gene amplification. Also as previously reported [Huang et al., 1995b], some but not all colonies that developed in the presence of MTX (3/6) showed DHFR gene amplification.

Direct Test for a Relationship Between R2 Gene Expression and Decreased Drug Sensitivity Since hydroxyurea resistant mouse cells contain other biochemical alterations in addition to changes in ribonucleotide reductase [Wright et al., 1989], the relationship between drug sensitivity and increased R2 levels was directly tested with cells containing a retroviral expression vector encoding the mouse R2 sequence, and cells containing the same retroviral vector but lacking the R2 sequence. B3/mR2 is a population of BALB/c 3T3 cells containing elevated R2 protein due to the presence of a retroviral expression vector encoding R2, and B3/SH is a cell population that has wild type levels of R2 protein and contains the empty vector as a control. B3/R2c2 is a cloned line with elevated R2 protein selected from the B3/mR2 population.

Consistent with previous reports showing that elevations in R2 gene expression leads to resistance to hydroxyurea, Table 3 shows that B3/mR2 and B3/R2c2 cells are significantly more resistant to the cytotoxic effects of hydroxyurea, at a range of concentrations, when compared to B3/SH cells. These results further demonstrate that B3/mR2 and B3/R2c2 cells express increased levels of an active R2 component of ribonucleotide reductase. B3/mR2 and B3/R2c2 cells were also significantly less sensitive to the cytotoxic effects of PALA and MTX, which act at sites other than ribonucleotide reductase (Table 3). Resistance to these two drugs ranged between approximately 10 fold with 100 nM MTX to more than 100 fold at most concentrations of PALA tested.

Figure 6B:
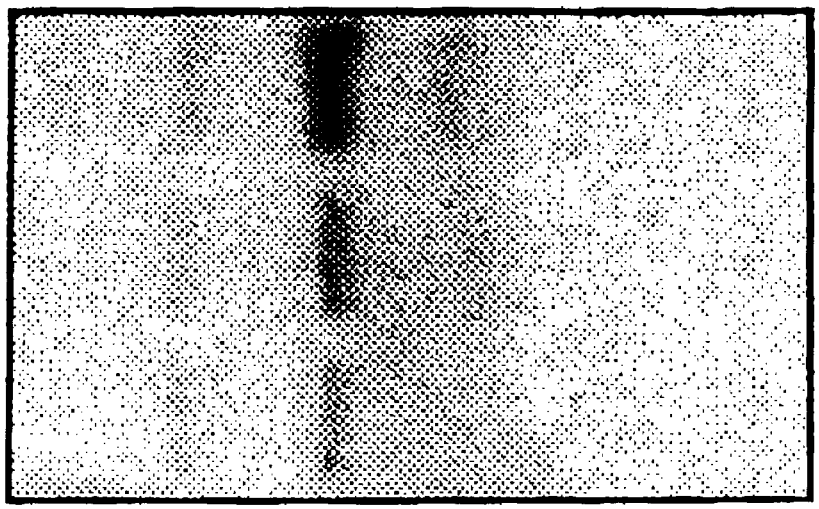
FIG. 6A–B are photographs of gels showing examples of Southern blot analysis of CAD (A) and DHFR (B) DNA with BALB/c 3T3 cells. DNA was digested to completion with Pstl. (A) B3/mR2 cells not exposed to PALA (a), and B3/mR2 cells from colonies that developed in the presence of 40 µM PALA (b), or in the presence of 50 µM PALA (c). (B) B3/mR2 cells not exposed to MTX (a), and B3/mR2 cells from colonies that developed in the presence of 60 nM MTX (b), or in the presence of 80 nM MTX (c).
Figure 6A:
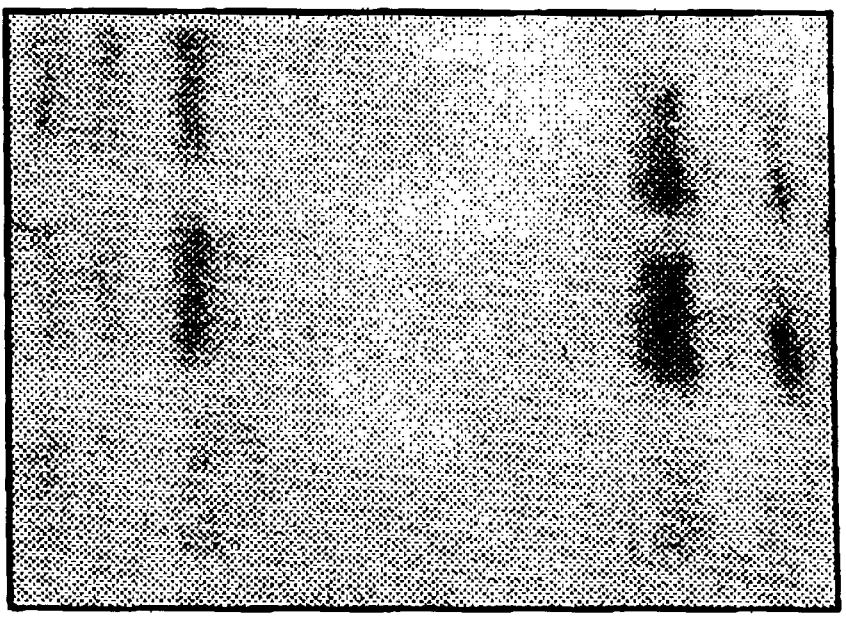

Furthermore, Southern blot analysis showed that colonies that developed in the presence of PALA or MTX contained amplifications of CAD or DHFR genes (FIG. 6), although as observed with mouse L cells (FIG. 5) and as has been reported in other studies [Hurta and wright, 1992; Hurta et al., 1991], not all colonies that developed in MTX containing medium exhibited DHFR gene amplification. Unlike PALA resistance, MTX resistance in mouse cells can occur through a variety of mechanisms [Otto et al., 1989; Stark et al., 1990; Flintoff, 1989].

The changes in sensitivity to chemotherapeutic compounds exhibited by cells containing elevated levels of the ribonucleotide reductase R2 component were further tested using NIH-3T3 cells containing the R2 expression retroviral vector (Table 4). These cells (N/R2-4) were resistant to hydroxyurea when compared to cells containing the retroviral vector lacking the R2 coding sequence (N/SH). The N/R2-4 cells were also significantly more resistant to MTX. Although the N/R2-4 cells showed a trend towards resistance to PALA when compared to N/SH cells, this trend was not statistically significant. This latter observation indicates that other factors inherent in the genetic differences between the cell lines used in this study, in addition to the increased R2 levels, can influence drug sensitivity responses.

Figure 7:
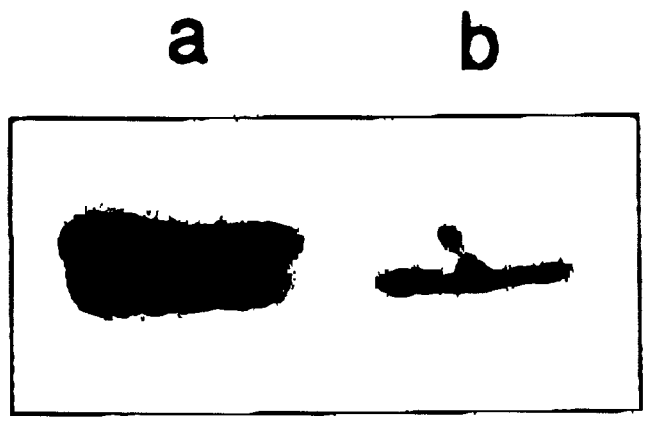
FIG. 7 is a photograph of a Western blot analysis of R2 protein levels in N/R2-4 (a) and N/R2+ASR2 (b) cells. To distinguish the vector R2 protein from the endogenous gene product in transfected cells, a human c-myc epitope coding for ten amino acids plus methionine was placed at the 5' end of the cDNA for R2. Recombinant (upper band) and endogenous (lower band) R2 protein is observed in lane a and is markedly reduced in R2 antisense containing cells (lane b). Both cell lines grew with approximately the same doubling time of about 16 hours.

Therefore, the hypothesis that R2 levels are important in determining drug sensitivity characteristics was tested by investigating drug sensitivities after decreasing the levels of R2, through expression of an R2 antisense construct introduced into N/R2-4 cells to produce the N/R2+ASR2 population. FIG. 7 shows that the level of R2 protein is markedly reduced in N/R2+ASR2 cells when compared to N/R2-4 cells. The N/R2+ASR2 cells were significantly more sensitive to hydroxyurea, PALA and MTX when compared to N/R2-4 cells (Table 4). Furthermore, sensitivity to these three drugs in the R2 antisense expressing cells was significantly increased when compared to control N/SH cells containing the empty vector (Table 4).

Mouse 10T ½ cells transfected with activated ras and a mutant oncogenic form of p53 are highly resistant to chemotherapeutic agents [Huang et al., 1995b]. The observation that R2 antisense expression can increase sensitivity of NIH-3T3 cells to hydroxyurea, PALA and MTX lead us to test the possibility that cells containing ras and mutated p53 may also exhibit reduced drug resistance characteristics in the presence of an R2 antisense sequence. Table 5 shows that this is correct. Cells containing the R2 antisense sequence are significantly more sensitive to hydroxyurea, PALA, and MTX when compared to cells containing the same vector but without R2 in the antisense orientation. These observations suggest that at least one of the determining factors relevant to drug sensitivity of these highly transformed and malignant cells, is ribonucleotide reductase R2 levels.

Figure 8:
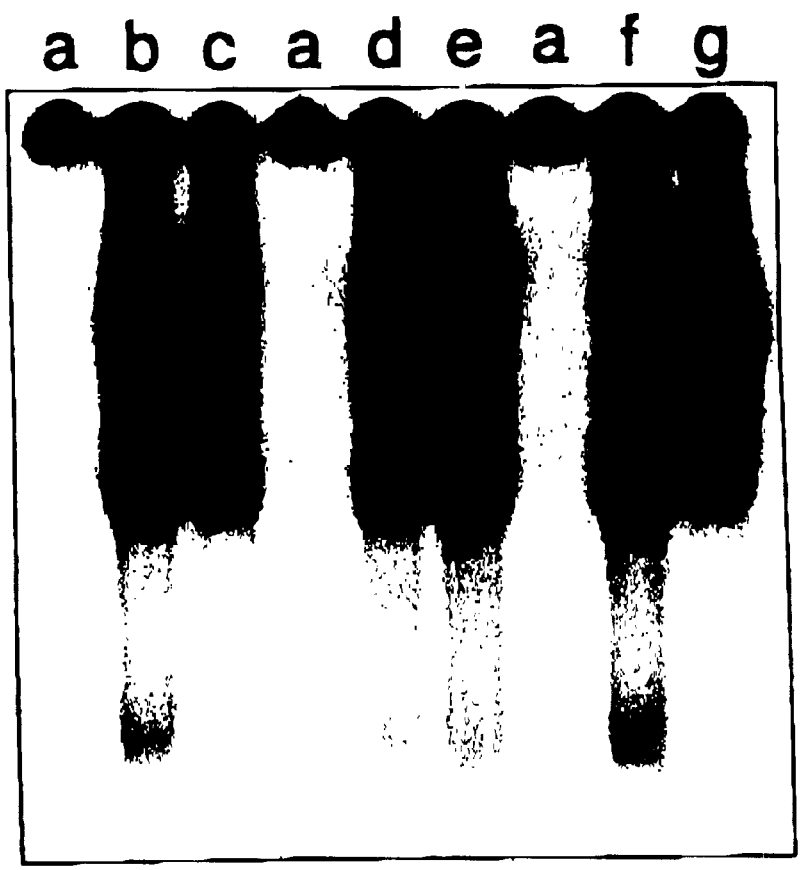
FIG. 8 is a photograph of a gel showing p53-DNA binding activity in cells from colonies that developed in the presence of PALA, MTX or hydroxyurea. (a) control 1B cells that are p53-null, (b) B3/mR2 cells that grew in the presence of 20 µM PALA, (c) B3/R2c2 cells that grew in the presence of 40 µM PALA, (d) B3/mR2 cells that grew in the presence of 40 nM MTX, (e) B3/R2c2 cells that grew in the presence of 60 nM MTX, (f) B3/mR2 cells that grew in the presence of 0.20 mM hydroxyurea, and (g) B3/R2c2 cells that grew in the presence of 0.30 mM hydroxyurea. Cells were incubated with $^{32}$P-labeled p53 consensus binding sequence in the presence of antibody 421, which activates p53 for DNA binding. Note the presence of complexes in all cell lines except in the 1B control p53-null cells. Low molecular weight complex formation results from p53-DNA binding and high molecular weight complex formation results from antibody supershifted p53-DNA binding.
Figure 10A:
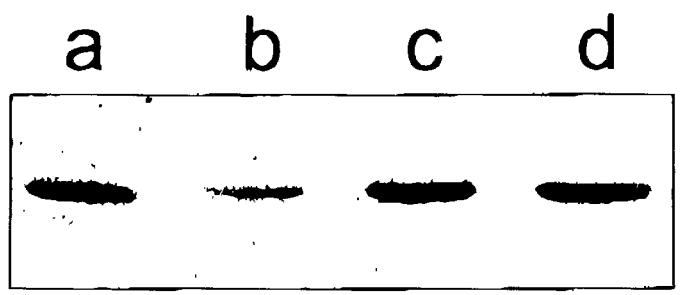
FIG. 10A–B are photographs of a Western blot analysis of AS-II-626-20 inhibition (A) and inhibition by a variety of R2 antisense oligonucleotides (B) of ribonucleotide reductase R2 protein level in L60 mouse tumor cells.
Figure 10B:
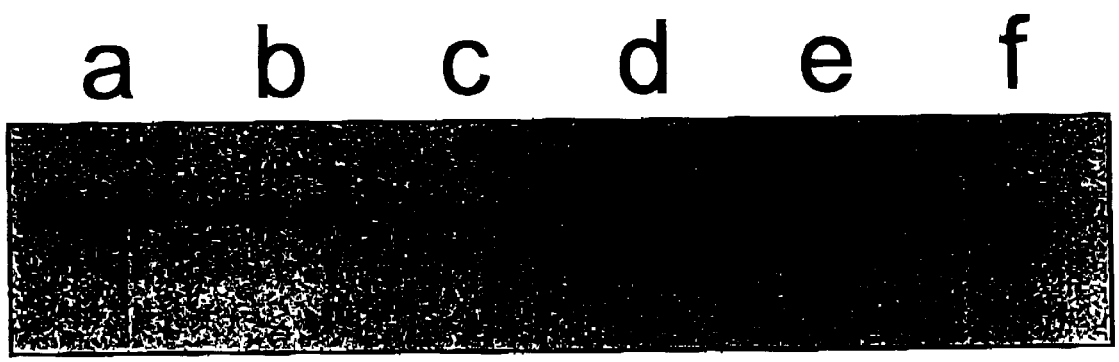

Evidence that Loss of p53 Protein Function is not Required for R2-Mediated Drug Resistance and Gene Amplification Inactivation or loss of p53 is a common event associated with the development of tumors and the accompanying decrease in genetic stability observed in malignant cells, including the ability to undergo spontaneous gene amplifications [Liningston et al., 1992; Yin et al., 1992; Takenaka et al., 1995]. Therefore, we tested the possibility that the increased drug resistance properties exhibited by the R2 overproducing B3/mR2 and B3/R2c2 cells may be occurring through a mechanism that results in a loss of wild type p53 activity. It has been demonstrated that p53 is a transcription factor, and that transactivation by wild type p53 but not mutated versions of p53 is sequence-specific, and correlates with its binding to consensus DNA sequences [Takenaka et al., 1995; Kern et al., 1992; Funk et al., 1992]. To determine the presence or absence of wild type p53 function in drug resistant colonies that developed in the presence of PALA, MTX or hydroxyurea, cell extracts were used in electrophoretic gel mobility shift assays (EMSA) [Price and Calderwood, 1993], to test for sequence specific p53 binding activity. FIG. 8 shows that drug resistant clones derived from R2 overexpressing cells exhibited wild type p53 binding activity. These observations also agreed with our inability to detect mutant p53 proteins in cells from drug resistant colonies in immunoprecipitation assays using the Pab240 monoclonal antibody [Gannon et al., 1990], which specifically detects common forms of mutant p53.

EXAMPLE 3

Antisense Deoxyribonucleotide Sequences That Target Ribonucleotide Reductase And Are Cytotoxic For Human Tumor Cells As shown in the Examples herein above full length antisense constructs of R2 affect the tumorigenicity and/or metastatic competence of tumor cells and susceptibility to chemotherapeutic agents. Applicants therefore investigated the potential of shorter antisense constructs of R1 and R2 for their effect on tumor cells.
Materials and Methods
Colony Forming Efficiency and Treatment of Cells with Antisense Constructs Colony forming efficiency was determined as previously reported [Huang and Wright, 1994]. The cells were cultured for 24 hours at 37° C. in growth medium with 10% fetal bovine serum. The cells were washed in 5 ml phosphate buffered saline, pH 7.2, once prior to lipofectin±oligonucleotide treatment.

The oligonucleotides being tested were added to cell cultures in the presence of 2.5 μg/ml of DOTMA/DOPE (Lipofectin; Life Technologies, Inc.) for four hours. The oligonucleotide was tested at 0.2 μM unless otherwise indicated. Controls were the cultures treated with lipofectin but without the oligonucleotide. After 4 hours the medium containing the oligonucleotide was removed and washed with 5 ml of growth medium. The cells were then cultured in growth medium containing 10% fetal bovine serum for seven to ten days. Surviving cells were visualized by methylene blue staining, and colonies were scored. In some experiments cell aliquotes were removed from the culture and viability was determined using the trypan blue exclusion test [Phillips, 1973]. Results were analyzed as percent of surviving cells compared to control cells.
Results Antisense molecules were identified that target ribonucleotide reductase. As shown below they were cytotoxic for a variety of human tumor cells. Sequences were found that facilitated drug-cytotoxicity for drug resistant tumor cells. That is, at very low non-cytotoxic concentrations, antisense sequences targeting ribonucleotide reductase can sensitize tumor cells to the cytotoxic activity of clinically important chemotherapeutic compounds.

In initial studies two antisense sequences of 20-mer, designated AS-II-336-20 and AS-II-2229B-20, directed against the R2 mRNA were synthesized and investigated. The first, AS-II-336-20, has the sequence 5'-TCC TGG AAG ATC CTC CTC GC-3' (SEQ ID No:1), and targets the R2 message of human ribonucleotide reductase at nucleotides 336–355, based on the numbering of R2 nucleotides [Pavloff et al., 1992]. The AS-II-2229B-20 sequence is: 5'-TCC CAC ATA TGA GAA AAC TC-3' (SEQ ID No:2), and targets the R2 message at nucleotides 2229–2248. Both AS-II-336-20 and AS-II-2229B-20 were constructed as phosphorothioate sequences to protect against nuclease activity [Anazodo et al., 1995].

Antisense construct AS-II-336-20 was tested for the ability to inhibit the proliferation of human tumor cells (Hela) in relative colony forming efficiency experiments as described herein above. Hela S3 cells (American Type Culture Collection, Rockville, Md., ATCC), and a Hela cell line (Hela 1 mM) previously selected for resistance to the antitumor agent, hydroxyurea [Wright et al., 1987], were tested (Table 6). Two experiments were undertaken with Hela S3 cells. With a 4 hour treatment of 0.2 μM antisense construct AS-II-336-20, inhibition of 92% and 82% was seen in colony forming efficiency in two experiments, respectively. The same experiment was repeated with the Hela 1 mM cell line and with varying concentrations of the antisense construct AS-II-336-20 (Table 6) with similar results, 0.2 μM was an effective concentration for inhibiting colony formation.

These data show that AS-II-336-20 is a very effective inhibitor of human tumor cell colony forming ability, and it is effective both in inhibiting the proliferation of human tumor cell colony forming ability and in inhibiting the proliferation of human tumor cells that exhibit resistance to another chemotherapeutic compound. Similarly, as shown in Table 6, antisense construct AS-II-336-20 is an effective antitumor compound in experiments performed with the mouse tumor cell line, SC2, which is a highly hydroxyurea resistant mouse L cell line [McClarty et al., 1988].

The antisense sequence AS-II-2229B-20 was also tested for the ability to inhibit the proliferation of human Hela tumor cells in relative colony forming efficiency experiments with results similar to that of AS-II-336-20 as shown in Table 6. These data show that AS-II-2229B-20 is a potent antitumor agent when tested with Hela S3 cells and with the drug resistant Hela 1 mM cell line. The antisense construct AS-II-2229B-20 was also tested for the ability to inhibit the proliferation of the human breast cancer cell line MDA435 and found to be very effective (Table 8).

The ribonucleotide reductase R2 antisense construct designated AS-II-2229B-20 was tested for tumor cell cytotoxicity by comparing the results obtained with human tumor and non-tumor cell populations. Hela S3 tumor cells and WI 38 normal non-tumorigenic human cells were used. Tumor cells were found to be much more sensitive to the cytotoxic effects of AS-II-2229B-20 than normal non-tumorigenic cells. For example, analysis of cells three days after antisense exposure indicated that tumor cells were approximately 5-times more sensitive to the cytotoxic effects of AS-II-2229B-20 than normal non-tumorigenic cells averaged over 4–8 determinations.

These results indicate that short oligodeoxyribonucleotide sequences in an antisense orientation are excellent antitumor agents, and suggest that other antisense constructs that target the R2 message may have similar properties. The best antitumor agents would be those that exhibit suitable energy related characteristics important for oligonucleotide duplex formation with their complementary templates, and which show a low potential for self-dimerization or self-complementation [Anazodo et al., 1996]. An analysis of the R2 mRNA using a computer program (OLIGO, Primer Analysis Software, Version 3.4), was carried out to determine antisense sequence melting temperature, free energy properties, and to estimate potential self-dimer formation and self-complimentary properties [Anazodo, et al., 1996], of a series of additional antisense sequences (Table 7) designed to target the R2 message. Table 7 shows a list of the additional R2 antisense inhibitors (SEQ ID Nos:3–102), with appropriate properties.

To test the antisense effects of many of these sequences, as phosphorthioate deoxyribonucleotides, they were examined in relative colony forming experiments performed with a series of human tumor cell lines. Many of these antisense constructs, as predicted, are potent inhibitors of human tumor cell proliferations. For results obtained with cancer cells derived brom the bladder, breast, lung, colon, pancrease, prostate, liver and cervix, see Table 12. In addition, in vivo studies with AS-II-626-20 treated tumor cells were undertaken in C3H/HeN mice as reported in Table 13 and show that there is a significant reduction in metastasis following antisense treatment.

Based on Example 2, treatment of human tumor cells with very low concentrations of short antisense sequences was tested to determine if these constructs could sensitize the tumor cells to inhibitory effects of other chemotherapeutic drugs. The concentration used was not cytotoxic in itself as shown in Table 6. The treatment of Hela S3 and Hela 1 mM cells with 0.02 $\mu$M of the AS-II-2229B-20 antisense construct increases the sensitivity of these cells to N-(phosphonacetyl)-L-aspartate (PALA) and to methotrexate (MTX) as shown in Table 9. These observations indicate that antisense compounds targeting the R2 message can act synergistically with well known chemotherapeutic agents.

Ribonucleotide reductase is composed of two dissimilar protein components coded by two distinct genes, R1 and R2. Therefore, the results described hereinabove suggest that the R1 message may also be an appropriate target for designing short antisense molecules that have potent antitumor activity. To test this possibility a 20-mer deoxyribonucleotide phosphorothioate sequence in antisense orientation, designated AS-I-1395-20, was constructed and its antitumor abilities were tested. The antisense construct AS-I-1395-20 has the sequence 5'-ACA GGA ATC TTT GTA GAG CA-3' (SEQ ID No:103), and targets the R1 message at nucleotides 1395–1414. As shown in Table 10 it is an effective inhibitor of tumor cell proliferation using Hela S3 cells and Hela 1 mM drug resistant cells. These results demonstrate the usefulness of designing antisense sequences that target the R1 message, and suggest that other potential sites may also be effective. Therefore, the R1 mRNA was analyzed in a search for antisense oligodeoxyribonucleotide sequences that exhibit suitable characteristics (as done for R2 mRNA and described above). Table 11 provides a list of antisense sequences with characteristics that are consistent with being antitumor agents.

EXAMPLE 4

Inhibition Of Transformation By R2 Antisense

Figure 9:
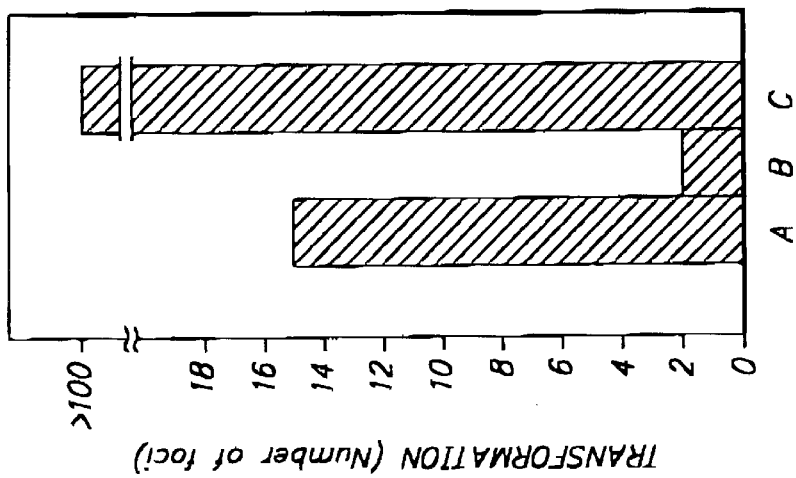
FIG. 9 is a graph showing the number of transformation foci in (a) NIH-3T3 mouse cells containing the H-ras oncogene, (b) NIH-3T3 mouse cells containing the H-ras oncogene and the R2 antisense sequence and (c) NIH-3T3 mouse cells containing the H-ras oncogene and the coding region sequence for R2. Results are averages of three experiments.

Utilizing the methods set forth in Examples 1–3, the inhibition of transformation of mammalian cells by treatment with the R2 antisense sequence of the R2 coding region [Fan et al, 1996b] was undertaken. NIH-3T3 mouse cells containing the H-ras oncogene were transfected with either the antisense orientation of the R2 coding sequence or the sense orientation of the R2 coding sequence. The results shown in FIG. 9 demonstrate that in the presence of the R2 antisense construct there was a decrease in transformed foci and reduced soft agar growth (FIG. 9, lane b) compared to the control cells (FIG. 9, lane a). As shown in Example 1, herein above, the R2 coding region can cooperate with H-ras to enhance malignancy as shown by the increased number of transformed foci (FIG. 9, lane c).

Furthermore, colony efficiency assays performed in soft agar as described herein demonstrated similar results. Colony forming efficiencies of 15.6±6.73 for NIH-3T3 mouse cells containing the H-ras oncogene, 4.4±2.62 for NIH-3T3 mouse cells containing the H-ras oncogene and the R2 antisense sequence, and 51±12.29 for NIH-3T3 mouse cells containing the H-ras oncogene and the coding region sequence for R2 were observed.

EXAMPLE 5

Western blot analysis of AS-II-626-20 inhibition of ribonucleotide reductase R2 protein level in L60 mouse tumor cells Cells were treated for 4 hours with growth medium supplemented with lipofectin but without antisense oligonucleotides (a) or with lipofectin medium containing 0.2 $\mu$M AS-II-626-20(b). As added controls the tumor cells were also treated for 4 hours with growth medium supplemented with lipofectin and 0.2 $\mu$M oligonucleotide scrambled control, which contains the same proportion of nucleotides found in AS-II-626-20 but in a different order (ACGCACTCAGCTAGTGACAC; SEQ ID No:163) (c) or with 0.2 $\mu$M mismatch oligonucleotide, which contains a four nucleotide mismatch mutation when compared to AS-II-626-20 (TCGC changed to CTGC) (d). Note the significant decrease in R2 protein in tumor cells treated with AS-II-626-20 (b) when compared to the controls (a, c and d).

Decrease in R2 protein levels in mouse L60 tumor cells following treatment with a variety of R2 antisense oligonucleotides, as determined by Western blot analysis Cells were treated for 4 hours with 0.2 $\mu$M oligonucleotide in the presence of lipofectin (b to f), or with lipofectin without oligonucleotide as a control (a). (b) Cells treated with AS-II-667-20; (c) cells treated with AS-II-816-20; (d) cells treated with AS-II-1288-20; (e) cells treated with AS-II-1335-20 and, (f) cells treated with AS-II-1338-20. Note the decrease in R2 protein levels in cells treated with antisense oligonucleotides that target the R2 mRNA, in keeping with their abilities to inhibit human tumor cell proliferation (Table 12).

Throughout this application, various publications, including United States patents and published patent applications are referenced by author and year or number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE 1

INCREASED COLONY FORMATION IN SOFT AGAR BY ras-TRANSFORMED CELLS CONTAINING THE RECOMBINANT R2 VECTOR

| Cell Line | Colonies (average ± SE) formed in soft agar with varying cell inoculum[a] | | |
|---|---|---|---|
| | $10^3$ | $10^4$ | $10^5$ |
| C1/SH | 0 | 4 ± 3 | 66 ± 9 |
| C1/mR2 | 3 ± 3 | 28 ± 7 | 347 ± 45 |
| r-2/SH | ND | 9 ± 2 | 105 ± 7 |
| r-2/mR2 | ND | 24 ± 1 | 298 ± 11 |
| NR4/SH | 0 | 3 ± 1 | 32 ± 4 |
| NR4/mR2 | 2 ± 1 | 14 ± 2 | 127 ± 10 |
| r-3 | 7 ± 1 | 100 ± 11 | ND |
| r-3/mR2 | 31 ± 4 | 309 ± 17 | ND |

[a]The number of colonies presented were the results obtained in three independent experiments, except those obtained for r-2/SH and r-2/mR2 cells which were the results from single experiments with triplicate dishes. ND, not determined.

TABLE 2

DRUG SENSITIVITIES DETERMINED BY RELATIVE COLONY FORMING EFFICIENCIES $\times 10^4$

A. PALA

| DRUG CONC. | CELL LINES | | | | |
|---|---|---|---|---|---|
| | W.T. | H2 | H4 | LHF | SC2 |
| 20 μM | 172.3 ± 126.3 | 406.7 ± 202.2 | 322.5 ± 36.4 | 233.3 ± 3.6 | 850.1 ± 325.2 |
| 30 μM | 50.3 ± 20.5 | 39.4 ± 16.4 | 84.0 ± 30.0 | 78.8 ± 7.9 | 187.6 ± 46.4 |
| 40 μM | 15.0 ± 7.0 | 23.3 ± 10.4 | 43.3 ± 9.6 | 46.5 ± 9.9 | 37.5 ± 8.7 |
| 50 μM | 3.6 ± 1.1 | 7.9 ± 1.7 | 23.2 ± 0.5 | 25.0 ± 6.8 | 47.5 ± 35.8 |
| 60 μM | 1.3 ± 0.4 | 3.6 ± 0.6 | 11.1 ± 1.4 | 10.7 ± 3.0 | 17.6 ± 1.2 |

B. MTX

| CONC. | W.T. | H2 | H4 | LHF | SC2 |
|---|---|---|---|---|---|
| 40 nM | 11.2 ± 7.2 | 52.6 ± 25.2 | 44.2 ± 20.9 | 143.4 ± 41.3 | 880.4 ± 147.4 |
| 60 nM | 12.3 ± 7.2 | 73.7 ± 16.6 | 34.7 ± 11.2 | 63.5 ± 18.6 | 566.8 ± 66.2 |
| 80 nM | 2.2 ± 1.6 | 67.7 ± 20.0 | 39.3 ± 18.7 | 68.2 ± 19.2 | 306.6 ± 61.5 |
| 100 nM | 0.8 ± 0.4 | 75.3 ± 10.0 | 15.1 ± 8.8 | 60.8 ± 16.7 | 261.8 ± 39.7 |
| 150 nM | 0.5 ± 0.2 | 53.3 ± 9.4 | 32.3 ± 13.7 | 63.9 ± 16.0 | 301.6 ± 76.8 |

The relative colony forming efficiencies are shown ± se, and the values presented are from 4 to 8 determinations. Statistically significant differences were observed when data obtained with H2 (p = 0.0004), H4 (p ≤ = 0.0001), LHF (p ≤ 0.0001), and SC2 (p ≤ 0.0001) were each compared to data obtained with the parental wild type (W.T.) cell line.

TABLE 3

DRUG SENSITIVITIES DETERMINED BY RELATIVE COLONY FORMING EFFICIENCIES $\times 10^{-4}$

A. HYDROXYUREA

| DRUG CONC | CELL LINES | | |
|---|---|---|---|
| | B3/SH | B3/mR2 | B3/R2c2 |
| 0.1 mM | 3.3 ± 1.4 | 1310 ± 319.0 | 830.8 ± 97.0 |
| 0.4 mM | 0.17 ± 0.19 | 14.6 ± 4.0 | 33.7 ± 11.0 |
| 0.5 mM | 0.21 ± 0.14 | 6.5 ± 4.6 | 26.9 ± 11.9 |
| 0.6 mM | 0.41 ± 0.22 | 5.2 ± 3.7 | 12.5 ± 4.6 |
| 0.8 mM | 0.19 ± 0.62 | 2.6 ± 1.4 | 13.2 ± 6.4 |

TABLE 3-continued

DRUG SENSITIVITIES DETERMINED BY RELATIVE COLONY FORMING EFFICIENCIES $\times 10^{-4}$

| CONC | B3/SH | B3/mR2 | B3/R2c2 |
|---|---|---|---|
| B. PALA | | | |
| 10 μM | 17.9 ± 11.0 | 965.0 ± 529.7 | 1230.0 ± 97.0 |
| 20 μM | 0.39 ± 0.18 | 120.1 ± 28.4 | 55.1 ± 15.6 |
| 40 μM | 0.35 ± 0.01 | 25.0 ± 4.6 | 20.2 ± 6.8 |
| 50 μM | 0.24 ± 0.14 | 27.6 ± 8.9 | 15.9 ± 4.0 |
| 60 μM | 0.12 ± 0.05 | 25.0 ± 6.4 | 18.7 ± 5.3 |
| 80 μM | 0.17 ± 0.08 | 27.1 ± 6.75 | 20.0 ± 4.9 |
| C. MTX | | | |
| 20 nM | 192.6 ± 44.6 | 1055.0 ± 239.0 | 382.4 ± 71.3 |
| 40 nM | 15.7 ± 2.9 | 62.1 ± 8.8 | 60.8 ± 13.0 |
| 60 nM | 6.1 ± 2.0 | 76.7 ± 21.6 | 64.1 ± 20.5 |
| 80 nM | 2.2 ± 0.7 | 17.5 ± 3.6 | 20.1 ± 5.5 |
| 100 nM | 1.5 ± 0.5 | 12.3 ± 2.8 | 21.0 ± 7.2 |
| 150 nM | 3.0 ± 1.1 | 23.0 ± 7.6 | 33.4 ± 14.3 |

TABLE 3-continued

DRUG SENSITIVITIES DETERMINED BY RELATIVE COLONY FORMING EFFICIENCIES $\times 10^{-4}$ The relative colony forming efficiencies are shown ± SE, and the values presented are from 4 to 12 determinations. Statistically significant differences were observed when data obtained with B3/mR2 or with B3/R2c2 were compared with data obtained with B3/SH (all p values were ≤ 0.0001 for data obtained in the presence of hydroxyurea, PALA or MTX).

TABLE 4

DRUG SENSITIVITIES DETERMINED BY RELATIVE COLONY FORMING EFFICIENCIES ×10$^{-4}$

A. HYDROXYUREA

| DRUG CONC | CELL LINES | | |
|---|---|---|---|
| | N/SH | N/R2-4 | N/R2 + ASR2 |
| 0.3 mM | 1.14 ± 0.12 | 46.1 ± 9.8 | 0.49 ± 0.34 |
| 0.4 mM | 0.71 ± 0.17 | 18.0 ± 6.7 | 0.14 ± 0.14 |

| CONC | N/SH | N/R2-4 | N/R2 + ASR2 |
|---|---|---|---|

B. PALA

| | | | |
|---|---|---|---|
| 10 μM | 5.28 ± 1.5 | 6.22 ± 3.3 | 1.81 ± 0.8 |
| 15 μM | 5.83 ± 2.7 | 10.0 ± 5.5 | 0.58 ± 0.3 |
| 20 μM | 0.30 ± 0.1 | 1.71 ± 1.2 | 0.04 ± 0.04 |
| 25 μM | 0.53 ± 0.3 | 0.8 ± 0.7 | 0.04 ± 0.04 |
| 30 μM | 0.48 ± 0.08 | 1.03 ± 0.07 | 0.12 ± 0.12 |
| 40 μM | 0.27 ± 0.2 | 0.14 ± 0.08 | 0.04 ± 0.04 |

C. MTX

| | | | |
|---|---|---|---|
| 20 nM | 655 ± 74.8 | 540 ± 25.1 | 423 ± 119 |
| 40 nM | 21 ± 12.1 | 147 ± 4.2 | 3.5 ± 1.9 |
| 60 nM | 3.4 ± 2.2 | 62.2 ± 30.7 | 1.9 ± 1.3 |
| 80 nM | 5.0 ± 5.0 | 50.4 ± 23.9 | 2.5 ± 1.5 |
| 100 nM | 4.2 ± 2.5 | 66.1 ± 32.8 | 1.1 ± 0.6 |
| 150 nM | 1.4 ± 0.9 | 21.0 ± 11.5 | 0, n = 4 |

The relative colony forming efficiencies are shown ± SE, and the values presented are from 4 to 6 determinations. Where 0 is shown the number of determinations using $1 \times 10^5$ cells per test is shown as 4 (n = 4). Statistically significant differences were observed when data obtained with N/SH in the presence of PALA was compared to data obtained with N/R2-4 or with N/R2 + ASR2 in the presence of hydroxyurea (p = 0.0001 in both cases) or in thepresence of MTX (p = 0.0002 and 0.032, respectively). Statistically significant differences were also observed when data obtained with N/SH in the presence of PALA was compared to data obtained with N/R2 + ASR2 (p = 0.002), but not with data obtained with N/R2-4.

TABLE 5

DRUG SENSITIVITIES DETERMINED BY RELATIVE COLONY FORMING EFFICIENCIES ×10$^{-4}$

A. HYDROXYUREA

| DRUG CONC | CELL LINES | | | |
|---|---|---|---|---|
| | RP3/SH | RP3/ASR2 | RP6/SH | RP6/ASR2 |
| 0.1 mM | 263.6 ± 19.3 | 109.8 ± 43 | 201.3 ± 27.2 | 43.8 ± 12.3 |
| 0.2 mM | 53.6 ± 13.7 | 22.9 ± 3.1 | 35.5 ± 8.4 | 8.6 ± 2.5 |
| 0.3 mM | 20.8 ± 7.5 | 6.6 ± 2.5 | 12.6 ± 2.4 | 4.5 ± 1.1 |
| 0.4 mM | 5.8 ± 1.9 | 1.0 ± 0.2 | 10.8 ± 4.1 | 1.2 ± 0.5 |
| 0.5 mM | 4.8 ± 1.9 | 0.2 ± 0.1 | 12.1 ± 3.9 | 1.8 ± 0.9 |
| 0.6 mM | 0.7 ± 0.3 | 0.3 ± 0.1 | 6.6 ± 2.9 | 1.5 ± 0.7 |
| 0.8 mM | 0.8 ± 0.3 | 0.1 ± 0.05 | 1.7 ± 1.2 | 0.4 ± 0.3 |

| CONC | RP3/SH | RP3/ASR2 | RP6/SH | RP6/ASR2 |
|---|---|---|---|---|

B. PALA

| | | | | |
|---|---|---|---|---|
| 10 μM | 2569 ± 338 | 1183 ± 384 | 4619 ± 648 | 2083 ± 960 |
| 20 μM | 123.4 ± 19.3 | 86.1 ± 32.9 | 1220 ± 255 | 368 ± 154 |
| 30 μM | 45.2 ± 7.8 | 19.5 ± 4.7 | 450 ± 129 | 316 ± 171 |
| 40 μM | 15.0 ± 4.9 | 4.7 ± 0.6 | 271 ± 68 | 116 ± 54 |
| 50 μM | 9.3 ± 3.6 | 2.1 ± 0.8 | 109 ± 23 | 41.7 ± 23 |
| 60 μM | 3.9 ± 1.6 | 0.3 ± 0.2 | 55.5 ± 13 | 13.2 ± 6.3 |

C. MTX

| | | | | |
|---|---|---|---|---|
| 20 nM | 961.7 ± 134 | 485.9 ± 165 | 1856 ± 464 | 1504 ± 486 |
| 40 nM | 347.1 ± 154 | 77.8 ± 18 | 172 ± 41.3 | 91.5 ± 28.1 |
| 60 nM | 123.8 ± 64 | 18.1 ± 6.2 | 77.3 ± 15.6 | 49.9 ± 14.1 |
| 80 nM | 66.5 ± 37 | 4.4 ± 0.8 | 68.7 ± 16.7 | 36.0 ± 6.0 |
| 100 nM | 34.8 ± 21 | 0.6 ± 0.06 | 46.6 ± 5.6 | 14.4 ± 3.8 |
| 150 nM | 4.7 ± 3 | 0.2 ± 0.1 | 11.1 ± 4.4 | 3.5 ± 0.9 |

The relative colony forming efficiencies are shown ± SE, and the values presented are from 4 to 6 determinations. Statistically significant differences were observed when data obtained with RP6/SH was compared with data obtained with RP6/ASR2 (p = 0.0001, 0.0001 and 0.0001 in the presence of hydroxyurea, PALA and MTX, respectively). Significant differences were also observed when data obtained with RP3/SH was compared with data obtained with RP3/ASR2 (p = 0.04, 0.0001and 0.004 in the presence of hydroxyurea, PALA and MTX, respectively).

TABLE 6

REDUCED COLONY FORMING EFFICIENCY FOLLOWING TREATMENT WITH R2 ANTISENSE CONSTRUCTS

| Conc. AS-II-336-20[a] | % Inhib. | Conc. AS-II-2229B-20[b] | % Inhib. |
|---|---|---|---|
| CELL LINE: Hela S3 | | | |
| 0 | — | 0 | — |
| 0.2 μM | 92% | 0.05 μM | 50% |
| 0.2 μM | 82% | 0.10 μM | 80% |
| | | 0.20 μM | 95% |
| | | 0.20 μM | 97% |
| CELL LINE: Hela 1 mM | | | |
| 0 | — | 0 | — |
| 0.01 μM | 15% | 0.01 μM | 0% |
| 0.05 μM | 25% | 0.02 μM | 0% |
| 0.10 μM | 60% | 0.03 μM | 21% |
| 0.20 μM | 85% | 0.04 μM | 34% |
| | | 0.05 μM | 48% |
| | | 0.05 μM | 50% |
| | | 0.10 μM | 78% |
| | | 0.20 μM | 97% |
| | | 0.20 μM | 90% |
| CELL LINE: Mouse SC2 | | | |
| 0 | — | | |
| 0.2 μM | 95% | | |

TABLE 7

ANTISENSE SEQUENCES DESIGNED TO TARGET THE R2 MESSAGE

| SEQ ID No: | Name | Sequence 5'–3' | Tm ° C. | dG kDa/mol |
|---|---|---|---|---|
| SEQ ID No:3 | AS-II-6-20 | ACCCTTCCCATTGGCTGCGC | 62.8 | −45.5 |
| SEQ ID No:4 | AS-II-13-20 | GsCCsTCCGsACCsCTTCsCCsATTsG | 60.1 | −43.7 |
| SEQ ID No:5 | AS-II-14-20 | TGCCTCCGACCCTTCCCATT | 60.1 | −43.7 |
| SEQ ID No:6 | AS-II-16-18 | TGCCTCCGACCCTTCCCA | 58.4 | −40.3 |
| SEQ ID No:7 | AS-II-75-20 | CsGCGsCGCsTCCsCGGsCCCsTTCsC | 72.7 | −53.7 |
| SEQ ID No:8 | AS-II-75-20 | CGCGCGCTCCCGGCCCTTCC | 72.7 | −53.7 |
| SEQ ID No:9 | AS-II-79-14 | CGCGCTCCCGGCCC | 59.1 | −38.8 |
| SEQ ID No:10 | AS-II-109-20 | CsCCCsTCACsTCCsAGCsAGCsCTsT | 57.9 | −41.8 |
| SEQ ID No:11 | AS-II-110-20 | ACCCCTCACTCCAGCAGCCT | 57.3 | −41.2 |
| SEQ ID No:12 | AS-II-114-20 | GGCGACCCCTCACTCCAGCA | 61.8 | −43.2 |
| SEQ ID No:13 | As-II-127-12 | GCACGGGCGACC | 41.7 | −28.8 |
| SEQ ID No:14 | AS-II-130-20 | TGGGACAGGGTGCACGGGCG | 67.6 | −46.7 |
| SEQ ID No:15 | AS-II-134-20 | GACGGCTGGGACAGGGTGCA | 62.6 | −43.2 |
| SEQ ID No:16 | AS-II-151-20 | GAGCAGCCAGGACAGGACGG | 59.3 | −41.7 |
| SEQ ID No:17 | AS-II-163-20 | GsCGsAAGsCAGsAGCSGAGsCAGCsC | 62.1 | −44.3 |
| SEQ ID No:18 | AS-II-166-20 | GCAGCGAAGCAGAGCGAGCA | 61.4 | −43.1 |
| SEQ ID No:19 | AS-II-185-20 | GGGAGAGCATAGTGGAGGCG | 56.0 | −40.9 |
| SEQ ID No:20 | AS-II-189-20 | CGGAGGGAGAGCATAGTGGA | 54.1 | −39.4 |
| SEQ ID No:21 | AS-II-201-20 | GCGAGCGGGACACGGAGGGA | 63.5 | −45.1 |
| SEQ ID No:22 | AS-II-217-20 | CGGGTCCGTGATGGGCGCGA | 69.5 | −48.8 |
| SEQ ID No:23 | AS-II-225-20 | AGCTGCTGCGGGTCCGTGAT | 61.4 | −43.6 |
| SEQ ID No:24 | AS-II-253-14 | CCCCTTCAGCGGCG | 50.8 | −34.4 |
| SEQ ID No:25 | AS-II-280-20 | CGGCGGCGTGTTCTCCTTGT | 61.8 | −44.2 |
| SEQ ID No:26 | AS-II-288-12 | CGGCGGCGTGTT | 43.2 | −29.6 |
| SEQ ID No:27 | AS-II-323-20 | TCCTCGCGGTCTTGCTGGCC | 64.1 | −45.5 |
| SEQ ID No:28 | AS-II-344-20 | CCGTGGGCTCCTGGAAGATC | 58.0 | −41.9 |
| SEQ ID No:29 | AS-II-362-20 | CTGCTTTAGTTTTCGGCTCC | 51.2 | −39.2 |
| SEQ ID No:30 | AS-II-391-17 | CGGCTCATCCTCCACGC | 54.5 | −37.3 |
| SEQ ID No:31 | AS-II-404-20 | GGTTTTCTCTCAGCAGCGGC | 56.4 | −41.4 |
| SEQ ID No:32 | AS-II-412-20 | GCGGCGGGGGTTTTCTCTCA | 62.8 | −45.8 |
| SEQ ID No:33 | AS-II-414-20 | AAGCGGCGGGGGTTTTCTCT | 60.7 | −45.8 |
| SEQ ID No:34 | AS-II-425-20 | GGAAGATGACAAAGCGGCGG | 59.1 | −43.0 |
| SEQ ID No:35 | AS-II-439-20 | ATGGTACTCGATGGGGAAGA | 50.8 | −37.8 |
| SEQ ID No:36 | AS-II-472-20 | AGCCTCTGCCTTCTTATACA | 46.1 | −35.8 |
| SEQ ID No:37 | AS-II-494-20 | CCTCCTCGGCGGTCCAAAAG | 60.4 | −44.3 |
| SEQ ID No:38 | AS-II-496-16 | TCCTCGGCGGTCCAAA | 54.8 | −37.0 |
| SEQ ID No:39 | AS-II-549-20 | TATCTCTCCTCGGGTTTCAG | 48.4 | −36.7 |
| SEQ ID No:40 | AS-II-579-20 | GCAAAGAAAGCCAGAACATG | 50.0 | −37.2 |
| SEQ ID No:41 | AS-II-619-20 | TCGCTCCACCAAGTTTTCAT | 52.1 | −38.3 |
| SEQ ID No:42 | AS-II-626-20 | GGCTAAATCGCTCCACCAAG | 53.9 | −40.3 |
| SEQ ID No:43 | AS-II-634-20 | AACTTCTTGGCTAAATCGCT | 48.0 | −37.6 |
| SEQ ID No:44 | AS-II-667-20 | GAAGCCATAGAAACAGCGGG | 53.9 | −40.3 |
| SEQ ID No:45 | AS-II-784-20 | GACACAAGGCATCGTTTCAA | 50.9 | −36.8 |
| SEQ ID No:46 | AS-II-798-20 | TCTGCCTTCTTCTTGACACA | 48.0 | −34.9 |
| SEQ ID No:47 | AS-II-816-20 | ATCCAGCGCAAGGCCCAGTC | 60.9 | −43.7 |
| SEQ ID No:48 | AS-II-861-20 | GCAAAGGCTACAACACGTTC | 50.0 | −37.1 |
| SEQ ID No:49 | AS-II-890-20 | AACCGGAAAAGAAAATGCCT | 52.2 | −40.4 |
| SEQ ID No:50 | AS-II-909-20 | CAGAATATCGACGCAAAAGA | 48.2 | −36.5 |
| SEQ ID No:51 | AS-II-933-20 | GGCATCAGTCCTCGTTTCTT | 50.8 | −37.7 |
| SEQ ID No:52 | AS-II-981-20 | TGTAAACCCTCATCTCTGCT | 46.2 | −35.0 |
| SEQ ID No:53 | AS-II-1001-20 | TCAGGCAAGCAAAATCACAG | 51.3 | −37.2 |
| SEQ ID No:54 | AS-II-1006-20 | GAACATCAGGCAAGCAAAAT | 49.4 | −37.1 |
| SEQ ID No:55 | AS-II-1023-20 | TTGTGTACCAGGTGTTTGAA | 45.9 | −33.9 |
| SEQ ID No:56 | AS-II-1040-20 | CTCTCTCCTCCGATGGTTTG | 51.1 | −37.7 |
| SEQ ID No:57 | AS-II-1048-20 | TTCTCTTACTCTCTCCTCCG | 45.2 | −35.0 |
| SEQ ID No:58 | AS-II-1144-20 | GTATTGCTTCATTAGAGTGC | 41.6 | −33.0 |
| SEQ ID No:59 | AS-II-1182-20 | CCCAGTTCCAGCATAAGTCT | 48.4 | −36.5 |
| SEQ ID No:60 | AS-II-1197-20 | AAAACCTTGCTAAAACCCAG | 48.3 | −37.8 |
| SEQ ID No:61 | AS-II-1217-20 | CAAATGGGTTCTCTACTCTG | 43.7 | −33.8 |
| SEQ ID No:62 | AS-II-1224-20 | ATAAAGTCAAATGGGTTCTC | 42.6 | −34.0 |
| SEQ ID No:63 | AS-II-1254-20 | TTAGTCTTTCCTTCCAGTGA | 43.8 | −33.9 |
| SEQ ID No:64 | AS-II-1278-20 | TCGCCTACTCTCTTCTCAAA | 46.8 | −35.6 |
| SEQ ID No:65 | AS-II-1288-20 | CCTCTGATACTCGCCTACTC | 45.6 | −35.1 |
| SEQ ID No:66 | AS-II-1302-20 | GACATCACTCCCATCCTCTG | 48.7 | −35.3 |
| SEQ ID No:67 | AS-II-1335-20 | GCATCCAAGGTAAAAGAATT | 45.6 | −36.1 |
| SEQ ID No:68 | AS-II-1338-20 | TCAGCATCCAAGGTAAAAGA | 47.4 | −35.9 |
| SEQ ID No:69 | AS-II-1342-20 | GAAGTCAGCATCCAAGGTAA | 46.7 | −35.3 |
| SEQ ID No:70 | AS-II-1345-20 | TTAGAAGTCAGCATCCAAGG | 47.0 | −35.6 |
| SEQ ID No:71 | AS-II-1362-20 | GCACATCTTCAGTTCATTTA | 42.4 | −32.8 |
| SEQ ID No:72 | AS-II-1364-20 | GGGCACATCTTCAGTTCATT | 48.9 | −36.2 |
| SEQ ID No:73 | AS-II-1381-20 | AAAAATCAGCCAAGTAAGGG | 48.1 | −38.0 |
| SEQ ID No:74 | AS-II-1390-20 | ATGGAAAAAAAAAATCAGCC | 48.1 | −38.0 |
| SEQ ID No:75 | AS-II-1438-20 | TTCATGGTGTGGCTAGTTGG | 50.8 | −36.8 |
| SEQ ID No:76 | AS-II-1499-20 | AGGACTGGTTGTGAGGTAGC | 48.1 | −35.7 |
| SEQ ID No:77 | AS-II-1517-20 | CCAGCACTATAAACAGACAG | 42.2 | −32.8 |

TABLE 7-continued

ANTISENSE SEQUENCES DESIGNED TO TARGET THE R2 MESSAGE

| SEQ ID No: | Name | Sequence 5'-3' | Tm °C. | dG kDa/mol |
|---|---|---|---|---|
| SEQ ID No:78 | AS-II-1538-20 | TTCTGGCAAAAGGTGATACT | 46.5 | −35.6 |
| SEQ ID No:79 | AS-II-1560-20 | GTAAGTCACAGCCAGCCAGG | 52.2 | −37.8 |
| SEQ ID No:80 | AS-II-1581-20 | ACTGCCATTGTCACTGCTAT | 47.0 | −34.9 |
| SEQ ID No:81 | AS-II-1659-20 | TGGCTGTGCTGGTTAAAGGA | 53.2 | −38.7 |
| SEQ ID No:82 | AS-II-1666-20 | TTTTAACTGGCTGTGCTGGT | 50.0 | −37.2 |
| SEQ ID No:83 | AS-II-1700-20 | ATTAAAATCTGCGTTGAAGC | 46.8 | −36.6 |
| SEQ ID No:84 | AS-II-1768-20 | TATCGCCGCCGTGAGTACAA | 56.5 | −40.9 |
| SEQ ID No:85 | AS-II-1773-20 | GCTATTATCGCCGCCGTGAG | 57.1 | −42.6 |
| SEQ ID No:86 | AS-II-1775-12 | ATCGCCGCCGTG | 42.9 | −29.5 |
| SEQ ID No:87 | AS-II-1790-20 | GAAACCAAATAAATCAAGCT | 43.4 | −34.9 |
| SEQ ID No:88 | AS-II-1819-20 | TTAGTGGTCAGGAGAATGTA | 41.7 | −32.5 |
| SEQ ID No:89 | AS-II-1976-20 | TGGCACCAACTGACTAATAT | 44.5 | −34.2 |
| SEQ ID No:90 | AS-II-1989-20 | CCTGTCTTCTATCTGGCACC | 48.6 | −36.2 |
| SEQ ID No:91 | AS-II-2009-20 | GCCACAGGATAAAAACACAA | 47.7 | −35.9 |
| SEQ ID No:92 | AS-II-2026-20 | CCCAGGACACTACACAAGCC | 51.8 | −37.5 |
| SEQ IP No:93 | AS-II-2044-20 | TCAGAGGGGGCAGAGAATCC | 55.4 | −40.2 |
| SEQ ID No:94 | AS-II-2067-20 | TCCTTTATCCCACAACACTC | 46.3 | −35.0 |
| SEQ ID No:95 | AS-II-2083-20 | CCTTGCCCTGAGAGATTCCT | 52.3 | −39.0 |
| SEQ ID No:96 | AS-II-2083-20 | CsCTsTGsCCsCTsGAsGAsGAsTTsCCsT | 52.3 | −39.0 |
| SEQ ID No:97 | AS-II-2128-20 | GGCCCAGATCACCCCTAAAT | 54.3 | −40.9 |
| SEQ ID No:98 | AS-II-2151-20 | AAACGGCTTCTCACACATAT | 46.3 | −35.4 |
| SEQ ID No:99 | AS-II-2164-20 | GAGAAATAAAATGAAACGGC | 46.2 | −36.6 |
| SEQ ID No:100 | AS-II-2182-20 | CGTTGAGGAAAATACAGTGA | 45.1 | −34.3 |
| SEQ ID No:101 | AS-II-2229A-20 | GCTCCCACATATGAAAACTC | 46.1 | −35.2 |
| SEQ ID No:102 | AS-II-2372-20 | CACACAACCTACTTACACCA | 42.7 | −32.3 |

Footnotes for Table 7
Name includes the following:
AS = antisense
II = R2
The first number indicates the first nucleotide position in the R2 mRNA sequence.
The second number indicates the length of the sequence segment.
The sequence AS-II-2229A shown in the Table and the sequence AS-II-2229B described in the text are alternate sequences, with 2229A chosen from the version of R2 in GENBANK (submitted by Pavloff) and 2229B chosen from the version published by Pavloff et al., J. DNA Sequencing and Mapping, 2:227–234; 1992.
Sequences were fully thioated unless partial thioation is indicated (s).
[1]Tm °C. = Melting temperature of oligonucleotide duplex formed.
[2]dG = Free energy value for oligonucleotide-complement dimer formation.
In addition to the above analysis, estimates of potential dimer formation (D), potential self-complementary interactions (H), and the potential to bind to sequences in the R2 message other than the target sequence were obtained. Analysis and estimates described above were obtained by using the computer modelling program OLIGO Primer Analysis Software, Version 3.4 (distributed by National Biosciences). The program allows the determination of Tm °C. and dG values, and also providesa qualitative estimation of the D, H and B parameters indicating "no potential", "some potential" or essentially "complete potential". In choosing the oligonucleotide sequences we gave high priority to sequences that exhibited high Tm °C. and dG values, which are important for tight binding of antisense molecules to their complementary strands, and high priority to antisense sequences that had estimates of no potential in D, H and B. Of the threecategories (D, H, B) the most important ones were D and H, since B (i.e. binding to other regions of the R2 mRNA in addition to the precise target sequence) may enhance rather than compromise oligonucleotide activity. Most of the sequences shown in Table 7 had no potential in the D and H categories. Some sequences exhibited "some potential" in D or H and were later found intumor cell growth inhibition studies to be effective (Table 12) and therefore were also included in Table 7. We found that this approach to choosing antisense oligonucleotide inhibitors was extremely effective, since the vast majority of the chosen sequences exhibited anti-tumor properties as shown in Table 12.

TABLE 8

TREATMENT WITH AN R2 ANTISENSE CONSTRUCT

| CONSTRUCT | CONC. (μm) | COLONY FORMING INHIBITION OF: MDA435 |
|---|---|---|
| AS-II-2229B-20 | 0.02 | 25% |
| | 0.03 | 56% |
| | 0.05 | 78% |
| | 0.10 | 94% |
| | 0.20 | 99% |

TABLE 9

SYNERGISTIC EFFECT OF AS-II-2229B-20 ANTISENSE CONSTRUCT

| Cells | Drug | Drug Conc. | AS-II-2229B-20[a] 0.02 μM | Relative Colony Forming Efficiency[c] |
|---|---|---|---|---|
| Hela S3 | PALA[a] | 20 μM | − | 350 ± 50 |
| | PALA | 20 μM | + | 90 ± 10 |
| Hela S3 | MTX[a] | 40 μM | − | 118 ± 32 |
| | MTX | 60 μM | − | 116 ± 13 |
| | MTX | 40 μM | + | 25 ± 5 |
| | MTX | 60 μM | + | 0 |
| Hela 1 mM | PALA | 20 μM | − | 377 ± 21 |
| | PALA | 30 μM | − | 311 ± 9.5 |
| | PALA | 20 μM | + | 108 ± 7.5 |

TABLE 9-continued

SYNERGISTIC EFFECT OF AS-II-2229B-20 ANTISENSE CONSTRUCT

| Cells | Drug | Drug Conc. | AS-II-2229B-20[a] 0.02 μM | Relative Colony Forming Efficiency[c] |
|---|---|---|---|---|
| | PALA | 30 μM | + | 101 ± 2.0 |
| Hela 1 mM | MTX | 40 μM | − | 28 ± 10 |
| | MTX | 60 μM | − | 12 ± 0.5 |
| | MTX | 40 μM | + | 6.5 ± 5.5 |
| | MTX | 60 μM | + | 3.5 ± 0.5 |

[a]PALA = N-(phosphonacetyl)-L-aspartate
[a]MTX = methotrexate
[b]− = treatment
[b]+ = treatment provided
[c]The values are the average of two experiments.

TABLE 10

REDUCED COLONY FORMING EFFICIENCY FOLLOWING TREATMENT WITH R1 ANTISENSE CONSTRUCT

| Conc. AS-I-1395-20[a] | % Inhib. |
|---|---|
| CELL LINE: Hela S3 | |
| 0 | — |
| 0.2 μM | 75% (Exp. 1) |
| 0.2 μM | 77% (Exp. 2) |
| CELL LINE: Hela 1 mM | |
| 0 | — |
| 0.01 μM | 0 |
| 0.05 μM | 30% |
| 0.10 μM | 60% |
| CELL LINE: Mouse SC2 | |
| 0 | — |
| 0.2 μM | 76% |

TABLE 11

ANTISENSE SEQUENCES DESIGNED TO TARGET THE R1 MESSAGE

| SEQ ID No: | Name | Sequence 5'–3' | Tm °C. | dG kDa/mol |
|---|---|---|---|---|
| SEQ ID No:104 | AS-I-35-20 | GTT CCA GCC AGA CAG CAC TT | 51.7 | −37.3 |
| SEQ ID No:105 | AS-I-37-20 | GAG TTC CAG CCA GAC AGC AC | 52.0 | −37.0 |
| SEQ ID No:106 | AS-I-85-20 | CAG AGT GGG AAG GGT TAG GT | 49.7 | −37.5 |
| SEQ ID No:107 | AS-I-91-20 | AGG TGA CAG AGT GGG AAG GG | 52.7 | −38.2 |
| SEQ ID No:108 | AS-I-129-20 | GAC TGG ACT GCG GCT CTA AA | 52.1 | −38.3 |
| SEQ ID No:109 | AS-I-203-20 | ATG ACT CGT TCT TGG CGG CC | 58.6 | −42.4 |
| SEQ ID No:110 | AS-I-239-20 | CAA AGC TTC TGG ATT CGA GA | 49.6 | −37.1 |
| SEQ ID No:111 | AS-I-287-20 | TTC ATG GTG ATC TGA GCA GG | 50.6 | −36.2 |
| SEQ ID No:112 | AS-I-300-20 | GCC TTG GAT TAC TTT CAT GG | 48.9 | −37.3 |
| SEQ ID No:113 | AS-I-348-20 | TTC AGC AGC CAA AGT ATC TA | 45.4 | −34.9 |
| SEQ ID No:114 | AS-I-395-20 | GCC AGG ATA GCA TAG TCA GG | 48.9 | −36.9 |
| SEQ ID No:115 | AS-I-439-20 | CTT TCT TTG TTT CTT TGT GC | 44.5 | −34.6 |
| SEQ ID No:116 | AS-I-504-20 | GGG AGA GTG TTT GCC ATT AT | 48.2 | −36.7 |
| SEQ ID No:117 | AS-I-520-20 | TTG ACT TGG CCA CCA TGG GA | 58.2 | −40.8 |
| SEQ ID No:118 | AS-I-540-20 | GGC CAG AAC AAT ATC CAA TG | 49.5 | −37.2 |
| SEQ ID No:119 | AS-I-556-20 | TCA GGC GAT CTT TAT TGG CC | 54.2 | −40.5 |
| SEQ ID No:120 | AS-I-635-20 | TTC AAC AAA TAA GAC CGC TC | 47.2 | −36.1 |
| SEQ ID No:121 | AS-I-658-20 | TTT CAG CCA CTT TTC CAT TG | 50.3 | −37.5 |
| SEQ ID No:122 | AS-I-662-20 | GGT CTT TCA GCC ACT TTT CC | 50.4 | −37.9 |
| SEQ ID No:123 | AS-I-782-20 | TTG AAG AGA GTG GGC GAA GC | 54.4 | −39.6 |
| SEQ ID No:124 | AS-I-786-20 | AGC ATT GAA GAG AGT GGG CG | 54.3 | −39.5 |
| SEQ ID No:125 | AS-I-809-20 | GAA AGT TGC GGG CGG TTG GT | 60.6 | −44.3 |
| SEQ ID No:126 | AS-I-843-20 | GCT GTC ATC TTT CAT ACT CA | 41.9 | −32.2 |
| SEQ ID No:127 | AS-I-908-20 | CCA ATT CCT CCA GCA GAC TT | 50.8 | −37.8 |
| SEQ ID No:128 | AS-I-923-20 | CAA CTC ACA GCA ACA CCA AT | 48.1 | −34.8 |
| SEQ ID No:129 | AS-I-932-20 | GCC CGA ATA CAA CTC ACA GC | 52.2 | −38.2 |
| SEQ ID No:130 | AS-I-967-20 | AAT TGC CAT TAG TCC CAG CA | 52.2 | −38.8 |
| SEQ ID No:131 | AS-I-1051-20 | ATG CCC CAG GAC GCT TGT TC | 58.5 | −42.2 |
| SEQ ID No:132 | AS-I-1074-20 | CCA AGG CTC CAG GTA AAT AG | 48.4 | −37.6 |
| SEQ ID No:133 | AS-I-1134-20 | ACG CTG CTC TTC CTT TCC TG | 53.7 | −39.6 |
| SEQ ID No:134 | AS-I-1162-20 | TCC AAA GAG CAA AGA AAA GA | 47.0 | −36.1 |
| SEQ ID No:135 | AS-I-1258-20 | CCT CTC CCC AAA CCT CAT CC | 54.7 | −40.2 |
| SEQ ID No:136 | AS-I-1311-20 | AAC TTT GCG GAC ACG ACC TT | 53.7 | −39.5 |
| SEQ ID No:137 | AS-I-1370-20 | GGG GTG CCT GTT TCC GTC TG | 58.9 | −42.0 |
| SEQ ID No:138 | AS-I-1418-20 | TTC TGC TGG TTG CTC TTT CG | 53.1 | −38.7 |
| SEQ ID No:139 | AS-I-1421-20 | AGG TTC TGC TGG TTG CTC TT | 50.6 | −37.6 |
| SEQ ID No:140 | AS-I-1513-20 | GGG CCA GGG AAG CCA AAT TA | 57.6 | −43.4 |
| SEQ ID No:141 | AS-I-1662-20 | GGG GCG ATG GCG TTT ATT TG | 58.8 | −44.0 |
| SEQ ID No:142 | AS-I-1666-20 | CAA TGG GGC GAT GGC GTT TA | 60.1 | −44.0 |
| SEQ ID No:143 | AS-I-1785-20 | TTC CAG AGC ACC ATA ATA AA | 45.1 | −35.1 |
| SEQ ID No:144 | AS-I-1818-20 | TGG GCC CTG CTC CTT GGC AA | 64.3 | −45.7 |
| SEQ ID No:145 | AS-I-1970-20 | GGC ATC GGG GCA ATA AGT AA | 54.1 | −41.0 |
| SEQ ID No:146 | AS-I-1976-20 | GCT GTA GGC ATC GGG GCA AT | 58.5 | −42.9 |

TABLE 11-continued

ANTISENSE SEQUENCES DESIGNED TO TARGET THE R1 MESSAGE

| SEQ ID No: | Name | Sequence 5'–3' | Tm °C. | dG kDa/mol |
|---|---|---|---|---|
| SEQ ID No:147 | AS-I-2119-20 | CAT GCC ATA GGC CCC GCT CG | 64.0 | −46.4 |
| SEQ ID No:148 | AS-I-2198-20 | AGT TGC TTC AGG TCA TCA GG | 49.0 | −36.0 |
| SEQ ID No:149 | AS-I-2251-20 | CAG CTG CCA TCT TGA GAA CA | 51.1 | −36.6 |
| SEQ ID No:150 | AS-I-2304-20 | CTC AGC AAT GTG GAT GTT CA | 48.9 | −35.0 |
| SEQ ID No:151 | AS-I-2364-20 | AGT CTT CAA ACC CTG CTT CC | 50.0 | −37.6 |
| SEQ ID No:152 | AS-I-2370-20 | CAT CCC AGT CTT CAA ACC CT | 50.4 | −37.5 |
| SEQ ID No:153 | AS-I-2414-20 | GTG AAC TGG ATT GGA TTAGC | 46.1 | −35.2 |
| SEQ ID No:154 | AS-I-2491-20 | TGG CTG CTG TGT TCC TCT CC | 55.0 | −38.8 |
| SEQ ID No:155 | AS-I-2556-20 | CTT CCA AGT CTT TCC TCA GG | 48.0 | −36.4 |
| SEQ ID No:156 | AS-I-2629-20 | TAC CAC CTC AAG CAA ACC CA | 52.9 | −38.4 |
| SEQ ID No:157 | AS-I-2650-20 | CAA CAG GGT CCA GCA AAG CC | 56.8 | 40.9 |
| SEQ ID No:158 | AS-I-2769-20 | TCC GTT TTT TTT TTC TTT TT | 46.2 | −37.5 |
| SEQ ID No:159 | AS-I-2863-20 | TGC TAA ATG GGT GAT GAA AC | 47.5 | −35.8 |
| SEQ ID No:160 | AS-I-2922-20 | CCC ACC AGT CAA AGC AGT AA | 50.2 | −36.9 |
| SEQ ID No:161 | AS-I-2594-20 | CTC AAG AAG TAG TTT GGC TA-3' | 41.6 | −33.2 |

Footnotes for Table 11
Name includes the following:
AS = antisense
I = R1
The first number indicates the first nucleotide position in the R1 mRNA sequence.
The second number indicates the length of sequence segment.
[1]Tm °C. = Melting temperature of oligonucleotide duplex formed.
[2]dG = Free energy value for oligonucleotide-complement dimer formation.
In addition to the above analysis, estimates of potential dimer formation (D), potential self-complementary interactions (H), and the potential to bind to sequences in the R1 message other than the target sequence (B), were obtained. Analyses were performed as described in the Footnote to Table 7, and criteria used to select the sequences shown in Table 11 were as indicated in the Footnote to Table 7.

TABLE 12

Reduced Relative Colony Forming Efficiency of Human Tumor Cells Following Treatment with 0.2 μM of Various Antisense Oligodeoxyribonucleotide Phosphorothioates Targeting the R2 Message, Expressed As % Inhibition

| Name (Re) | T24 | HCT116 | A549 | MDA-MB-231 | MIA PaCa-2 | PC-3 | HepG2 | Hela S3 | T-47D | H596 | Colo320 |
|---|---|---|---|---|---|---|---|---|---|---|---|
| AS-II-6-20 | 73.85 | ND | ND | 88.40 | 95.15 | 89.21 | 97.89 | ND | ND | ND | ND |
| AS-II-13-20* | 18.99 | 6.95 | 32.30 | 45.45 | ND | 52.38 | 24.11 | 19.85 | 15.33 | 19.68 | ND |
| AS-II-14-20 | 77.59 | ND | ND | 91.24 | 47.93 | 92.76 | 88.40 | ND | ND | ND | ND |
| AS-II-16-18 | 25.74 | 78.57 | 81.10 | 62.59 | ND | 89.48 | 75.89 | 68.70 | 7.13 | 34.50 | ND |
| AS-II-75-20* | 73.42 | 44.40 | 60.08 | 49.30 | 97.38 | 68.25 | 35.40 | 93.01 | 32.95 | ND | ND |
| AS-II-75-20 | 95.83 | ND | ND | 95.14 | 52.07 | 83.46 | 97.89 | ND | ND | ND | ND |
| AS-II-79-14 | 38.40 | 45.56 | 79.17 | 48.60 | 38.89 | 85.32 | 70.81 | 28.64 | 70.81 | ND | ND |
| AS-II-109-20* | 24.89 | 6.76 | 15.14 | 22.38 | 54.24 | 61.51 | 18.08 | 46.83 | 20.63 | 7.28 | ND |
| AS-II-110-20 | 87.78 | 71.69 | 89.38 | 90.92 | 47.51 | 92.06 | 97.14 | 53.98 | ND | ND | ND |
| AS-II-114-20 | 87.45 | 86.10 | 83.51 | 76.22 | 90.05 | 92.66 | 78.72 | 79.25 | 90.83 | 46.30 | ND |
| AS-II-127-12 | 50.63 | 54.34 | 69.33 | 38.46 | 53.24 | 79.56 | 71.75 | 86.45 | 37.54 | ND | ND |
| AS-II-130-20 | 51.94 | 57.98 | 86.48 | ND | 82.11 | 74.66 | 94.28 | ND | ND | ND | ND |
| AS-II-134-20 | ND | ND | ND | ND | ND | 77.51 | ND | ND | ND | ND | ND |
| AS-II-151-20 | ND | 78.09 | 84.28 | 41.64 | 75.38 | 85.68 | 89.58 | 66.75 | 95.89 | 69.12 | 90.12 |
| AS-II-163-20* | 5.49 | 29.05 | 37.13 | 22.73 | 9.88 | 7.14 | 18.64 | 45.80 | 9.81 | 32.08 | ND |
| AS-II-166-20 | 68.99 | 73.84 | 81.10 | 29.02 | 91.36 | 74.11 | 78.72 | 80.10 | 91.40 | 61.99 | ND |
| AS-II-185-20 | 21.94 | ND | 71.51 | 17.40 | 29.32 | 4.37 | 53.44 | 19.38 | 94.52 | 24.53 | ND |
| AS-II-189-20 | 18.57 | 86.78 | 76.57 | 39.86 | 70.52 | 73.12 | 57.86 | 76.67 | 96.63 | 26.15 | ND |
| AS-II-201-20 | 96.20 | 45.56 | 90.55 | 25.17 | 70.22 | 65.08 | 59.32 | 90.87 | 98.53 | 49.60 | ND |
| AS-II-217-20 | 65.02 | 61.85 | ND | 52.70 | 87.38 | 87.41 | 99.55 | ND | ND | ND | ND |
| AS-II-225-20 | 73.23 | 59.50 | 92.90 | ND | 95.44 | 80.06 | ND | 96.99 | ND | ND | ND |
| AS-II-253-14 | 19.41 | 53.28 | 61.62 | 45.37 | ND | 67.26 | 42.00 | 65.18 | 27.09 | 0.81 | ND |
| AS-II-280-20 | 90.56 | 69.42 | 61.81 | 79.14 | 53.94 | 77.51 | 97.14 | 41.79 | ND | ND | ND |
| AS-II-288-12 | 30.38 | 67.57 | 70.49 | 52.10 | 30.09 | 74.01 | 65.89 | 57.63 | ND | 12.67 | ND |
| AS-II-323-20 | ND | 55.80 | 91.24 | ND | 97.55 | 79.76 | 96.39 | ND | ND | ND | ND |
| AS-II-344-20 | ND | ND | ND | ND | ND | 80.06 | ND | ND | ND | ND | ND |
| AS-II-362-20 | 89.63 | 62.81 | 61.81 | 85.83 | 34.20 | 75.78 | 95.78 | 45.69 | ND | ND | ND |
| AS-II-391-17 | ND | ND | ND | ND | 26.35 | 93.25 | 60.64 | ND | ND | ND | ND |
| AS-II-404-20 | 84.26 | ND | 52.17 | 85.83 | 17.84 | 77.08 | 84.79 | 58.37 | ND | ND | ND |
| AS-II-412-20 | 22.20 | 27.98 | 43.78 | ND | 55.25 | 73.96 | 26.23 | ND | ND | ND | ND |
| AS-II-414-20 | 11.67 | 19.10 | 12.44 | ND | 36.11 | 60.94 | 30.89 | ND | ND | ND | ND |
| AS-II-425-20 | 90.37 | ND | 57.38 | 89.75 | 65.20 | 75.65 | 97.89 | 63.09 | ND | ND | ND |
| AS-II-439-20 | 67.84 | 64.70 | 76.46 | ND | 92.69 | 77.66 | 73.04 | ND | ND | ND | ND |
| AS-II-472-20 | 69.26 | 67.23 | 96.99 | ND | 97.13 | 90.70 | ND | ND | ND | ND | ND |
| AS-II-494-20 | 54.23 | 50.28 | 33.85 | 54.78 | 25.31 | 80.60 | 93.37 | 48.62 | ND | ND | ND |
| AS-II-496-16 | 78.48 | 70.85 | 74.45 | 45.80 | ND | 88.84 | 54.80 | 52.21 | 10.79 | ND | ND |

TABLE 12-continued

Reduced Relative Colony Forming Efficiency of Human Tumor Cells Following Treatment with 0.2 μM of Various Antisense Oligodeoxyribonucleotide Phosphorothioates Targeting the R2 Message, Expressed As % Inhibition

| Name (Re) | T24 | HCT116 | A549 | MDA-MB-231 | MIA PaCa-2 | PC-3 | HepG2 | Hela S3 | T-47D | H596 | Colo320 |
|---|---|---|---|---|---|---|---|---|---|---|---|
| AS-II-549-20 | 45.46 | 47.83 | 30.57 | 40.13 | 17.01 | ND | 84.04 | 27.80 | ND | ND | ND |
| AS-II-579-20 | 76.68 | 69.08 | 95.49 | 66.89 | 97.55 | 88.16 | 94.28 | ND | ND | ND | ND |
| AS-II-619-20 | 86.30 | ND | 65.67 | 91.08 | 39.83 | 88.01 | 92.02 | 31.22 | ND | ND | ND |
| AS-II-626-20 | 76.79 | 70.46 | 95.14 | 90.21 | 75.62 | 83.23 | 75.89 | 67.92 | 66.12 | ND | ND |
| AS-II-634-20 | 83.52 | ND | 57.76 | 92.44 | ND | 77.86 | 95.78 | 48.94 | ND | ND | ND |
| AS-II-667-20 | 70.48 | 76.90 | 70.30 | ND | 85.26 | 91.80 | 88.23 | ND | ND | ND | ND |
| AS-II-784-20 | 87.23 | 78.09 | 83.80 | 33.92 | 62.04 | 88.99 | 80.89 | 81.48 | 85.39 | ND | ND |
| AS-II-798-20 | 84.72 | 64.46 | 70.49 | 83.92 | 34.65 | 83.21 | 89.46 | 56.42 | ND | ND | ND |
| AS-II-816-20 | 73.91 | 88.22 | 78.40 | ND | 93.21 | 94.08 | 93.08 | ND | ND | ND | ND |
| AS-II-861-20 | 73.50 | 74.20 | 95.78 | 89.98 | 97.30 | 87.33 | 96.08 | ND | ND | ND | ND |
| AS-II-890-20 | 82.07 | ND | 81.60 | 88.20 | 66.02 | 87.93 | ND | ND | ND | ND | ND |
| AS-II-909-20 | 78.57 | ND | 78.68 | 45.96 | 46.13 | 84.86 | ND | ND | ND | ND | ND |
| AS-II-933-20 | 64.84 | 67.24 | 53.52 | 64.89 | 35.68 | 86.91 | 79.97 | 26.86 | ND | ND | ND |
| AS-II-981-20 | 86.30 | 66.84 | 74.25 | 91.48 | ND | 85.16 | 95.03 | 69.43 | ND | ND | ND |
| AS-II-1001-20 | 86.11 | 55.58 | 71.36 | 82.17 | 64.21 | 85.94 | 90.36 | ND | ND | ND | ND |
| AS-II-1006-20 | 61.49 | 45.56 | 61.62 | ND | 47.93 | 92.58 | 89.31 | 41.79 | ND | ND | ND |
| AS-II-1023-20 | 58.26 | ND | 34.52 | ND | 42.82 | 87.63 | ND | ND | ND | ND | ND |
| AS-II-1040-20 | 59.49 | 70.08 | 85.82 | ND | 43.52 | 40.08 | 77.78 | 71.87 | 64.76 | ND | ND |
| AS-II-1048-20 | 40.32 | 42.63 | 65.67 | 66.88 | 33.40 | 84.38 | 77.56 | 39.19 | ND | ND | ND |
| AS-II-1144-20 | 62.90 | 54.25 | 61.81 | ND | 46.89 | 80.21 | 92.17 | 50.57 | ND | ND | ND |
| AS-II-1182-20 | 94.51 | 88.13 | 80.06 | ND | 84.72 | 92.76 | 92.23 | 90.61 | 92.41 | ND | ND |
| AS-II-1197-20 | 90.30 | 84.85 | 89.15 | 50.35 | 70.68 | 74.40 | 76.32 | 82.68 | 81.95 | ND | ND |
| AS-II-1217-20 | 66.36 | 68.68 | 91.49 | ND | 34.85 | 81.03 | ND | ND | ND | ND | ND |
| AS-II-1224-20 | 38.31 | 41.78 | 55.06 | ND | 17.22 | 80.66 | 76.05 | 14.80 | ND | ND | ND |
| AS-II-1254-20 | 41.53 | 28.54 | 36.74 | ND | 3.32 | 73.31 | 83.28 | 7.64 | ND | ND | ND |
| AS-II-1278-20 | 65.42 | ND | ND | 90.68 | 57.05 | 85.31 | ND | ND | ND | ND | ND |
| AS-II-1288-20 | 56.75 | 66.43 | 61.04 | ND | 80.71 | 93.55 | 80.41 | ND | ND | ND | ND |
| AS-II-1302-20 | 70.56 | 71.98 | 93.17 | 92.20 | 23.86 | 79.01 | ND | ND | ND | ND | ND |
| AS-II-1335-20 | 59.95 | 67.87 | 78.59 | ND | 78.78 | 90.04 | 72.98 | ND | ND | ND | ND |
| AS-II-1338-20 | 63.16 | 74.73 | 63.93 | ND | 79.17 | 93.75 | 80.41 | ND | ND | ND | ND |
| AS-II-1342-20 | 59.76 | 73.74 | 65.67 | ND | 73.77 | 89.84 | 82.20 | ND | ND | ND | ND |
| AS-II-1345-20 | 51.26 | 65.70 | 73.10 | 94.11 | 77.39 | 89.58 | 75.42 | ND | ND | ND | ND |
| AS-II-1362-20 | ND | 78.47 | 83.90 | 70.22 | 44.14 | 77.38 | 80.41 | ND | ND | ND | ND |
| AS-II-1364-20 | 66.59 | 77.29 | 95.59 | 93.87 | 59.34 | 79.01 | ND | ND | ND | ND | ND |
| AS-II-1381-20 | 71.37 | 89.48 | 86.02 | 44.41 | 73.77 | 75.00 | 62.34 | 80.53 | 93.62 | 45.28 | ND |
| AS-II-1390-20 | 61.13 | 62.18 | 88.31 | 66.89 | 82.77 | 76.76 | 90.21 | ND | ND | ND | ND |
| AS-II-1438-20 | 43.70 | ND | 51.27 | 69.06 | 42.13 | 83.96 | ND | ND | ND | ND | ND |
| AS-II-1499-20 | 82.81 | 83.01 | 87.80 | 41.26 | 81.17 | 77.28 | 77.50 | 87.56 | 96.67 | 78.30 | ND |
| AS-II-1517-20 | ND | ND | ND | ND | ND | 91.75 | ND | ND | ND | ND | ND |
| AS-II-1538-20 | 67.29 | 51.28 | 90.34 | ND | 50.62 | 84.71 | 96.84 | ND | ND | ND | ND |
| AS-II-1560-20 | 32.49 | 85.81 | 84.19 | 46.15 | 83.80 | 78.37 | 73.63 | 82.16 | 86.60 | 71.16 | ND |
| AS-II-1581-20 | 68.22 | 66.85 | 90.55 | ND | 24.07 | 85.83 | 93.07 | ND | ND | ND | ND |
| AS-II-1659-20 | 74.09 | ND | 54.70 | 42.86 | 42.54 | 81.56 | ND | ND | ND | ND | ND |
| AS-II-1666-20 | 71.71 | ND | 54.82 | 26.71 | 49.72 | 86.06 | ND | ND | ND | ND | ND |
| AS-II-1700-20 | 70.94 | ND | 77.28 | 30.75 | 34.52 | 90.63 | ND | ND | ND | ND | ND |
| AS-II-1768-20 | 74.56 | ND | 86.80 | 91.56 | 60.36 | 86.36 | ND | ND | ND | ND | ND |
| AS-II-1773-20 | 15.19 | 75.58 | 70.11 | 44.76 | 45.68 | 70.04 | 58.19 | 80.27 | 84.38 | 66.04 | ND |
| AS-II-1775-12 | 85.54 | 54.44 | 63.55 | 48.60 | 27.78 | 78.17 | 43.97 | 68.61 | ND | 18.60 | ND |
| AS-II-1790-20 | ND | ND | ND | ND | ND | 87.86 | ND | ND | ND | ND | ND |
| AS-II-1819-20 | 53.74 | ND | ND | 90.68 | 20.62 | 85.46 | 83.89 | ND | ND | ND | ND |
| AS-II-1976-20 | ND | ND | ND | 89.60 | ND | 88.16 | ND | ND | ND | ND | ND |
| AS-II-1989-20 | 77.43 | 78.47 | 83.90 | 54.90 | 70.22 | 77.38 | 80.70 | 61.41 | 90.83 | 56.33 | ND |
| AS-II-2009-20 | 61.84 | 69.92 | 93.32 | 96.25 | 93.74 | 83.36 | 96.99 | ND | ND | ND | ND |
| AS-II-2026-20 | 95.46 | 81.47 | 88.81 | 77.10 | 87.65 | 95.29 | 94.54 | 83.79 | 93.41 | 84.16 | ND |
| AS-II-2044-20 | 53.63 | 49.34 | 25.55 | 19.11 | 24.48 | 74.48 | 62.35 | 24.55 | ND | ND | ND |
| AS-II-2067-20 | 49.60 | 47.16 | 64.71 | 49.68 | 41.08 | 85.94 | 90.36 | 24.88 | ND | ND | ND |
| AS-II-2083-20 | 82.43 | 87.46 | 90.65 | 68.88 | 71.00 | ND | 93.64 | 84.58 | 89.32 | 82.98 | 87.28 |
| AS-II-2083-20* | 9.52 | 41.16 | 31.73 | ND | ND | 82.03 | 46.14 | 6.96 | 48.61 | 49.87 | 52.54 |
| AS-II-2128-20 | 83.74 | ND | 87.31 | 91.30 | 39.23 | 88.89 | ND | ND | ND | ND | ND |
| AS-II-2151-20 | 79.83 | ND | 79.19 | 95.14 | 62.15 | 84.86 | ND | ND | ND | ND | ND |
| AS-II-2164-20 | 61.84 | 50.08 | 91.15 | 69.03 | 89.36 | 83.36 | 93.07 | ND | ND | ND | ND |
| AS-II-2182-20 | 67.76 | 77.66 | 90.97 | 84.95 | 56.43 | 85.91 | 95.48 | ND | ND | ND | ND |
| AS-II-2229A-20 | 50.34 | 93.01 | 69.72 | ND | 33.61 | 89.58 | 73.26 | 63.15 | 58.82 | ND | ND |
| AS-II-2372-20 | 61.13 | 64.70 | 96.41 | 90.09 | 94.36 | 86.06 | ND | ND | ND | ND | ND |

Legend to Table 12
The antisense oligonucleotides were fully thioated unless indicated (*), as described in Table 7.
The values for relative colony-forming efficiencies are averages obtained from 2–8 determinations.
ND = not determined.
The various cell lines were obtained from the American Type Culture Collection, Rockville, Maryland.
Information about these human cancer cells:
T24 = bladder cell carcinoma
HCT116 = colon cell carcinoma

TABLE 12-continued

Reduced Relative Colony Forming Efficiency of Human Tumor Cells Following Treatment with 0.2 μM of Various
Antisense Oligodeoxyribonucleotide Phosphorothioates Targeting the R2 Message, Expressed As % Inhibition

| Name (Re) | T24 | HCT116 | A549 | MDA-MB-231 | MIA PaCa-2 | PC-3 | HepG2 | Hela S3 | T-47D | H596 | Colo320 |
|---|---|---|---|---|---|---|---|---|---|---|---|

A549 = lung cell carcinoma
MDA-MB-231 = breast cell adenocarcinoma
MIA PaCa-2 = pancreatic cell carcinoma
PC-3 = prostate cell adenocarcinoma
HepG2 = hepatocellular carcinoma
HeIaS3 = cells isolated from a carcinoma of the cervix
T-47D = breast ductal carcinoma
H596 = lung adenosquamous carcinoma cells
Colo320 = colon cell adenocarcinoma

TABLE 13

Metastatic Characteristics of r-3 Mouse 10-T½ Tumor Cells in Syngeneic Mice Following of Treatment with the Antisense Oligonucleotide, AS-II-626-20

| | Experimental Metastasis | |
|---|---|---|
| Oligonucleotide* Treatment | Frequency of Mice with Tumors | Number of Lung Tumors (mean ± SE) |
| none | 4/4 | 6.0 ± 1.58 |
| 0.2 μM | 1/4 | 0.25 ± 0.25 |

*$10^5$ cells either treated for 4 hours with lipofectin without oligonucelotide supplement (none) or with lipofectin containing 0.2 μM AS-II-626-20, were injected intravenously (tail vein) into C3H/HeN syngeneic mice and lung tumors were analyzed as previously described (Damen, J.E., Greenberg, A.H. and Wright, J.A. Biochim, Biophys. Acta., 1097:103–110, 1991). The r-3 cell line is highly malignant and has been described previously(Taylor, W.R., Egan, S.E., Mowat, M., Grerenberg, A.H. and Wright, J.A. Oncogene, 7:1383–1390, 1992). The differences observed between the AS-II-626-20 treated and untreated groups were statistically significant (p value = 0.027). Clearly, AS-II-626-20 treated tumor cells exhibited a marked reduction in metastatic potential.

REFERENCES

Agrawal, 1996. Antisense oligonucleotides: towards clinical trials, TIBTECH, 14:376.

Agarwal et al., 1995. Oncogen, 11:427–438.

Akhter et al, 1991. Interactions of antisense DNA oligonucleotide analogs with phospholipid membranes (liposomes). Nuc. Res. 19:5551–5559.

Alessi et al., 1995. Meth. Enzymol. 255:279–290.

Amara et al., 1994. Phorbol ester modulation of a novel cytoplasmic protein binding activity at the 3'-untranslated region of mammalian ribonucleotide reductase R2 mRNA and role in message stability. J. Biol. Chem. 269:6709–7071.

Amara et al., 1995B. Defining a novel cis element in the 3'-untranslated region of mammalian ribonucleotide reductase component R2 mRNA: Role in transforming growth factor-$β_1$ induced mRNA stabilization. Nucleic Acids Res. 23:1461–1467.

Amara et al. 1996. Defining a novel cis-element in the 3'-untranslated region of mammalian ribonucleotide reductase component R2 mRNA: cis-trans interactions and message stability. J. Biol. Chem. 271:20126–20131.

Anazodo et al., 1995. Sequence-Specific Inhibition of Gene Expression by a Novel Antisense oligodeoxynucleotide Phosphonothioate Directed Against a Nonregulatory Region of the Human Immunodeficiency Virus Type 1 Genome. J. Virol. 69: 1794–1801.

Anazodo et al., 1996. Relative Levels of Inhibition of p24 Gene Expression by Different 20-mer Antisense Oligonucleotide Sequences Targeting Nucleotides +1129 to +1268 of the HIV-1 gag Genome: An Analysis of Mechanism Biochem. Biophys. Res. Commun. 229: 305–309.

Ashihara and Baserga, 1979. Cell Synchronization. Methods Enzymol. 58:248–262.

Blaesse, 1997. Gene Therapy for Cancer. Scientific American 276(6):111–115.

Björklund et al., 1993. Structure and promoter characterization of the gene encoding the large subunit (R1 Protein) of mouse ribonucleotide reductase. Proc. Natl. Acad. Sci. U.S.A. 90:11322–11326.

Blin and Stafford, 1976. A general method for isolation of high molecular weight DNA from eukaryotes. Nucleic Acids Res., 3: 2303–2308.

Blosmanis et al., 1987. Cancer Res 47:1273–1277.

Bradley et al., 1986. Proc. Natl. Acad. Sci. U.S.A. 83: 5277–5281.

Calabretta, et al, 1996. Antisense strategies in the treatment of leukemias. Semin. Oncol. 23:78.

Caras, 1985. Cloned Mouse Ribonucleotide Reductase Subunit M1 cDNA Reveals Amino Acid Sequence Homology with *Escherichia coli* and Herpesvirus Ribonucleotide Reductases. Biol Chem. 260:7015–7022.

Chadee et al, 1995. J. Biol. Chem. 270:20098–20105.

Chan et al., 1993. Biochemistry 32:12835–12840.

Chang et al., 1978. Phenotypic expression in *E. coli* of a DNA sequence coding for mouse dihydrofolate reductase. Nature, 275: 617–624.

Chen et al., 1993. Mammalian ribonucleotide reductase R1 mRNA stability under normal and phorbol ester stimulating conditions: involvement of a cis-trans interaction at the 3'-untranslated region. EMBO J., 12:3977–3986.

Chen et al., 1994B. Defining a novel ribonucleotide reductase R1 mRNA cis element that binds to an unique cytoplasmic trans-acting protein. Nucleic Acids Res., 22:4796–4797.

Choy et al., 1988. Molecular mechanisms of drug resistance involving ribonucleotide reductase: hydroxyurea resistance in a series of clonally related mouse cell lines selected in the presence of increasing drug concentrations. Cancer Res. 48:2029–2035.

Crooke, 1995. Progress in antisense therapeutics, Hematol. Pathol. 2:59.

Damen et al., 1989. Generation of metastatic variants in populations of mutator and amplificator mutants. J. Natl. Cancer Inst. 81:628–631.

Damen et al., 1991. Transformation and amplification of the K-fgf Protooncogene in NIH-3T3 cells, and induction of metastatic potential. Biochem Biophys. Acta 1097: 103–110.

Davis et al., 1994. Purification, Characterization, and Localization of Subunit Interaction Area of Recombinant Mouse Ribonucleotide Reductase R1 Subunit. Biol. Chem. 269:23171–23176.

Eckstein 1985. Nucleoside Phosphorothioates. Ann. Rev. Biochem. 54:367–402.

Egan, et al., 1987A. Expression of H-ras Correlates with Metastatic Potential: Evidence for Direct Regulation of the Metastatic Phenotype in 10T1/2 and NIH 3T3 Cells. Mol. Cell. Biol. 7:830–837.

Egan et al., 1987B. Transformation by oncogenes encoding protein kinases induces the metastatic phenotype. Science 238:202–205.

Eriksson et al., 1984. Cell cycle-dependent regulation of mammalian ribonucleotide reductase. The S phase-correlated increase in subunit M2 is regulated by de novo protein synthesis. J. Biol. Chem. 259:11695–11700.

Fan et al., 1996A. Ribonucleotide reductase R2 component is a novel malignancy determinant that cooperates with activated oncogenes to determine transformation and malignant potential. Proc. Natl. Acad. Sci. U.S.A. 93:14036–14040.

Fan et al., 1996B. A link between ferritin gene expression and ribonucleotide reductase R2 protein, as demonstrated by retroviral vector mediated stable expression of R2 cDNA. FEBS Lett. 382:145–148.

Felgner, 1997. Nonviral Strategeies for Gene Therapy. Scinetific American. June, 1997, pgs 102–106.

Flintoff, 1989. Methotrexate, In: Gupta, R. S. (ed.), Drug Resistance in Mammalian Cells, Boca Raton, Fla.: CRC Press, 1–14.

Gewirtz, 1993. Oligodeoxynucleotide-based therapeutics for human leukemias, Stem Cells Dayt. 11:96.

Gilboa et al., 1986. Transfer and expression of cloned genes using retroviral vectors. BioTechniques 4(6):504–512.

Gannon et al., 1990. Activating mutations in p53 produce a common conformational effect. A monoclonal antibody specific for the mutant form. EMBO J., 9: 1595–1602.

Hampel and Tritz, 1989. RNA Catalytic Properties of the Minimum (−) sTRSV Sequence. Biochemistry 28:4929–4933.

Hanania, et al 1995. Recent advances in the application of gene therapy to human disease. Am. J. Med. 99:537.

Huang et al., 1995A. Drug resistance and gene amplification potential regulated by transforming growth factor $\beta_1$ gene expression. Cancer Res. 55:1758–1762.

Huang et al., 1995B. Multiple effects on drug sensitivity, genome stability and malignant potential by combinations of H-as, c-myc and mutant p53 gene overexpression. Int. J. Oncol. 7:57–63.

Hunter, 1995. Protein kinases and phosphatases: The yin and yang of protein phosphorylation and signalling. Cell, 80: 225–236.

Hurta, et al., 1991. Early induction of ribonucleotide reductase gene expression by transforming growth factor $\beta_1$ in malignant H-ras transformed cell lines. J. Biol. Chem. 266:24097–24100.

Hurta and Wright, 1992. Alterations in the activity and regulation of mammalian ribonucleotide reductase by chlorambucil, a DNA damaging agent. J. Biol. Chem. 267:7066–7071.

Hurta and Wright, 1995. Malignant transformation by H-ras results in aberrant regulation of ribonucleotide reductase gene expression by transforming growth factor-$\beta_1$. J. Cell. Biochem. 57:543–556.

Iyer et al. 1990. J. Org. Chem. 55:4693–4699.

Jelinek et al., 1994. Mol. Cell. Biol., 14:8212–8218.

Jensen et al., 1994. Identification of genes expressed in premalignant breast disease by microscopy-directed cloning. Proc. Natl. Acad. Sci, U.S.A. 91:9257–9261.

Kern et al., 1992. Oncogenic forms of p53 inhibit p53-regulated gene expression. Science, 256: 827–830.

Kohn, 1996. Regulatory genes and drug sensitivity. J. Natl. Cancer Inst., 88: 1255–1256.

Koong et al., 1994. Cancer Res, 54:5273–5279.

Leevers et al., 1994. Nature, 369:411–414.

Lefebvre-d'Hellencourt et al, 1995. Immunomodulation by cytokine antisense oligonucleotides. Eur. Cytokine Netw. 6:7.

Lenormand et al., 1996. J. Biol. Chem., 271:15762–15768.

Lescure, et al., 1994. Preparation and Characterization of Novel Poly(methyoidene Malonate 2.1.2.)-Made Nanoparticles. Pharmaceutical research 11(9):1270–1277.

Lev-Lehman et al., 1997. Antisense Oligomers in vitro and in vivo. In Antisense Therapeutics, A. Cohen and S. Smicek, eds (Plenum Press, New York)

Lewis et al., 1978. Assay of ribonucleotide reduction in nucleotide-permeable hamster cells. J. Cell Physiol. 94:287–298.

Livingston et al., 1992. Altered cell cycle arrest and gene amplification potential accompany loss of wild type p53. Cell. 70: 923–935.

Loke et al, 1989. Characterization of oligonucleotide transport into living cells. PNAS U.S.A. 86:3474.

Lowe et al., 1994. Abrogation of oncogene-associated apoptosis allows transformation of p53-deficient cells. Proc. Natl. Acad. Sci. U.S.A., 91: 2026–2030.

Mai, 1994. Overexpression of c-myc precedes amplification of the gene encoding dihydrofolate reductase. Gene, 148: 253–260.

Mann et al., 1988. Ribonucleotide reductase M1 subunit in cellular proliferation, quiescence, and differentiation. J. Cancer Res. 48:5151–5156.

McClarty et al., 1988. Molecular mechanisms responsible for the drug-induced posttranscriptional modulation of ribonucleotide reductase levels in a hydroxyurea-resistant mouse L cell line. Biochemistry, 27: 7524–7531.

McClarty et al., 1990. Increased ferritin gene expression is associated with increased ribonucleotide reductase gene expression and the establishment of hydroxyurea resistance in mammalian cells. J. Biol. Chem. 265:7539–7547.

Miller et al., 1993. Use of retroviral vectors for gene transfer and expression. Meth. Enzymol. 217:581–599.

Morrison, 1991. Suppression of basic fibroblast growth factor expression by antisense oligonucleotides inhibits the growth of transformed human astrocytes. J. Biol. Chem. 266:728.

Otto et al., 1989. Increased incidence of CAD gene amplification in tumorigenic rat lines as an indicator of genomic instability of neoplastic cells. J.Biol. Chem. 264: 3390–3396.

Phillips, 1973. "Dye Exclusion Tests for Cell Viability" in Tissue Culture Methods and Applications (editors: P. F. Kruse, Jr. and M. K. Patterson, Jr.), Academic Press, New York and London, pp. 406–408.

Price et al., 1987. Proc. Natl. Acad. Sci. U.S.A. 84, 156–160.

Price and Calderwood, 1993. Increased sequence-specific p53-DNA binding activity after DNA damage is attenuated by phorbol esters. Oncogene, 8: 3055–3062.

Qiu et al., 1995. Nature 374:457–459.

Radhakrishnan et al., 1990. The automated synthesis of sulfur-containing oligodeoxyribonucleotides using 3H-1, 2-Benzodithiol-3-One 1,1 Dioxide as a sulfur-transfer reagent. J. Org. Chem. 55:4693–4699.

Reichard, 1993. From RNA to DNA, why so many ribonucleotide reductases? Science 60:1773–1777.

Rosolen et al., 1990. Cancer Res. 50:6316.

Saeki et al., 1995. Immunohistochemical detection of ribonucleotide reductase in human breast tumors. Int. J. Oncol. 6:523–529.

Salem et al., 1993. FEBS Letters 323: 93–95.

Scanlon et al., 1995. Oligonucleotides-mediated modulation of mammalian gene expression. FASEB J. 9:1288.

Shaw et al., 1991. Modified deoxyoligonucleotides stable to exonuclease degradation in serum. Nucleic Acids Res. 19:747–750.

Shigesada et al., 1985. Construction of a cDNA to the hamster CAD gene and its application toward defining the domain for aspartate transcarbamylase. Mol. Cell. Biol., 5: 1735–1742.

Spitzer and Eckstein 1988. Inhibition of deoxynucleases by phosphorothioate groups in oligodeoxyribonucleotides. Nucleic Acids Res. 18:11691–11704.

Stark et al., 1990. Gene Rearrangements, In: B. D. Hames and D. M. Glover (eds.) Frontiers in Molecular Biology, Oxford, United Kingdom: IRL; 99–149.

Stark, 1993. Regulation and mechanisms of mammalian gene amplification. Adv. Cancer Res., 61: 87–113.

Stokoe et al., 1994. Activation of Raf as a result of recruitment to the plasma membrane. Science 264:1463–1467.

Stubbe, 1989. Protein radical involvement in biological catalysis? Annu. Rev. Biochem. 58:257–285.

Sullivan (1994) "Development of Ribozymes for Gene Therapy", *J. Investigative Dermatology (Suppl)* 103:95S.

Symons (1989) "Self-cleavage of RNA in the replication of small pathogens of plants and animals", TIBS 14:445–450.

Symons (1992) "Small Catalytic RNAs", *Annu. Rev. Biochem.* 61:641–671.

Takenaka et al., 1995. Regulation of the sequence-specific DNA binding function of p53 by protein kinase C and protein phosphatases. J. Biol. Chem., 270: 5405–5411.

Taylor et al., 1992. Evidence for synergistic interactions between ras, myc and a mutant form of p53 in cellular transformation and tumor dissemination. Oncogene 7:1383–1390.

Thelander et al., 1985. Subunit M2 of mammalian ribonucleotide reductase. Characterization of a homogeneous protein isolated from M2-overproducing mouse cells. J. Biol. Chem. 260:2737–2741.

Thelander et al., 1980. Ribonucleotide reductase from calf thymus. Separation of the enzyme into two nonidentical subunits, proteins M1 and M2. J. Biol. Chem. 255:7426–7432.

Tonin et al., 1987. Chromosomal assignment of amplified genes in hydroxyurea resistant hamster cells. Cytogenet. Cell Genet. 45:102–108.

Uhlenbeck, 1987. "Small catalytic oligoribonucleotide" Nature 328:596–600.

Wagner et al., 1996. Potent and selective inhibition of gene expression by an antisense heptanucleotide. Nature Biotechnology 14:840–844.

Wagner, 1994. Gene inhibition using antisense oligodeoxynucleotides. Nature 372:333.

Weber, 1983. Biochemical strategy of cancer cells and the design of chemotherapy. Cancer Res. 43:3466–3492.

Whitesell et al., 1991. Episome-generated N-myc antisense RNA restricts the differentiation potential of primitive neuroectodermal cell lines. Mol. Cell. Biol. 11:1360.

Woolf et al., 1990. The stability, toxicity and effectiveness of unmodified and phosphorothioate antisense oligodeoxynucleotides in Xenopus oocytes and embryos. Nucleic Acids Res. 18:1763–1769.

Wright et al., 1987. Altered Expression of Ribonucleotide Reductase and Role of M2 Gene Amplification in Hydroxyurea-Resistant Hamster, Mouse, Rat, and Human Cell Lines. Somat. Cell Mol. Genet. 13:155–165.

Wright, 1989A. Altered mammalian ribonucleotide reductase from mutant cell lines. Encycl. Pharmacol. Therapeut. 128:89–111.

Wright et al., 1989B. Hydroxyurea and related compounds. In: R. S. Gupta (ed.), Drug Resistance in Mammalian Cells, Boca Raton, Fla.; CRC Press, Inc; 15–27.

Wright et al., 1990A. Regulation and drug resistance mechanisms of mammalian ribonucleotide reductase and the significance to DNA synthesis. Biochem. Cell Biol. 68:1364–1371.

Wright et al., 1993. Transforming growth factor β and fibroblast growth factor as promoters of tumor progression to malignancy. Crit. Rev. Oncogen. 4:473–492.

Yakubov et al, 1989. PNAS U.S.A. 86:6454.

Yin et al., 1992. Wild-type p53 restores cell cycle control and inhibits gene amplification in cells with mutant p53 alleles. Cell. 70: 937–948.

---

What is claimed is:

1. A synthetic antisense oligonucleotide comprising at least twelve nucleotides or nucleotide analogues and not longer than thirty-five nucleotides in length having a sequence complementary to a mRNA sequence of a mouse or human ribonucleotide reductase dimeric protein component R2 or sequence segment thereof wherein said antisense is selected to have a reduced dimer formation and reduced self-complementary interactions and inhibits tumor cell growth.

2. The synthetic antisense oligonucleotide as set forth in claim 1 wherein the antisense oligonucleotide has a sequence selected from the group consisting of SEQ ID No:1 through SEQ ID No:102 or an analogue thereof.

3. A synthetic antisense oligonucleotide comprising at least twelve nucleotides or nucleotide analogues and not longer than thirty-five nucleotides in length having a sequence complementary to the mRNA sequence of a mouse or human ribonucleotide reductase dimeric protein component R2 or sequence segment thereof wherein the antisense oligonucleotide has a nucleotide sequence as set forth in SEQ ID Nos: 1, 2, 12, 16, 18, 21, 25, 29, 34, 42, 44, 45, 46, 52, 53, 59, 60, 64, 65, 66, 68, 69, 70, 72, 73, 74, 76, 78, 79, 80, 90, 91, 92, 96, 99, 100, or 102 and inhibits tumor cell growth.

4. The synthetic antisense oligonucleotide as set forth in claim 1 wherein the antisense oligonucleotide has a sequence complementary to the coding sequence of ribonucleotide reductase component R2.

5. A synthetic antisense oligonucleotide comprising at least twelve nucleotides or nucleotide analogues and not longer than thirty-five nucleotides in length having a sequence complementary to a sequence segment of the mRNA sequence of a mouse or human ribonucleotide reductase dimeric protein component R1 wherein said antisense oligonucleotide sequence is selected to have a reduced dimer formation and reduced self-complementary interactions and inhibits tumor cell growth.

6. A synthetic antisense oligonucleotide comprising at least twelve nucleotides or nucleotide analogues and not longer than thirty-five nucleotides in length having a sequence segment complementary to a sequence segment of the mRNA sequence of a mouse or human ribonucleotide reductase dimeric protein component R1 wherein the antisense oligonucleotide has a nucleotide sequence selected from the group consisting of SEQ ID No:103 through SEQ ID No:161 or an analogue thereof.

7. The synthetic antisense oligonucleotide as set forth in claim 6 wherein the antisense oligonucleotide segment has a sequence as set forth in SEQ ID No:103.

8. A pharmaceutical composition for inhibiting tumor cell growth in a patient comprising an amount sufficient to inhibit tumor cell growth of an active ingredient of said antisense oligonucleotide as set forth in claim 5 and a pharmaceutically physiologically acceptable carrier or diluent.

9. A pharmaceutical composition for inhibiting tumorigenicity of a neoplastic cell in a patient comprising an amount sufficient to inhibit tumor cell growth of at least two active ingredients selected from antisense oligonucleotides at least twelve nucleotides or nucleotide analogues and not longer than thirty-five nucleotides in length having a sequence complementary to mRNA of ribonucleotide reductase dimeric protein component R2 or sequence segment thereof and a sequence complementary to a sequence segment of the mRNA of ribonucleotide reductase dimeric protein component R1 or sequence segment thereof; and a pharmaceutically physiologically acceptable carrier or diluent.

10. The pharmaceutical composition as set forth in claim 9 wherein said antisense oligonucleotide sequence is selected to have a reduced dimer formation and reduced self-complementary interactions.

11. A method of inhibiting the tumorigenicity of neoplastic cells in a patient which method comprises contacting the neoplastic cell with an amount sufficient to inhibit tumor cell growth of at least one antisense oligonucleotide consisting of a synthetic antisense oligonucleotide comprising at least twelve nucleotides or nucleotide analogues having a sequence complementary to the mRNA sequence of ribonucleotide reductase dimeric protein component R2 or sequence segment thereof.

12. The method as set forth in claim 11 wherein the antisense oligonucleotide has a sequence as set forth in SEQ ID Nos:1–102.

13. The method as set forth in claim 12 wherein the antisense oligonucleotide segment has a sequence as set forth in SEQ ID Nos:1, 2, 12, 16, 18, 21, 25, 29, 34, 42, 44, 45, 46, 52, 53, 59, 60, 64, 65, 66, 68, 70, 72, 73, 74, 76, 78, 79, 80, 90, 91, 92, 96, 99, 100, or 102.

14. A method of inhibiting the tumorigenicity of neoplastic cells in a patient which method comprises contacting the neoplastic cell with an amount sufficient to inhibit tumor cell growth of at least one antisense oligonucleotide as set forth in claim 5.

15. The method as set forth in claim 14 wherein the antisense oligonucleotide has a sequence as set forth in SEQ ID Nos:103–161.

16. The method as set forth in claim 15 wherein the antisense oligonucleotide has a sequence as set forth in SEQ ID NO:103.

17. A method of inhibiting the tumorigenicity of neoplastic cells in a patient which method comprises contacting said neoplastic cell with an amount sufficient to inhibit tumor cell growth of at least two active compositions selected from antisense oligonucleotides having a sequence complementary to mRNA of ribonucleotide reductase dimeric protein component R2 or sequence segment thereof and a sequence complementary to mRNA of ribonucleotide reductase dimeric protein component R1 of sequence segment thereof.

18. A method of inhibiting the tumorigenicity of neoplastic cells resistant to chemotherapeutic drugs in a patient which method comprises identifying patients who have tumors that are resistant to a chemotherapeutic drug; and contacting the tumor with the chemotherapeutic drug to which the tumor is resistant and at least one active composition selected from antisense oligonucleotides having a sequence complementary to the mRNA of ribonucleotide reductase dimeric protein component R2 or sequence segment thereof or oligonucleotides having a sequence complementary to a sequence segment of the mRNA of ribonucleotide reductase dimeric protein component R1 wherein the amount of the chemotherapeutic drug and the active composition is sufficient to inhibit tumor cell growth.

19. The method as set forth in claim 18 wherein the chemotherapeutic drug is selected from hydroxyurea, MTX and PALA.

20. The method as set forth in claim 18 wherein the amount of active composition is sufficient to inhibit tumor cell growth.

21. A method of increasing sensitivity of neoplastic cells to chemotherapeutic drugs in a patient by contacting the tumor with at least one active composition selected from antisense oligonucleotides having a sequence complementary to the mRNA of ribonucleotide reductase dimeric protein component R2 or sequence segment thereof or oligonucleotides having a sequence complementary to a sequence segment mRNA of ribonucleotide reductase dimeric protein component R1 and with a chemotherapeutic drug.

22. The method as set forth in claim 21 wherein the chemotherapeutic drug is selected from hydroxyurea, MTX and PALA.

23. The method as set forth in claim 21 wherein the amount of the active antisense composition is insufficient to inhibit tumor cell growth.

24. The method as set forth in claim 21 wherein the amount of the active antisense composition is sufficient to inhibit tumor cell growth.

25. The method as set forth in claim 23 wherein the amount of chemotherapeutic drug is sufficient to inhibit tumor cell growth.

26. The method as set forth in claim 24 wherein the amount of chemotherapeutic drug is sufficient to inhibit tumor cell growth.

27. A pharmaceutical composition for treating proliferative disorders in a patient comprising an amount sufficient to inhibit tumor cell growth of at least two active ingredients selected from antisense oligonucleotides comprising at least twelve nucleotides or nucleotide analogues and not longer than thirty-five nucleotides in length having a sequence complementary to mRNA of ribonucleotide reductase dimeric protein component R2 or sequence segment thereof and a sequence complementary to a sequence segment of the mRNA of ribonucleotide reductase dimeric protein component R1; and a pharmaceutically physiologically acceptable carrier or a diluent.

28. An isolated DNA with a sequence comprising a transcriptional initiation region and a sequence encoding an antisense oligonucleotide at least twelve nucleotides or nucleotide analogues and not longer than thirty-five nucleotides in length comprising a sequence selected from the group consisting of SEQ ID Nos:1–161.

29. A vector comprising a DNA with a sequence as set forth in claim 28.

30. A pharmaceutical composition for inhibiting tumor cell growth in a patient comprising an amount sufficient to inhibit tumor cell growth of an antisense oligonucleotide comprising at least twelve nucleotides or nucleotide analogues and not longer than thirty-five nucleotides in length having a sequence complementary to a mRNA sequence of ribonucleotide reductase dimeric protein component R2 or sequence segment thereof, wherein the antisense oligonucleotide is selected to have a reduced dimer formation and reduced self-complementary interactions and a pharmaceutically physiologically acceptable carrier or diluent.

31. A method of inhibiting metastasis of tumor cells in a patient, which method comprises administering to said patient an amount of an active composition sufficient to inhibit tumor cell growth selected from antisense oligonucleotides having a sequence complementary to mRNA of ribonucleotide reductase dimeric protein component R2 or sequence segment thereof and a sequence complementary to mRNA of ribonucleotide reductase dimeric protein component R1 or sequence segment thereof.

* * * * *

SEQUENCE LISTING (1) GENERAL INFORMATION:

(iii) NUMBER OF SEQUENCES: 163

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "ANTISENSE OLIGONUCLEOTIDE"

(iv) ANTI-SENSE: YES (xi) SEQUENCE DESCRIPTION: SEQ ID NO:1:

TCCTGGAAGA TCCTCCTCGC                       20

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:2:

TCCCACATAT GAGAAAACTC                                    20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:3:

ACCCTTCCCA TTGGCTGCGC                                    20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Partially thioated
            oligonucleotide"

(iv) ANTI-SENSE: YES (xi) SEQUENCE DESCRIPTION: SEQ ID NO:4:

GCCTCCGACC CTTCCCATTG                                    20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:5:

TGCCTCCGAC CCTTCCCATT                                    20

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:6:

TGCCTCCGAC CCTTCCCA                                                           18

(2) INFORMATION FOR SEQ ID NO:7:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Partially thioated
                oligonucleotide"

(iv) ANTI-SENSE: YES (xi) SEQUENCE DESCRIPTION: SEQ ID NO:7:

CGCGCGCTCC CGGCCCTTCC                                                         20

(2) INFORMATION FOR SEQ ID NO:8:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iv) ANTI-SENSE: YES (xi) SEQUENCE DESCRIPTION: SEQ ID NO:8:

CGCGCGCTCC CGGCCCTTCC                                                         20

(2) INFORMATION FOR SEQ ID NO:9:

(i) SEQUENCE CHARACTERISTICS:
            (A) LENGTH: 14 base pairs
            (B) TYPE: nucleic acid
            (C) STRANDEDNESS: single
            (D) TOPOLOGY: linear (ii) MOLECULE TYPE: other nucleic acid (iv) ANTI-SENSE: YES (xi) SEQUENCE DESCRIPTION: SEQ ID NO:9:

CGCGCTCCCG GCCC                                                               14

(2) INFORMATION FOR SEQ ID NO:10:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Partially thioated
                oligonucleotide"

(iv) ANTI-SENSE: YES (xi) SEQUENCE DESCRIPTION: SEQ ID NO:10:

CCCCTCACTC CAGCAGCCTT                                                         20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:11:

ACCCCTCACT CCAGCAGCCT                                          20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:12:

GGCGACCCCT CACTCCAGCA                                          20

(2) INFORMATION FOR SEQ ID NO:13:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:13:

GCACGGGCGA CC                                                            12

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:14:

TGGGACAGGG TGCACGGGCG                                          20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:15:

GACGGCTGGG ACAGGGTGCA                    20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:16:

GAGCAGCCAG GACAGGACGG                    20

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Partially thioated
            oligonucleotide"

(iv) ANTI-SENSE: YES (xi) SEQUENCE DESCRIPTION: SEQ ID NO:17:

GCGAAGCAGA GCGAGCAGCC                    20

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:18:

GCAGCGAAGC AGAGCGAGCA                    20

(2) INFORMATION FOR SEQ ID NO:19:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:19:

GGGAGAGCAT AGTGGAGGCG                    20

(2) INFORMATION FOR SEQ ID NO:20:

(i) SEQUENCE CHARACTERISTICS:
        (A) LENGTH: 20 base pairs
        (B) TYPE: nucleic acid

```
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:20:

CGGAGGGAGA GCATAGTGGA                                              20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:21:

GCGAGCGGGA CACGGAGGGA                                              20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:22:

CGGGTCCGTG ATGGGCGCGA                                              20

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:23:

AGCTGCTGCG GGTCCGTGAT                                              20

(2) INFORMATION FOR SEQ ID NO:24:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:24:

CCCCTTCAGC GGCG                                                    14
```

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:25:

CGGCGGCGTG TTCTCCTTGT                                      20

(2) INFORMATION FOR SEQ ID NO:26:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:26:

CGGCGGCGTG TT                                                12

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:27:

TCCTCGCGGT CTTGCTGGCC                                      20

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:28:

CCGTGGGCTC CTGGAAGATC                                      20

(2) INFORMATION FOR SEQ ID NO:29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:29:

CTGCTTTAGT TTTCGGCTCC                                                   20

(2) INFORMATION FOR SEQ ID NO:30:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: other nucleic acid (iv) ANTI-SENSE: YES (xi) SEQUENCE DESCRIPTION: SEQ ID NO:30:

CGGCTCATCC TCCACGC                                                      17

(2) INFORMATION FOR SEQ ID NO:31:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid (iv) ANTI-SENSE: YES (xi) SEQUENCE DESCRIPTION: SEQ ID NO:31:

GGTTTTCTCT CAGCAGCGGC                                                   20

(2) INFORMATION FOR SEQ ID NO:32:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid (iv) ANTI-SENSE: YES (xi) SEQUENCE DESCRIPTION: SEQ ID NO:32:

GCGGCGGGGG TTTTCTCTCA                                                   20

(2) INFORMATION FOR SEQ ID NO:33:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid (iv) ANTI-SENSE: YES (xi) SEQUENCE DESCRIPTION: SEQ ID NO:33:

AAGCGGCGGG GGTTTTCTCT                                                   20

(2) INFORMATION FOR SEQ ID NO:34:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid (iv) ANTI-SENSE: YES (xi) SEQUENCE DESCRIPTION: SEQ ID NO:34:

GGAAGATGAC AAAGCGGCGG                                     20

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:35:

ATGGTACTCG ATGGGGAAGA                                     20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:36:

AGCCTCTGCC TTCTTATACA                                    20

(2) INFORMATION FOR SEQ ID NO:37:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:37:

CCTCCTCGGC GGTCCAAAAG                                    20

(2) INFORMATION FOR SEQ ID NO:38:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:38:

TCCTCGGCGG TCCAAA                                          16

(2) INFORMATION FOR SEQ ID NO:39:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:39:

TATCTCTCCT CGGGTTTCAG                                                    20

(2) INFORMATION FOR SEQ ID NO:40:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:40:

GCAAAGAAAG CCAGAACATG                                                    20

(2) INFORMATION FOR SEQ ID NO:41:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:41:

TCGCTCCACC AAGTTTTCAT                                                    20

(2) INFORMATION FOR SEQ ID NO:42:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:42:

GGCTAAATCG CTCCACCAAG                                                    20

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:43:
```

```
AACTTCTTGG CTAAATCGCT                                              20
```

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:44:

```
GAAGCCATAG AAACAGCGGG                                              20
```

(2) INFORMATION FOR SEQ ID NO:45:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:45:

```
GACACAAGGC ATCGTTTCAA                                              20
```

(2) INFORMATION FOR SEQ ID NO:46:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:46:

```
TCTGCCTTCT TCTTGACACA                                              20
```

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:47:

```
ATCCAGCGCA AGGCCCAGTC                                              20
```

(2) INFORMATION FOR SEQ ID NO:48:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:48:

GCAAAGGCTA CAACACGTTC                                                        20

(2) INFORMATION FOR SEQ ID NO:49:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid (iv) ANTI-SENSE: YES (xi) SEQUENCE DESCRIPTION: SEQ ID NO:49:

AACCGGAAAA GAAAATGCCT                                                        20

(2) INFORMATION FOR SEQ ID NO:50:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid (iv) ANTI-SENSE: YES (xi) SEQUENCE DESCRIPTION: SEQ ID NO:50:

CAGAATATCG ACGCAAAAGA                                                        20

(2) INFORMATION FOR SEQ ID NO:51:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid (iv) ANTI-SENSE: YES (xi) SEQUENCE DESCRIPTION: SEQ ID NO:51:

GGCATCAGTC CTCGTTTCTT                                                        20

(2) INFORMATION FOR SEQ ID NO:52:

(i) SEQUENCE CHARACTERISTICS:
             (A) LENGTH: 20 base pairs
             (B) TYPE: nucleic acid
             (C) STRANDEDNESS: single
             (D) TOPOLOGY: linear (ii) MOLECULE TYPE: other nucleic acid (iv) ANTI-SENSE: YES (xi) SEQUENCE DESCRIPTION: SEQ ID NO:52:

TGTAAACCCT CATCTCTGCT                                                        20

(2) INFORMATION FOR SEQ ID NO:53:

(i) SEQUENCE CHARACTERISTICS:
             (A) LENGTH: 20 base pairs (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:53:

TCAGGCAAGC AAAATCACAG                                                  20

(2) INFORMATION FOR SEQ ID NO:54:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:54:

GAACATCAGG CAAGCAAAAT                                                  20

(2) INFORMATION FOR SEQ ID NO:55:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:55:

TTGTGTACCA GGTGTTTGAA                                                  20

(2) INFORMATION FOR SEQ ID NO:56:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:56:

CTCTCTCCTC CGATGGTTTG                                                  20

(2) INFORMATION FOR SEQ ID NO:57:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:57:

TTCTCTTACT CTCTCCTCCG                                                  20

(2) INFORMATION FOR SEQ ID NO:58:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:58:

```
GTATTGCTTC ATTAGAGTGC                                           20
```

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:59:

```
CCCAGTTCCA GCATAAGTCT                                           20
```

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:60:

```
AAAACCTTGC TAAAACCCAG                                           20
```

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:61:

```
CAAATGGGTT CTCTACTCTG                                           20
```

(2) INFORMATION FOR SEQ ID NO:62:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:62:

ATAAAGTCAA ATGGGTTCTC                                              20

(2) INFORMATION FOR SEQ ID NO:63:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:63:

TTAGTCTTTC CTTCCAGTGA                                              20

(2) INFORMATION FOR SEQ ID NO:64:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:64:

TCGCCTACTC TCTTCTCAAA                                              20

(2) INFORMATION FOR SEQ ID NO:65:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:65:

CCTCTGATAC TCGCCTACTC                                              20

(2) INFORMATION FOR SEQ ID NO:66:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:66:

GACATCACTC CCATCCTCTG                                              20

(2) INFORMATION FOR SEQ ID NO:67:

(i) SEQUENCE CHARACTERISTICS:
        (A) LENGTH: 20 base pairs
        (B) TYPE: nucleic acid
        (C) STRANDEDNESS: single (D) TOPOLOGY: linear (ii) MOLECULE TYPE: other nucleic acid (iv) ANTI-SENSE: YES (xi) SEQUENCE DESCRIPTION: SEQ ID NO:67:

GCATCCAAGG TAAAAGAATT                                              20

(2) INFORMATION FOR SEQ ID NO:68:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:68:

TCAGCATCCA AGGTAAAAGA                                              20

(2) INFORMATION FOR SEQ ID NO:69:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:69:

GAAGTCAGCA TCCAAGGTAA                                              20

(2) INFORMATION FOR SEQ ID NO:70:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:70:

TTAGAAGTCA GCATCCAAGG                                              20

(2) INFORMATION FOR SEQ ID NO:71:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:71:

GCACATCTTC AGTTCATTTA                                              20

(2) INFORMATION FOR SEQ ID NO:72:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: other nucleic acid (iv) ANTI-SENSE: YES (xi) SEQUENCE DESCRIPTION: SEQ ID NO:72:

GGGCACATCT TCAGTTCATT                                            20

(2) INFORMATION FOR SEQ ID NO:73:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:73:

AAAAATCAGC CAAGTAAGGG                                            20

(2) INFORMATION FOR SEQ ID NO:74:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:74:

ATGGAAAAAA AAAATCAGCC                                            20

(2) INFORMATION FOR SEQ ID NO:75:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:75:

TTCATGGTGT GGCTAGTTGG                                            20

(2) INFORMATION FOR SEQ ID NO:76:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:76:

AGGACTGGTT GTGAGGTAGC                                        20

(2) INFORMATION FOR SEQ ID NO:77:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:77:

CCAGCACTAT AAACAGACAG                                        20

(2) INFORMATION FOR SEQ ID NO:78:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:78:

TTCTGGCAAA AGGTGATACT                                        20

(2) INFORMATION FOR SEQ ID NO:79:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:79:

GTAAGTCACA GCCAGCCAGG                                        20

(2) INFORMATION FOR SEQ ID NO:80:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:80:

ACTGCCATTG TCACTGCTAT                                        20

(2) INFORMATION FOR SEQ ID NO:81:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:81:

TGGCTGTGCT GGTTAAAGGA                                                      20

(2) INFORMATION FOR SEQ ID NO:82:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:82:

TTTTAACTGG CTGTGCTGGT                                                      20

(2) INFORMATION FOR SEQ ID NO:83:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:83:

ATTAAAATCT GCGTTGAAGC                                                      20

(2) INFORMATION FOR SEQ ID NO:84:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:84:

TATCGCCGCC GTGAGTACAA                                                      20

(2) INFORMATION FOR SEQ ID NO:85:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:85:

GCTATTATCG CCGCCGTGAG                                                      20

(2) INFORMATION FOR SEQ ID NO:86:

(i) SEQUENCE CHARACTERISTICS:

(A) LENGTH: 12 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:86:

ATCGCCGCCG TG                                                                       12

(2) INFORMATION FOR SEQ ID NO:87:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:87:

GAAACCAAAT AAATCAAGCT                                                               20

(2) INFORMATION FOR SEQ ID NO:88:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:88:

TTAGTGGTCA GGAGAATGTA                                                               20

(2) INFORMATION FOR SEQ ID NO:89:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:89:

TGGCACCAAC TGACTAATAT                                                               20

(2) INFORMATION FOR SEQ ID NO:90:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:90:

CCTGTCTTCT ATCTGGCACC                                                               20

(2) INFORMATION FOR SEQ ID NO:91:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:91:

GCCACAGGAT AAAAACACAA                          20

(2) INFORMATION FOR SEQ ID NO:92:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:92:

CCCAGGACAC TACACAAGCC                          20

(2) INFORMATION FOR SEQ ID NO:93:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:93:

TCAGAGGGGG CAGAGAATCC                          20

(2) INFORMATION FOR SEQ ID NO:94:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:94:

TCCTTTATCC CACAACACTC                          20

(2) INFORMATION FOR SEQ ID NO:95:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:95:

CCTTGCCCTG AGAGATTCCT                                                    20

(2) INFORMATION FOR SEQ ID NO:96:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Partially thioated
            oligonucleotide"

(iv) ANTI-SENSE: YES (xi) SEQUENCE DESCRIPTION: SEQ ID NO:96:

CCTTGCCCTG AGAGATTCCT                                                    20

(2) INFORMATION FOR SEQ ID NO:97:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:97:

GGCCCAGATC ACCCCTAAAT                                                    20

(2) INFORMATION FOR SEQ ID NO:98:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:98:

AAACGGCTTC TCACACATAT                                                    20

(2) INFORMATION FOR SEQ ID NO:99:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:99:

GAGAAATAAA ATGAAACGGC                                                    20

(2) INFORMATION FOR SEQ ID NO:100:

(i) SEQUENCE CHARACTERISTICS:

(A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:100:

CGTTGAGGAA AATACAGTGA                                            20

(2) INFORMATION FOR SEQ ID NO:101:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:101:

GCTCCCACAT ATGAAAACTC                                            20

(2) INFORMATION FOR SEQ ID NO:102:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:102:

CACACAACCT ACTTACACCA                                            20

(2) INFORMATION FOR SEQ ID NO:103:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:103:

ACAGGAATCT TTGTAGAGCA                                            20

(2) INFORMATION FOR SEQ ID NO:104:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:104:

GTTCCAGCCA GACAGCACTT                                            20

(2) INFORMATION FOR SEQ ID NO:105:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:105:

GAGTTCCAGC CAGACAGCAC                                      20

(2) INFORMATION FOR SEQ ID NO:106:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:106:

CAGAGTGGGA AGGGTTAGGT                                      20

(2) INFORMATION FOR SEQ ID NO:107:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:107:

AGGTGACAGA GTGGGAAGGG                                      20

(2) INFORMATION FOR SEQ ID NO:108:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:108:

GACTGGACTG CGGCTCTAAA                                      20

(2) INFORMATION FOR SEQ ID NO:109:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:109:

ATGACTCGTT CTTGGCGGCC                    20

(2) INFORMATION FOR SEQ ID NO:110:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid (iv) ANTI-SENSE: YES (xi) SEQUENCE DESCRIPTION: SEQ ID NO:110:

CAAAGCTTCT GGATTCGAGA                    20

(2) INFORMATION FOR SEQ ID NO:111:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid (iv) ANTI-SENSE: YES (xi) SEQUENCE DESCRIPTION: SEQ ID NO:111:

TTCATGGTGA TCTGAGCAGG                    20

(2) INFORMATION FOR SEQ ID NO:112:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid (iv) ANTI-SENSE: YES (xi) SEQUENCE DESCRIPTION: SEQ ID NO:112:

GCCTTGGATT ACTTTCATGG                    20

(2) INFORMATION FOR SEQ ID NO:113:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid (iv) ANTI-SENSE: YES (xi) SEQUENCE DESCRIPTION: SEQ ID NO:113:

TTCAGCAGCC AAAGTATCTA                    20

(2) INFORMATION FOR SEQ ID NO:114:

(i) SEQUENCE CHARACTERISTICS:
       (A) LENGTH: 20 base pairs
       (B) TYPE: nucleic acid (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:114:

GCCAGGATAG CATAGTCAGG                                            20

(2) INFORMATION FOR SEQ ID NO:115:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:115:

CTTTCTTTGT TTCTTTGTGC                                            20

(2) INFORMATION FOR SEQ ID NO:116:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:116:

GGGAGAGTGT TTGCCATTAT                                            20

(2) INFORMATION FOR SEQ ID NO:117:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:117:

TTGACTTGGC CACCATGGGA                                            20

(2) INFORMATION FOR SEQ ID NO:118:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:118:

GGCCAGAACA ATATCCAATG                                            20

(2) INFORMATION FOR SEQ ID NO:119:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:119:

TCAGGCGATC TTTATTGGCC                                            20

(2) INFORMATION FOR SEQ ID NO:120:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:120:

TTCAACAAAT AAGACCGCTC                                            20

(2) INFORMATION FOR SEQ ID NO:121:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:121:

TTTCAGCCAC TTTTCCATTG                                            20

(2) INFORMATION FOR SEQ ID NO:122:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:122:

GGTCTTTCAG CCACTTTTCC                                            20

(2) INFORMATION FOR SEQ ID NO:123:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:123:

TTGAAGAGAG TGGGCGAAGC                    20

(2) INFORMATION FOR SEQ ID NO:124:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:124:

AGCATTGAAG AGAGTGGGCG                    20

(2) INFORMATION FOR SEQ ID NO:125:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:125:

GAAAGTTGCG GGCGGTTGGT                    20

(2) INFORMATION FOR SEQ ID NO:126:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:126:

GCTGTCATCT TTCATACTCA                    20

(2) INFORMATION FOR SEQ ID NO:127:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:127:

CCAATTCCTC CAGCAGACTT                    20

(2) INFORMATION FOR SEQ ID NO:128:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:128:

CAACTCACAG CAACACCAAT                     20

(2) INFORMATION FOR SEQ ID NO:129:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid (iv) ANTI-SENSE: YES (xi) SEQUENCE DESCRIPTION: SEQ ID NO:129:

GCCCGAATAC AACTCACAGC                     20

(2) INFORMATION FOR SEQ ID NO:130:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid (iv) ANTI-SENSE: YES (xi) SEQUENCE DESCRIPTION: SEQ ID NO:130:

AATTGCCATT AGTCCCAGCA                     20

(2) INFORMATION FOR SEQ ID NO:131:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid (iv) ANTI-SENSE: YES (xi) SEQUENCE DESCRIPTION: SEQ ID NO:131:

ATGCCCCAGG ACGCTTGTTC                     20

(2) INFORMATION FOR SEQ ID NO:132:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (ii) MOLECULE TYPE: other nucleic acid (iv) ANTI-SENSE: YES (xi) SEQUENCE DESCRIPTION: SEQ ID NO:132:

CCAAGGCTCC AGGTAAATAG                     20

(2) INFORMATION FOR SEQ ID NO:133:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iv) ANTI-SENSE: YES (xi) SEQUENCE DESCRIPTION: SEQ ID NO:133:

ACGCTGCTCT TCCTTTCCTG                                                   20

(2) INFORMATION FOR SEQ ID NO:134:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iv) ANTI-SENSE: YES (xi) SEQUENCE DESCRIPTION: SEQ ID NO:134:

TCCAAAGAGC AAAGAAAAGA                                                   20

(2) INFORMATION FOR SEQ ID NO:135:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iv) ANTI-SENSE: YES (xi) SEQUENCE DESCRIPTION: SEQ ID NO:135:

CCTCTCCCCA AACCTCATCC                                                   20

(2) INFORMATION FOR SEQ ID NO:136:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iv) ANTI-SENSE: YES (xi) SEQUENCE DESCRIPTION: SEQ ID NO:136:

AACTTTGCGG ACACGACCTT                                                   20

(2) INFORMATION FOR SEQ ID NO:137:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iv) ANTI-SENSE: YES (xi) SEQUENCE DESCRIPTION: SEQ ID NO:137:

```
GGGGTGCCTG TTTCCGTCTG                                                        20

(2) INFORMATION FOR SEQ ID NO:138:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:138:

TTCTGCTGGT TGCTCTTTCG                                                        20

(2) INFORMATION FOR SEQ ID NO:139:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:139:

AGGTTCTGCT GGTTGCTCTT                                                        20

(2) INFORMATION FOR SEQ ID NO:140:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:140:

GGGCCAGGGA AGCCAAATTA                                                        20

(2) INFORMATION FOR SEQ ID NO:141:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:141:

GGGGCGATGG CGTTTATTTG                                                        20

(2) INFORMATION FOR SEQ ID NO:142:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
```

(iv) ANTI-SENSE: YES (xi) SEQUENCE DESCRIPTION: SEQ ID NO:142:

CAATGGGGCG ATGGCGTTTA                                      20

(2) INFORMATION FOR SEQ ID NO:143:

(i) SEQUENCE CHARACTERISTICS:
     (A) LENGTH: 20 base pairs
     (B) TYPE: nucleic acid
     (C) STRANDEDNESS: single
     (D) TOPOLOGY: linear (ii) MOLECULE TYPE: other nucleic acid (iv) ANTI-SENSE: YES (xi) SEQUENCE DESCRIPTION: SEQ ID NO:143:

TTCCAGAGCA CCATAATAAA                                      20

(2) INFORMATION FOR SEQ ID NO:144:

(i) SEQUENCE CHARACTERISTICS:
     (A) LENGTH: 20 base pairs
     (B) TYPE: nucleic acid
     (C) STRANDEDNESS: single
     (D) TOPOLOGY: linear (ii) MOLECULE TYPE: other nucleic acid (iv) ANTI-SENSE: YES (xi) SEQUENCE DESCRIPTION: SEQ ID NO:144:

TGGGCCCTGC TCCTTGGCAA                                      20

(2) INFORMATION FOR SEQ ID NO:145:

(i) SEQUENCE CHARACTERISTICS:
     (A) LENGTH: 20 base pairs
     (B) TYPE: nucleic acid
     (C) STRANDEDNESS: single
     (D) TOPOLOGY: linear (ii) MOLECULE TYPE: other nucleic acid (iv) ANTI-SENSE: YES (xi) SEQUENCE DESCRIPTION: SEQ ID NO:145:

GGCATCGGGG CAATAAGTAA                                      20

(2) INFORMATION FOR SEQ ID NO:146:

(i) SEQUENCE CHARACTERISTICS:
     (A) LENGTH: 20 base pairs
     (B) TYPE: nucleic acid
     (C) STRANDEDNESS: single
     (D) TOPOLOGY: linear (ii) MOLECULE TYPE: other nucleic acid (iv) ANTI-SENSE: YES (xi) SEQUENCE DESCRIPTION: SEQ ID NO:146:

GCTGTAGGCA TCGGGGCAAT                                      20

(2) INFORMATION FOR SEQ ID NO:147:

(i) SEQUENCE CHARACTERISTICS:
     (A) LENGTH: 20 base pairs (B) TYPE: nucleic acid
            (C) STRANDEDNESS: single
            (D) TOPOLOGY: linear (ii) MOLECULE TYPE: other nucleic acid (iv) ANTI-SENSE: YES (xi) SEQUENCE DESCRIPTION: SEQ ID NO:147:

CATGCCATAG GCCCCGCTCG                                                   20

(2) INFORMATION FOR SEQ ID NO:148:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iv) ANTI-SENSE: YES (xi) SEQUENCE DESCRIPTION: SEQ ID NO:148:

AGTTGCTTCA GGTCATCAGG                                                   20

(2) INFORMATION FOR SEQ ID NO:149:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iv) ANTI-SENSE: YES (xi) SEQUENCE DESCRIPTION: SEQ ID NO:149:

CAGCTGCCAT CTTGAGAACA                                                   20

(2) INFORMATION FOR SEQ ID NO:150:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iv) ANTI-SENSE: YES (xi) SEQUENCE DESCRIPTION: SEQ ID NO:150:

CTCAGCAATG TGGATGTTCA                                                   20

(2) INFORMATION FOR SEQ ID NO:151:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid (iv) ANTI-SENSE: YES (xi) SEQUENCE DESCRIPTION: SEQ ID NO:151:

AGTCTTCAAA CCCTGCTTCC                                                   20

(2) INFORMATION FOR SEQ ID NO:152:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:152:

CATCCCAGTC TTCAAACCCT                                      20

(2) INFORMATION FOR SEQ ID NO:153:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:153:

GTGAACTGGA TTGGATTAGC                                      20

(2) INFORMATION FOR SEQ ID NO:154:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:154:

TGGCTGCTGT GTTCCTCTCC                                      20

(2) INFORMATION FOR SEQ ID NO:155:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:155:

CTTCCAAGTC TTTCCTCAGG                                      20

(2) INFORMATION FOR SEQ ID NO:156:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:156:

TACCACCTCA AGCAAACCCA                                                    20

(2) INFORMATION FOR SEQ ID NO:157:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:157:

CAACAGGGTC CAGCAAAGCC                                                    20

(2) INFORMATION FOR SEQ ID NO:158:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:158:

TCCGTTTTTT TTTTCTTTTT                                                    20

(2) INFORMATION FOR SEQ ID NO:159:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:159:

TGCTAAATGG GTGATGAAAC                                                    20

(2) INFORMATION FOR SEQ ID NO:160:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:160:

CCCACCAGTC AAAGCAGTAA                                                    20

(2) INFORMATION FOR SEQ ID NO:161:

(i) SEQUENCE CHARACTERISTICS:
        (A) LENGTH: 20 base pairs
        (B) TYPE: nucleic acid
        (C) STRANDEDNESS: single -continued (D) TOPOLOGY: linear (ii) MOLECULE TYPE: other nucleic acid (iv) ANTI-SENSE: YES (xi) SEQUENCE DESCRIPTION: SEQ ID NO:161:

CTCAAGAAGT AGTTTGGCTA                                               20

(2) INFORMATION FOR SEQ ID NO:162:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO:162:

GGACATGCCC GGGCATGTCC                                               20

(2) INFORMATION FOR SEQ ID NO:163:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid (iv) ANTI-SENSE: YES (xi) SEQUENCE DESCRIPTION: SEQ ID NO:163:

ACGCACTCAG CTAGTGACAC                                               20